United States Patent
Demopulos et al.

(10) Patent No.: US 9,254,271 B2
(45) Date of Patent: *Feb. 9, 2016

(54) ARTHROSCOPIC IRRIGATION SOLUTION AND METHOD FOR PERIPHERAL VASOCONSTRICTION AND INHIBITION OF PAIN AND INFLAMMATION

(75) Inventors: Gregory A. Demopulos, Mercer Island, WA (US); Pamela Pierce Palmer, San Francisco, CA (US); Jeffrey M. Herz, Mill Creek, WA (US)

(73) Assignee: Omeros Corporation, Seattle, WA (US)

( * ) Notice: Subject to any disclaimer, the term of this patent is extended or adjusted under 35 U.S.C. 154(b) by 198 days.

This patent is subject to a terminal disclaimer.

(21) Appl. No.: 12/384,781

(22) Filed: Apr. 8, 2009

(65) Prior Publication Data

US 2009/0253795 A1    Oct. 8, 2009

Related U.S. Application Data

(60) Division of application No. 10/138,193, filed on May 1, 2002, now abandoned, which is a continuation-in-part of application No. 09/839,633, filed on Apr. 20, 2001, now Pat. No. 7,091,181, which is a continuation-in-part of application No. PCT/US99/24672, filed on Oct. 20, 1999.

(60) Provisional application No. 60/105,029, filed on Oct. 20, 1998.

(51) Int. Cl.

| | |
|---|---|
| A61K 31/137 | (2006.01) |
| A61K 31/192 | (2006.01) |
| A61K 31/135 | (2006.01) |
| A61K 31/00 | (2006.01) |
| A61K 9/08 | (2006.01) |
| A61K 31/18 | (2006.01) |
| A61K 31/352 | (2006.01) |
| A61K 31/4045 | (2006.01) |
| A61K 31/4164 | (2006.01) |
| A61K 31/4168 | (2006.01) |
| A61K 31/4174 | (2006.01) |
| A61K 31/439 | (2006.01) |
| A61K 31/4406 | (2006.01) |
| A61K 31/4427 | (2006.01) |
| A61K 31/4439 | (2006.01) |
| A61K 31/444 | (2006.01) |
| A61K 31/465 | (2006.01) |
| A61K 31/48 | (2006.01) |
| A61K 31/498 | (2006.01) |
| A61K 31/506 | (2006.01) |
| A61K 31/538 | (2006.01) |
| A61K 31/55 | (2006.01) |
| A61K 31/675 | (2006.01) |
| A61K 45/06 | (2006.01) |
| A61K 38/04 | (2006.01) |

(52) U.S. Cl.
CPC . *A61K 31/00* (2013.01); *A61K 9/08* (2013.01); *A61K 31/18* (2013.01); *A61K 31/352* (2013.01); *A61K 31/4045* (2013.01); *A61K 31/4164* (2013.01); *A61K 31/4168* (2013.01); *A61K 31/4174* (2013.01); *A61K 31/439* (2013.01); *A61K 31/444* (2013.01); *A61K 31/4406* (2013.01); *A61K 31/4427* (2013.01); *A61K 31/4439* (2013.01); *A61K 31/465* (2013.01); *A61K 31/48* (2013.01); *A61K 31/498* (2013.01); *A61K 31/506* (2013.01); *A61K 31/538* (2013.01); *A61K 31/55* (2013.01); *A61K 31/675* (2013.01); *A61K 38/043* (2013.01); *A61K 45/06* (2013.01)

(58) Field of Classification Search
USPC .................................. 514/563, 570, 646, 653
See application file for complete search history.

(56) References Cited

U.S. PATENT DOCUMENTS

| | | | |
|---|---|---|---|
| 4,587,257 | A | 5/1986 | DeSantis et al. |
| 5,124,392 | A | 6/1992 | Robertson et al. |
| 5,212,196 | A | 5/1993 | House et al. |

(Continued)

FOREIGN PATENT DOCUMENTS

| | | |
|---|---|---|
| DE | 2040510 | 2/1972 |
| EP | 0160191 | 6/1985 |

(Continued)

OTHER PUBLICATIONS

Phillips (Treatment of experimental poly-D-lysine arthritis in rabbits by non-steroidal anti-inflammatory compounds, Agents and Action, vol. 11, 3 (1981), pp. 260-264).*
Kostamovaara (British Journal of Anaesthesia, Sep. 1998; 81; pp. 369-372).*
Katz (A comparisonof cocaine, lidocaind with epinephrine, and oxymetazoline for prevention of epistaxis on nasotracheal intubation, Journal of Clinical Anesthesia, vol. 2, issue 1, 1990, abstract only).*
Gyrn et al., "Intra-articular bupivacaine plus adrenaline for arthroscopic surgery of the knee," *Acta. Anaesthesiol. Scand.* 36:643-646 (1992).

(Continued)

*Primary Examiner* — Kathrien Cruz
(74) *Attorney, Agent, or Firm* — Tineka J. Quinton; Marcia S. Kelbon

(57) ABSTRACT

A method and solution for perioperatively inhibiting a variety of pain and inflammation processes during arthroscopic procedures. The solution preferably includes a vasoconstrictor that demonstrates substantial agonist activity at alpha adrenergic receptors and that is selected for peripheral (local) vasoconstriction and one or more additional pain and inflammation inhibitory agents at dilute concentration in a physiologic carrier, such as saline or lactated Ringer's solution. The solution is applied by continuous irrigation of a wound during a surgical procedure for peripheral vasoconstriction and inhibition of pain and/or inflammation while avoiding undesirable side effects associated with systemic application of larger doses of the agents.

44 Claims, 3 Drawing Sheets

(56) References Cited

U.S. PATENT DOCUMENTS

Figure 1:
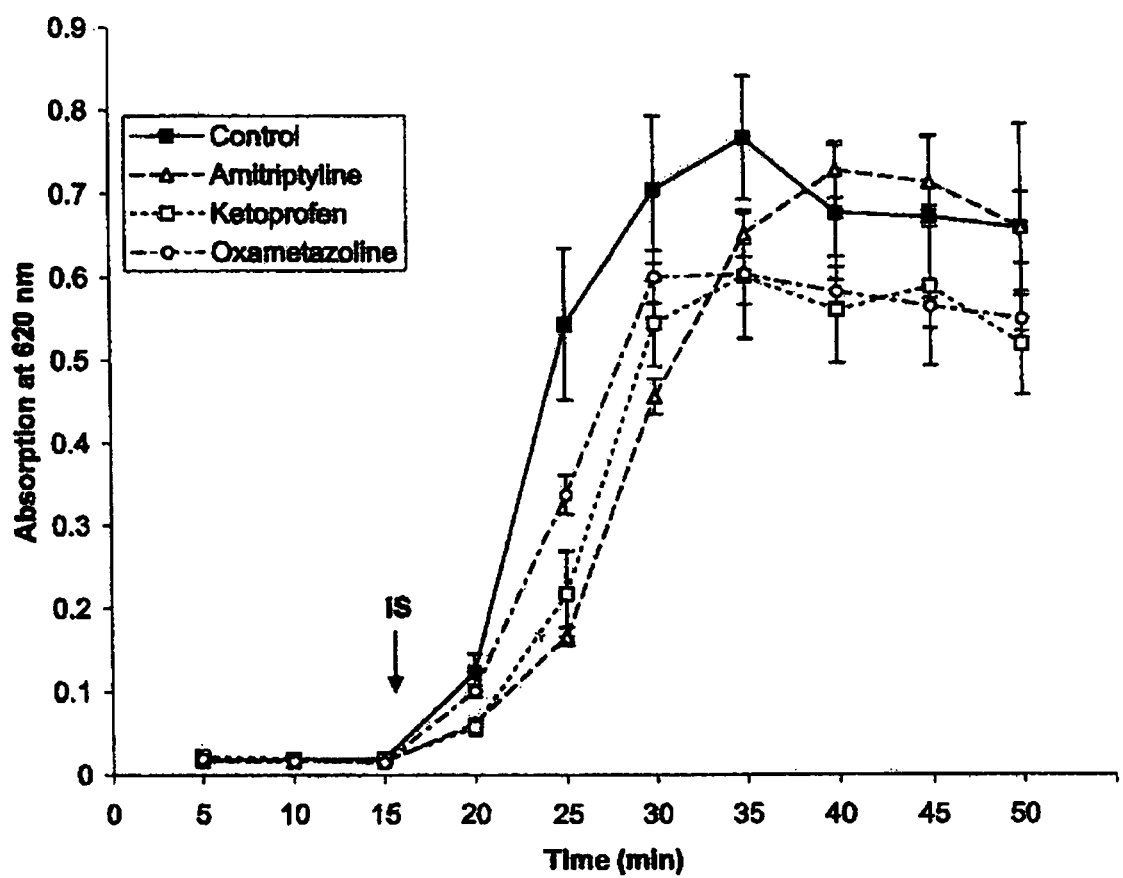

| | | | |
|---|---|---|---|
| 5,523,316 | A | 6/1996 | Gan et al. |
| 5,582,190 | A | 12/1996 | Slavin et al. |
| 5,624,893 | A | 4/1997 | Yanni |
| 5,756,503 | A | 5/1998 | Burke et al. |
| 5,767,105 | A | 6/1998 | Peyman |
| 5,800,385 | A | 9/1998 | Demopulos et al. |
| 5,811,446 | A | 9/1998 | Thomas |
| 5,820,583 | A | 10/1998 | Demopulos et al. |
| 5,843,016 | A | 12/1998 | Lugnani et al. |
| 5,860,950 | A | 1/1999 | Demopulos et al. |
| 5,942,241 | A | 8/1999 | Chasin et al. |
| 5,972,326 | A | 10/1999 | Galin et al. |
| 6,218,428 | B1 | 4/2001 | Chynn |
| 6,248,345 | B1 | 6/2001 | Goldenheim et al. |
| 6,261,279 | B1 | 7/2001 | Demopulos et al. |

FOREIGN PATENT DOCUMENTS

| | | |
|---|---|---|
| EP | 0166937 | 1/1986 |
| EP | 0424059 A1 | 4/1991 |
| EP | 0538469 A1 | 4/1993 |
| WO | WO 92/14453 | 9/1992 |
| WO | WO 92/17171 | 10/1992 |
| WO | WO 95/10280 | 4/1995 |
| WO | WO 95/16449 | 6/1995 |
| WO | WO 97/21445 | 6/1997 |
| WO | WO 98/38997 | 9/1998 |
| WO | WO 99/24023 | 5/1999 |
| WO | WO 00/38684 | 7/2000 |

OTHER PUBLICATIONS

Allen et al., "Postarthroscopy Analgesia With Intraarticular Bupivacaine/Morphine," *Anesthesiology* 79:475-480 (1993).
Massey et al., "Serum Lidocaine Levels During Arthroscopy Using Continuous Irrigation With Lidocaine," *Clin. Orthop.* 229:182-184 (1988).
Tsai et al., "Arthroscopic surgery of the knee in local anaesthesia," *Arch. Orthop. Trauma Surg.* 112:136-138 (1993).
Klein, "Tumescent Liposuction and Improved Postoperative Care Using Tumescent Liposuction Garments™," *Cosmetic Dermatology* 13:329-338 (1995).
Klein, "Tumescent Technique for Local Anesthesia Improves Safety in Large-Volume Liposuction," *Plast.Reconstr.Surg.* 92:1085-1098 (1993).
Klein et al., "The Tumescent Technique: Anesthesia and Modified Liposuction Technique," *Dermatologic Clinics* 8:425-437 (1990).
Badner et al., "Addition of Morphine to Intra-Articular Bupivacaine Does Not Improve Analgesia Following Knee Joint Replacement," *Regional Anesthesia* 22:347-350 (1997).
Debruyne et al., "Prilocaine in arthroscopy: Clinical pharmacokinetics and rational use," *Clin. Pharmacol. Ther.* 38:549-553 (1985).
Saunders et al., "Washout of local anesthetic during arthroscopy," *Arthroscopy* 4:90-92 (1988) (abstract only).
Wredmark et al., "Arthroscopy Under Local Anaesthesia Using Controlled Pressure-Irrigation with Prilocaine," *J.Bone Joint Surg. [Br.]* 64:583-585 (1982).
Pauwels et al., "Promotion of cell growth by stimulation of cloned human 5-HT1D receptor sites in transfected C6-glial cells is highly sensitive to intrinsic activity at 5-HT1D receptors," *Naunyn. Schmiedebergs. Arch. Pharmacol.* 354:136-144 (1996).
Noorily et al., "Intranasal anesthetic effects of lidocaine and tetracaine compared," *Otolaryngol. Head Neck Surg.* 113:370-374 (1995).
Noorily et al., "Cocaine, lidocaine, tetracaine: which is best for topical nasal anesthesia?" *Anesth. Analg.* 81:724-727 (1995).
Tschernko et al., "Clonidine added to the anesthetic solution enhances analgesia and improves oxygenation after intercostal nerve block for thoracotomy," *Anesth. Analg.* 87:107-111 (1998).
Taittonen et al., "Effect of clonidine and dexmedetomidine premedication on perioperative oxygen consumption and haemodynamic state," *British Journal of Anaesthesia* 78:400-406 (1997).

Corbett et al., "Intraocular adrenaline maintains mydriasis during cataract surgery," *Br. J. Ophthalmol.* 78:95-98 (1994) (abstract only).
Gaumann et al., "Hyperpolarizing afterpotentials in C fibers and local anesthetic effects of clonidine and lidocaine," *Pharmacology* 48:21-29 (1994).
Gillart et al., "Effects of Local Clonidine for Prolongation of Akinesia After Peribular Block," *Anesthesiology* 31:A941-A942 (1994).
Reinhart et al., "Postoperative analgesia after peripheral nerve block for podiatric surgery: clinical efficacy and chemical stability of lidocaine alone versus lidocaine plus clonidine," *Anesth. Analg.* 83:760-765 (1996).
Talke et al., "Effects of perioperative dexmedetomidine infusion in patients undergoing vascular surgery," *Anesthesiology* 82:620-633 (1995).
Kanto, "The place of alpha-2-agonists in anaesthesiology of today," *Acta. Anaesthesiol. Scand.* 41:4-5 (1997).
Pertovaara, "Antinociception induced by alpha-2-adrenoceptor agonists, with special emphasis on medetomidine studies," *Prog. Neurobiol.* 40:691-709 (1993).
Smith et al., "Monitored Anesthesia Care," *Int. Anesthesiol. Clin.* 32:99-112 (1994).
Ishiyama et al., "Mechanisms of dexmedetomidine-induced cerebrovascular effects in canine in vivo experiments," *Anesth. Analg.* 81:1208-1215 (1995).
Grond et al., "Inhibition of synovial plasma extravasation by preemptive administration of an antiinflammatory irrigation solution in the rat knee," *Anesth. Analg.* 92:1301-1306 (2001).
Ruffolo et al., "Receptor interactions of imidazolines. IX. Cirazoline is an alpha-1 adrenergic agonist and an alpha-2 adrenergic antagonist," *J. Pharmacol. Exp. Ther.* 222:29-36 (1982).
Willems et al., "Pharmacological evidence that alpha1-and alpha2-adrenoceptors mediate vasoconstriction of carotid arteriovenous anastomoses in anaesthetized pigs," *Br. J. Pharmacol.* 127: 1263-1271 (1999) (abstract only).
McCarthy et al., "Comparative neuropharmacology of dihydroergotamine and sumatriptan (GR 43175)," *Headache* 29:420-422 (1989) (abstract only).
Van den Berg et al., "Ergotism leading to threatened limb amputation or to death in two patients given heparin-dihydroergotamine prophylaxis," *Lancet* 1:955-956 (1982) (abstract only).
Rem et al., "Ergotism as complication of thromboembolic prophylaxis with heparin-dihydroergotamine," *Lancet* 1:219 (1987) (abstract only).
Malaquin et al., "Pleural and retroperitoneal fibrosis from dihydroergotamine," *N. Engl. J. Med.* 321:1760 (1989) (abstract only).
Kakkar, "Ergotism and heparin-dihydroergotamine," *Lancet* 2:96-97 (1982) (abstract only).
Aellig, "A new technique for recording compliance of human hand veins," *Br. J. Clin. Pharmacol.* 11:237-243 (1981) (abstract only).
Gentili et al., "Peripheral analgesic effect of intra-articular clonidine," *Pain* 64:593-596 (1996) (abstract only).
Bernard et al., "Postoperative analgesia by intravenous clonidine," *Anesthesiology* 75:577-582 (1991) (abstract only).
Motsch et al., "Addition of clonidine enhances postoperative analgesia from epidural morphine: a double-blind study," *Anesthesiology* 73:1067-1073 (1990) (abstract only).
De Kock et al., "Intravenous or epidural clonidine for intra- and postoperative analgesia," *Anesthesiology* 79:525-531 (1993) (abstract only).
Grace et al., "Postoperative analgesia after co-administration of clonidine and morphine by the intrathecal route in patients undergoing hip replacement," *Anesth. Analg.* 80:86-91 (1995) (abstract only).
De Kock et al., "Intraoperative clonidine enhances postoperative morphine patient-controlled analgesia," *Can. J. Anaesth.* 39:537-544 (1992) (abstract only).
Mogensen et al., "Epidural clonidine enhances postoperative analgesia from a combined low-dose epidural bupivacaine and morphine regimen," *Anesth. Analg.* 75:607-610 (1992).
Carabine et al., "Extradural clonidine infusions for analgesia after total hip replacement," *Br. J. Anaesth.* 68:338-443 (1992) (abstract only).

(56) References Cited

OTHER PUBLICATIONS

Gray et al., "Acute joint inflammation alters the adrenoceptor profile of synovial blood vessels in the knee joints of rabbits," *Ann. Rheum. Dis.* 51: 1129-1133 (1992).
Capogna et al., "Addition of clonidine to epidural morphine enhances postoperative analgesia after cesarean delivery," *Reg. Anesth.* 20:57-61.(1995) (abstract only).
Eisenach et al., "Epidural clonidine analgesia following surgery: phase I," *Anesthesiology* 71:640-646 (1989).
De Kock et al., "Epidural clonidine or sufentanil for intraoperative and postoperative analgesia," *Anesth. Analg.* 81:1154-1162 (1995) (abstract only).
Murphy et al., "Oxymetazoline inhibits adenylate cyclase by activation of serotonin-1 receptors in the OK cell, an established renal epithelial cell line," *Mol. Pharmacol.* 34:1-7 (1988) (abstract only).
Riegle et al., "Comparison of vasoconstrictors for functional endoscopic sinus surgery in children," *Laryngoscope* 102:820-823 (1992).
Lewis, "Effect of epinephrine on blood loss during liposuction," *Plast. Reconstr. Surg.* (letter to editor in) 90:136-138 (1992).
Anderhuber et al., "Plasma adrenaline concentrations during functional endoscopic sinus surgery," *Laryngoscope* 109:204-207 (1999).
Malhotra et al., "Comparison of the cardiovascular effects of 2.5% phenylephrine and 10% phenylephrine during ophthalmic surgery," *Eye* 12:973-975 (1998).
Dunlevy et al., "Optimal concentration of epinephrine for vasoconstriction in neck surgery," *Laryngoscope* 106:1412-1414 (1996).
Antcliff et al., "The maintenance of per-operative mydriasis in phacoemulsification with topical diclofenac sodium," *Eye* 11:389-391.
Muramatsu et al., "Alpha1-adrenoceptor subtypes and two receptor systems in vascular tissues," *Life Sci.* 62:1461-1465 (1998).
Costas-Gastiaburo et al., "Tonsillectomy and the value of peritonsillar infiltrations," *S. Afr. J. Surg.* 36:142-145 (1998) (abstract only).
Barret et al., "Effect of topical and subcutaneous epinephrine in combination with topical thrombin in blood loss during immediate near-total burn wound excision in pediatric burned patients," *Burns* 25:509-513 (1999) (abstract only).
Metaxotos et al., "The efficacy of bupivacaine with adrenaline in reducing pain and bleeding associated with breast reduction: a prospective trial," *Br. J. Plast. Surg.* 52:290-293 (1999) (abstract only).
Olszewski et al., "The effects of dilute epinephrine saline irrigation on the need for tourniquet use in routine arthroscopic knee surgery," *Am. J. Sports Med.* 27:354-356 (1999) (abstract only).
Karns, "Epinephrine-induced potentially lethal arrhythmia during arthroscopic shoulder surgery: a case report," *AANA. J.* 67:419-421 (1999) (abstract only).
Liou et al., "The effect of intracameral adrenaline infusion on pupil size, pulse rate, and blood pressure during phacoemulsification," *J. Ocul. Pharmacol. Ther.* 14:357-361 (1998) (abstract only).
Gimbel, "The effect of treatment with topical nonsteroidal anti-inflammatory drugs with and without intraoperative epinephrine on the maintenance of mydriasis during cataract surgery," *Ophthalmology* 96:585-588 (1989) (abstract only).
Asano et al., "Pial arteriolar constriction to alpha 2-adrenergic agonist dexmedetomidine in the rat," *Anesthesiology* 83:A153 (1995).
Tarver et al., "A comparison of cocaine vs. lidocaine with oxymetazoline for use in nasal procedures," *Otolaryngol. Head Neck Surg.* 109:653-659 (1993).
MacKenzie et al., "Local anesthetic update," *Anesth. Prog.* 40:29-34 (1993).
Munk et al., "Synthesis and evaluation of 2-[(5-methylbenz-1-ox-4-azin-6-yl)imino]imidazoline, a potent, peripherally acting alpha 2 adrenoceptor agonist," *J. Med. Chem.* 39: 3533-3538 (1996).
Chang et al., "The antiinflammatory action of guanabenz is mediated through 5-lipoxygenase and cyclooxygenase inhibition," *Eur. J. Pharmacol.* 142:197-205 (1987).

Flacke, "Alpha 2-adrenergic agonists in cardiovascular anesthesia," *J Cardiothorac. Vasc. Anesth.* 6:344-359 (1992).
Verma et al., "Alpha 2-adrenoceptor- and D2-dopamine receptor-mediated analgesic response of B-HT 920," *J. Pharm. Pharmacol.* 43:131-133 (1991).
Kulkarni et al., "Anti-inflammatory actions of clonidine, guanfacine and B-HT 920 against various inflammagen-induced acute paw oedema in rats," *Arch. Int. Pharmacodyn. Ther.* 279:324-334 (1986).
Thörig et al., "Effects of B-HT 920 in the eye and on regional blood flows in anaesthetized and conscious rabbits," *Curr. Eye Res.* 5:565-573 (1986).
Kyncl et al., "Novel adrenergic compounds. I. Receptor interactions of ABBOTT-54741 [(5,6-dihydroxy-1,2,3,4-tetrahydro-1-naphthtyl)imidazoline], an alpha-adrenergic agonist," *J. Cardiovasc. Pharmacol.* 13:382-391 (1989).
Boehringer Ingelheim—Roxane Laboratories, "Block another path of pain," *Duraclon Brochure* (1999).
Dillingham et al., "Medicated intra-articular solution used intraoperatively can decrease postoperative pain," *Anest. Analg.* (2000) (abstract only).
Jeon et al., "Pharmacological evaluation of UK-14,304 analogs at cloned human α-adrenergic receptors," *Bioorganic & Medicinal Chemistry Letters* 5: 2255-2258 (1995).
Lydiatt et al., "A prospective double-blind evaluation of cocaine, phenylephrine with xylocaine and oxymetazoline with xylocaine for topical intranasal use," *Amercian Journal of Rhinology* 3:105-112 (1989).
Tong et al., "α 2-adrenergic agonists," *New Drugs in Anesthesia: Part II* 12:49-63 (1994).
Ogren et al., "6B: Anesthesia for rhinoplasty," *Techniques of Regional Local Anesthesia for Specific Procedures* 51-53 (1993).
Bonnet et al., "Alpha 2 adrenergic agonists in pain management," *Session I—Practical Aspects and New Tendencies in RA* 10-16 (1997).
De Kock et al., "Intraoperative and postoperative analgesia using intravenous opioid, clonidine and lignocaine," *Anaesth. Intensive Care* 22:15-21 (1994) (abstract only).
van Essen et al., "Extradural clonidine does not potentiate analgesia produced by extradural morphine after meniscectomy," *Br. J. Anaesth.* 66:237-241 (1991) (abstract only).
Karaoglu et al., "Effects of Epinephrine in Local Anesthetic Mixtures on Hemodynamics and View Quality During Knee Arthroscopy," *Knee Surg. Sports Traumatol. Arthrosc.* 10:226-228 (2002).
Way, W.L., et al., "Narcotic Analgesics & Antagonists," in *Basic & Clinical Pharmacology*, Katzung, Bertram G., Editor, Lange Medical Publications, pp. 309-322 (1982).
Shearn, M.A., "Nonsteroidal Anti-inflammatory Agents; Nonopiate Analgesics; Drugs Used in Gout," *Basic & Clinical Pharmacology*, Katzung, Bertram G., Editor, Lange Medical Publications, pp. 369-386 (1982).
Kalso, Eija, et al., "Amitriptyline effectively relieves neuropathic pain following treatment of breast cancer," *Pain* 64:293-302 (1995).
Goodman, L.S., et al., "Analgesic-antipyretic and antiinflammatory agents," in *Goodman & Gilman's The Pharmacological Basis of Therapeutics*, Tenth Edition, Wonsiewicz, Martin J and Morriss, John M, eds., McGraw-Hill Publishing (2001).
Frank, R.G., et al., "Antidepressant Analgesia in Rheumatoid Arthritis," *J Rheumatol* 15:1632-1638 (1988).
Henslee, T.M., et al., "Vasoconstrictive Agents Commonly Used in Combination with Local Anesthetics: A Literature Review," *the Journal of Foot Surgery* 26(6):504-510 (1987).
Liou, Shiow-Wen, et al., "Maintenance of Mydriasis with One Bolus of Epinephrine Injection During Phacoemulsification," *J Ocular Pharmacol Ther* 17(3):249-253 (2001).
Katz, R.I., et at, "A comparions of cocaine, lidocaine with epinephrine, and oxymetazoline for prevention of epistaxis on nasotracheal intubation," *J Clin Anesth* 2:16-20 (1990).
Watson, M,G., et al., "Drug-indueed epistaxis?" *Journal of the Royal Society of Medicine* 83:162-164 (1990).

\* cited by examiner

ARTHROSCOPIC IRRIGATION SOLUTION AND METHOD FOR PERIPHERAL VASOCONSTRICTION AND INHIBITION OF PAIN AND INFLAMMATION

This application is a divisional of application Ser. No. 10/138,193 filed May 1, 2002, which is a continuation-in-part of application Ser. No. 09/839,633 filed Apr. 20, 2001, which is a continuation-in-part of International Application PCT/US99/24672 filed Oct. 20, 1999 designating the United States and that claims the benefit of the filing date of U.S. provisional application Ser. No. 60/105,029 filed Oct. 20, 1998, the benefit of the filing dates of which are hereby claimed under 35 U.S.C. §119 and §120.

I. FIELD OF THE INVENTION

The present invention relates to arthroscopic surgical irrigation solutions and methods, and particularly for anti-inflammatory, anti-pain and vasoconstrictive arthroscopic surgical irrigation solutions.

II. BACKGROUND OF THE INVENTION

Arthroscopy is a surgical procedure in which a camera, attached to a remote light source and video monitor, is inserted into an anatomic joint (e.g., knee, shoulder, etc.) through a small portal incision in the overlying skin and joint capsule. Through similar portal incisions, surgical instruments may be placed in the joint, their use guided by arthroscopic visualization. As arthroscopists' skills have improved, an increasing number of operative procedures, once performed by "open" surgical technique, now can be accomplished arthroscopically. Such procedures include, for example, partial meniscectomies and ligament reconstructions in the knee, shoulder acromioplasties and rotator cuff debridements and elbow synovectomies. As a result of widening surgical indications and the development of small diameter arthroscopes, wrist and ankle arthroscopies also have become routine.

Throughout each arthroscopy, physiologic irrigation fluid (e.g., normal saline or lactated Ringer's) is flushed continuously through the joint, distending the joint capsule and removing operative debris, thereby providing clearer intra-articular visualization. U.S. Pat. No. 4,504,493 to Marshall discloses an isomolar solution of glycerol in water for a non-conductive and optically clear irrigation solution for arthroscopy.

Alleviating pain and suffering in postoperative patients is an area of special focus in clinical medicine, especially with the growing number of out-patient operations performed each year. The most widely used agents, cyclooxygenase inhibitors (e.g., ibuprofen) and opioids (e.g., morphine, fentanyl), have significant side effects including gastrointestinal irritation/bleeding and respiratory depression. The high incidence of nausea and vomiting related to opioids is especially problematic in the postoperative period. Therapeutic agents aimed at treating postoperative pain while avoiding detrimental side effects are not easily developed because the molecular targets for these agents are distributed widely throughout the body and mediate diverse physiological actions. Despite the significant clinical need to inhibit pain and inflammation, methods for the delivery of inhibitors of pain and inflammation at effective dosages while minimizing adverse systemic side effects have not been developed. As an example, conventional (i.e., intravenous, oral, subcutaneous or intramuscular) methods of administration of opiates in therapeutic doses frequently is associated with significant adverse side effects, including severe respiratory depression, changes in mood, mental clouding, profound nausea and vomiting.

Prior studies have demonstrated the ability of endogenous agents, such as serotonin (5-hydroxytryptamine, sometimes referred to herein as "5-HT"), bradykinin and histamine, to produce pain and inflammation. Sicuteri, F., et al., *Serotonin-Bradykinin Potentiation in the Pain Receptors in Man*, Life Sci. 4, pp. 309-316 (1965); Rosenthal, S. R., *Histamine as the Chemical Mediator for Cutaneous Pain*, J. Invest. Dermat. 69, pp. 98-105 (1977); Richardson, B. P., et al., *Identification of Serotonin M-Receptor Subtypes and their Specific Blockade by a New Class of Drugs*, Nature 316, pp. 126-131 (1985); Whalley, E. T., et al., *The Effect of Kinin Agonists and Antagonists*, Naunyn-Schmiedeb Arch. Pharmacol. 36, pp. 652-57 (1987); Lang, E., et al., *Chemo-Sensitivity of Fine Afferents from Rat Skin In Vitro*, J. Neurophysiol. 63, pp. 887-901 (1990).

For example, 5-HT applied to a human blister base (denuded skin) has been demonstrated to cause pain that can be inhibited by $5-HT_3$ receptor antagonists. Richardson et al., (1985). Similarly, peripherally applied bradykinin produces pain that can be blocked by bradykinin receptor antagonists. Sicuteri et al., 1965; Whalley et al., 1987; Dray, A., et al., *Bradykinin and Inflammatory Pain*, Trends Neurosci. 16, pp. 99-104 (1993). Peripherally-applied histamine produces vasodilation, itching and pain that can be inhibited by histamine receptor antagonists. Rosenthal, 1977; Douglas, W. W., "Histamine and 5-Hydroxytryptamine (Serotonin) and their Antagonists", in Goodman, L. S., et al., ed., *The Pharmacological Basis of Therapeutics*, MacMillan Publishing Company, New York, pp. 605-638 (1985); Rumore, M. M., et al., *Analgesic Effects of Antihistaminics*, Life Sci 36, pp. 403-416 (1985). Combinations of these three agonists (5-HT, bradykinin and histamine) applied together have been demonstrated to display a synergistic pain-causing effect, producing a long-lasting and intense pain signal. Sicuteri et al., 1965; Richardson et al., 1985; Kessler, W., et al., *Excitation of Cutaneous Afferent Nerve Endings In Vitro by a Combination of Inflammatory Mediators and Conditioning Effect of Substance P*, Exp. Brain Res. 91, pp. 467-476 (1992).

In the body, 5-HT is located in platelets and in central neurons, histamine is found in mast cells, and bradykinin is produced from a larger precursor molecule during tissue trauma, pH changes and temperature changes. Because 5-HT can be released in large amounts from platelets at sites of tissue injury, producing plasma levels 20-fold greater than resting levels (Ashton, J. H., et al., *Serotonin as a Mediator of Cyclic Flow Variations in Stenosed Canine Coronary Arteries*, Circulation 73, pp. 572-578 (1986)), it is possible that endogenous 5-HT plays a role in producing postoperative pain, hyperalgesia and inflammation. In fact, activated platelets have been shown to excite peripheral nociceptors in vitro. Ringkamp, M., et al., *Activated Human Platelets in Plasma Excite Nociceptors in Rat Skin*, In Vitro, Neurosci. Lett. 170, pp. 103-106 (1994). Similarly, histamine and bradykinin also are released into tissues during trauma. Kimura, E., et al., *Changes in Bradykinin Level in Coronary Sinus Blood After the Experimental Occlusion of a Coronary Artery*, Am Heart J. 85, pp. 635-647 (1973); Douglas, 1985; Dray et al. (1993).

In addition, prostaglandins also are known to cause pain and inflammation. Cyclooxygenase inhibitors, e.g., ibuprofen, are commonly used in non-surgical and post-operative settings to block the production of prostaglandins, thereby reducing prostaglandin-mediated pain and inflammation. Flower, R. J., et al., *Analgesic-Antipyretics and Anti-Inflammatory Agents, Drugs Employed in the Treatment of Gout*, in Goodman, L. S., et al., ed., The Pharmacological Basis of Therapeutics, MacMillan Publishing Company, New York, pp. 674-715 (1985). Cyclooxygenase inhibitors are associated with some adverse systemic side effects when applied conventionally. For example, indomethacin or ketorolac have well recognized gastrointestinal and renal adverse side effects.

As discussed, 5-HT, histamine, bradykinin and prostaglandins cause pain and inflammation. The various receptors through which these agents mediate their effects on peripheral tissues have been known and/or debated for the past two decades. Most studies have been performed in rats or other animal models. However, there are differences in pharmacology and receptor sequences between human and animal species. There have been no studies conclusively demonstrating the importance of 5-HT, bradykinin or histamine in producing postoperative pain in humans.

Furthermore, antagonists of these mediators currently are not used for postoperative pain treatment. A class of drugs, termed 5-HT and norepinephrine uptake antagonists, which includes amitriptyline, has been used orally with moderate success for chronic pain conditions. However, the mechanisms of chronic versus acute pain states are thought to be considerably different. In fact, two studies in the acute pain setting using amitriptyline perioperatively have shown no pain-relieving effect of amitriptyline. Levine, J. D., et al., *Desipramine Enhances Opiate Postoperative Analgesia*, Pain 27, pp. 45-49 (1986); Kerrick, J. M., et al., *Low-Dose Amitriptyline as an Adjunct to Opioids for Postoperative Orthopedic Pain: a Placebo-Controlled Trial Period*, Pain 52, pp. 325-30 (1993). In both studies the drug was given orally. The second study noted that oral amitriptyline actually produced a lower overall sense of well-being in postoperative patients, which may be due to the drug's affinity for multiple amine receptors in the brain.

Amitriptyline, in addition to blocking the uptake of 5-HT and norepinephrine, is a potent 5-HT receptor antagonist. Therefore, the lack of efficacy in reducing postoperative pain in the previously-mentioned studies would appear to conflict with the proposal of a role for endogenous 5-HT in acute pain. There are a number of reasons for the lack of acute pain relief found with amitriptyline in these two studies. (1) The first study (Levine et al., 1986) used amitriptyline preoperatively for one week up until the night prior to surgery whereas the second study (Kerrick et al., 1993) only used amitriptyline postoperatively. Therefore, no amitriptyline was present in the surgical site tissues during the actual tissue injury phase, the time at which 5-HT is purported to be released. (2) Amitriptyline is known to be extensively metabolized by the liver. With oral administration, the concentration of amitriptyline in the operative site tissues may not have been sufficiently high for a long enough time period to inhibit the activity of postoperatively released 5-HT in the second study. (3) Since multiple inflammatory mediators exist, and studies have demonstrated synergism between the inflammatory mediators, blocking only one agent (5-HT) may not sufficiently inhibit the inflammatory response to tissue injury.

There have been a few studies demonstrating the ability of extremely high concentrations (1%-3% solutions—i.e., 10-30 mg per milliliter) of histamine$_1$ (H$_1$) receptor antagonists to act as local anesthetics for surgical procedures. This anesthetic effect is not believed to be mediated via H$_1$ receptors but, rather, due to a non-specific interaction with neuronal membrane sodium channels (similar to the action of lidocaine). Given the side effects (e.g., sedation) associated with these high "anesthetic" concentrations of histamine receptor antagonists, local administration of histamine receptor antagonists currently is not used in the perioperative setting.

III. SUMMARY OF THE INVENTION

The irrigation solutions of the present invention are dilute solutions including at least one adrenergic receptor agonist that demonstrates substantial agonist activity at alpha adrenergic receptors and that is selected for peripheral (local) vasoconstrictor activity, and one or more additional pain/inflammation inhibitory agents in a physiologic carrier. The invention also provides a method for perioperative delivery of the irrigation solution containing these agents directly to a surgical site, where it works locally at the receptor and enzyme levels to preemptively limit pain and inflammation at the site. Due to the local perioperative delivery method of the present invention, a desired therapeutic effect can be achieved with lower doses of agents than are necessary when employing other methods of delivery (i.e., intravenous, intramuscular, subcutaneous and oral).

In a first embodiment, the adrenergic receptor agonist selected for use as the vasoconstrictor is an agonist that demonstrates interactions with at least one member of the alpha receptor subfamily and that may also interact with members of the beta receptor subfamily, and thus may be either an agonist that is non-selective for activity at alpha adrenergic receptors relative to beta adrenergic receptors (a "mixed alpha and beta agonist") or may be selective for activity at alpha adrenergic receptors relative to beta adrenergic receptors.

In a preferred embodiment, the alpha adrenergic receptor agonist selected for use as the vasoconstrictor is an agonist that is primarily selective for direct agonist activity at alpha receptors, and that has relatively minor interaction with beta adrenergic receptors (also referred to herein as "beta receptors" or "β receptors"). Agonists that are primarily selective for direct agonist activity at alpha receptors and that have relatively minor interaction with beta receptors ("α selective agonists") include agonists that (a) act primarily at $\alpha_1$-receptors ("$\alpha_1$-receptor selective agonists"), (b) act substantially at $\alpha_2$-receptors ("$\alpha_2$-receptor selective agonists"), or (c) act primarily at both $\alpha_1$-receptors and $\alpha_2$-receptors ("mixed $\alpha_1$ and $\alpha_2$ agonists").

More preferably, the alpha agonist selected for use in the present invention is a mixed $\alpha_1$ and $\alpha_2$ agonist, as long as such mixed agonist provides vasoconstriction at the target tissue. Most preferably, the alpha agonist selected for use in the present invention has agonist activity at both $\alpha_{2A}$-receptors and $\alpha_{1A}$-receptors with high potency at both $\alpha_{1A}$ and $\alpha_{2A}$-receptors, as long as such agonist provides vasoconstriction at the target tissue.

In one embodiment, the additional anti-pain/anti-inflammation agent(s) in the solution may include one or more agents selected from the following classes of receptor antagonists and agonists and enzyme activators and inhibitors, each class acting through a differing molecular mechanism of action for pain and/or inflammation inhibition: (1) serotonin receptor antagonists; (2) serotonin receptor agonists; (3) histamine receptor antagonists; (4) bradykinin receptor antagonists; (5) kallikrein inhibitors; (6) tachykinin receptor antagonists, including neurokinin$_1$ and neurokinin$_2$ receptor subtype antagonists; (7) calcitonin gene-related peptide (CGRP) receptor antagonists; (8) interleukin receptor antagonists; (9) inhibitors of enzymes active in the synthetic pathway for arachidonic acid metabolites, including (a) phospholipase inhibitors, including PLA$_2$ isoform inhibitors and PLC$_\gamma$ isoform inhibitors, (b) cyclooxygenase inhibitors, including non-selective cyclooxygenase inhibitors and cyclooxygenase-2 (COX-2) selective inhibitors, and (c) lipoxygenase inhibitors; (10) prostanoid receptor antagonists including eicosanoid EP-1 and EP-4 receptor subtype antagonists and thromboxane receptor subtype antagonists; (11) leukotriene receptor antagonists including leukotriene $B_4$ receptor subtype antagonists and leukotriene $D_4$ receptor subtype antagonists; (12) opioid receptor agonists, including μ-opioid, δ-opioid, and κ-opioid receptor subtype agonists; (13) purinoceptor agonists and antagonists including $P_{2X}$ receptor antagonists and $P_{2Y}$ receptor agonists; (14) adenosine triphosphate (ATP)-sensitive potassium channel openers; (15) mitogen-activated protein kinase (MAPK) inhibitors; (16) neuronal nicotinic acetylcholine receptor agonists; and (17) soluble receptors. Each of the above agents functions either as an anti-inflammatory agent and/or as an anti-nociceptive, i.e., anti-pain or analgesic, agent. The selection of agents from these classes of compounds is tailored for the particular application.

A preferred solution for use in the present invention includes (a) a cyclooxygenase inhibitor (most preferably a nonselective cyclooxygenase inhibitor that also acts to inhibit lipoxygenase), (b) a serotonin$_2$ antagonist and/or a histamine$_1$ antagonist (most preferably an agent that exhibits both of these functions) and (c) an alpha adrenergic receptor agonist as a peripheral vasoconstrictor (more preferably an alpha agonist that is highly selective for alpha receptors without substantial (relatively little or no) interaction with beta receptors, and most preferably that is a mixed alpha-1 and alpha-2 agonist).

The present invention also provides a method for manufacturing a medicament compounded as a dilute irrigation solution for use in continuously irrigating an operative site or wound during an operative procedure. The method entails dissolving in a physiologic electrolyte carrier fluid an α-receptor agonist selected for local vasoconstrictive activity, and one or more additional anti-pain/anti-inflammatory agents. The α-receptor agonist is included at a concentration of preferably no more than 300,000 nanomolar, and more preferably no more than 75,000 nanomolar, depending on the particular agent selected. Each additional anti-inflammatory and/or analgesic agent is included at a concentration of preferably no more than 100,000 nanomolar, and more preferably no more than 10,000 nanomolar, except for cyclooxygenase inhibitors, which may be required at larger concentrations of preferably no more than 500,000 nanomolar, and more preferably no more than 200,000, depending on the particular inhibitor selected.

The method of the present invention provides for the delivery of a dilute combination of multiple receptor antagonists and agonists and enzyme inhibitors and activators directly to a wound or operative site, during therapeutic or diagnostic procedures for the inhibition of pain and/or inflammation. Since the active ingredients in the solution are being locally applied directly to the operative tissues in a continuous fashion, the drugs may be used efficaciously at extremely low doses relative to those doses required for therapeutic effect when the same drugs are delivered orally, intramuscularly, subcutaneously or intravenously. As used herein, the term "local" encompasses application of a drug in and around a wound or other operative site, and excludes oral, subcutaneous, intravenous and intramuscular administration. The term "continuous" as used herein encompasses uninterrupted application, repeated application at frequent intervals (e.g., repeated boluses at frequent intervals intraprocedurally), and applications which are uninterrupted except for brief cessations such as to permit the introduction of other drugs or agents or procedural equipment, such that a substantially constant predetermined concentration is maintained locally at the wound or operative site.

The advantages of low dose applications of agents are three-fold. The most important is the absence of systemic side effects that often limit the usefulness of these agents. Additionally, the agents selected for particular applications in the solutions of the present invention are highly specific with regard to the mediators on which they work. This specificity is maintained by the low dosages utilized. Finally, the cost of these active agents per operative procedure is low.

The advantages of local administration of the agents via luminal irrigation or other fluid application are the following: (1) local administration guarantees a known concentration at the target site, regardless of interpatient variability in metabolism, blood flow, etc.; (2) because of the direct mode of delivery, a therapeutic concentration is obtained instantaneously and, thus, improved dosage control is provided; and (3) local administration of the active agents directly to a wound or operative site also substantially reduces degradation of the agents through extracellular processes, e.g., first- and second-pass metabolism, that would otherwise occur if the agents were given orally, intravenously, subcutaneously or intramuscularly. This is particularly true for those active agents that are peptides, which are metabolized rapidly. Thus, local administration permits the use of compounds or agents which otherwise could not be employed therapeutically. For example, some agents in the following classes are peptidic: bradykinin receptor antagonists; tachykinin receptor antagonists; opioid receptor agonists; CGRP receptor antagonists; and interleukin receptor antagonists. Local, continuous delivery to the wound or operative site minimizes drug degradation or metabolism while also providing for the continuous replacement of that portion of the agent that may be degraded, to ensure that a local therapeutic concentration, sufficient to maintain receptor occupancy, is maintained throughout the duration of the operative procedure.

Local administration of the solution perioperatively throughout a surgical procedure in accordance with the present invention produces a preemptive analgesic and/or anti-inflammatory effect. As used herein, the term "perioperative" encompasses application intraprocedurally, pre- and intraprocedurally, intra- and postprocedurally, and pre-, intra- and postprocedurally. To maximize the preemptive anti-inflammatory and/or analgesic effects, the solutions of the present invention are most preferably applied pre-, intra- and postoperatively. By occupying the target receptors or inactivating or activating targeted enzymes prior to the initiation of significant operative trauma locally, the agents of the present solution modulate specific pathways to preemptively inhibit the targeted pathologic process. If inflammatory mediators and processes are preemptively inhibited in accordance with the present invention before they can exert tissue damage, the benefit is more substantial than if given after the damage has been initiated.

Inhibiting more than one inflammatory or nociceptive mediator by application of the multiple agent solution of the present invention dramatically reduces the degree of inflammation and pain. In one embodiment, the irrigation solutions of the present invention include combinations of drugs, each solution acting on multiple receptors or enzymes. The drug agents are thus simultaneously effective against a combination of pathologic processes, including pain and inflammation. The action of these agents is considered to be synergistic, in that the multiple receptor antagonists and inhibitory agonists of the present invention provide a disproportionately increased efficacy in combination relative to the efficacy of the individual agents. The synergistic action of several of the agents of the present invention are discussed, by way of example, below in the detailed descriptions of those agents.

The solutions of the present invention may be suitably applied to both humans and non-human mammals. The methods and solutions of the present invention are preferably delivered locally and perioperatively to a wound during an arthroscopic procedure. As used hereafter, the term "wound", unless otherwise specified, is intended to include surgical wounds and operative/interventional sites.

In a further aspect of the invention, the solutions of the invention may also be locally and perioperatively delivered during open surgical procedures on joints of the extremities, including but not limited to total knee, hip, ankle, toe, shoulder, elbow, wrist and finger joint replacements, the placement of implants into joints of the extremities, and for other surgical procedures on an extremity. As used herein, "extremity" refers to anatomic structures of the leg, including the hip, or of the arm, including the shoulder.

In a still further aspect of the invention, the solutions of the present invention may also be used for perioperative local irrigation of surgical or operative/procedural sites during oral/dental surgery, ocular surgery or burn treatment procedures.

Used perioperatively, the solution should result in a clinically significant decrease in operative site pain and inflammation relative to currently-used irrigation fluids, thereby decreasing the patient's postoperative analgesic (i.e., opiate) requirement and, where appropriate, allowing earlier patient mobilization of the operative site. No extra effort on the part of the surgeon and operating room personnel is required to use the present solution relative to conventional irrigation fluids.

IV. BRIEF DESCRIPTION OF THE DRAWINGS

Figure 2:
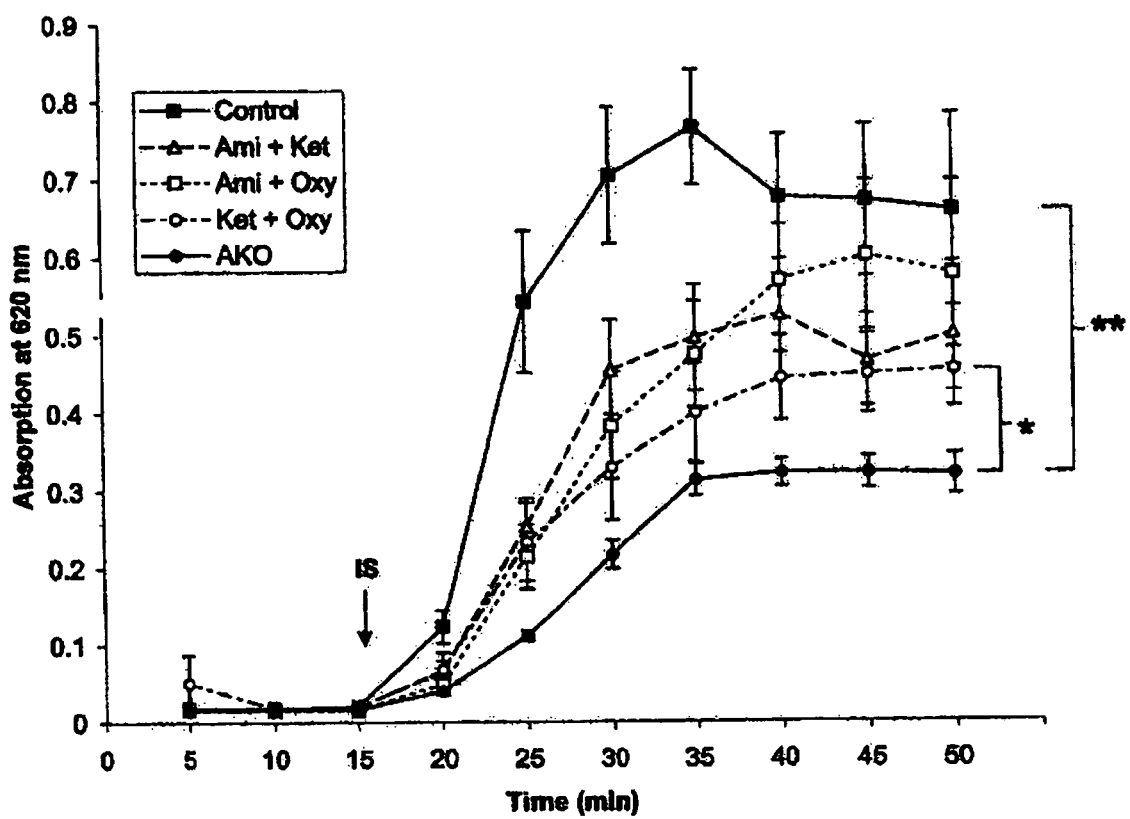
Figure 3:
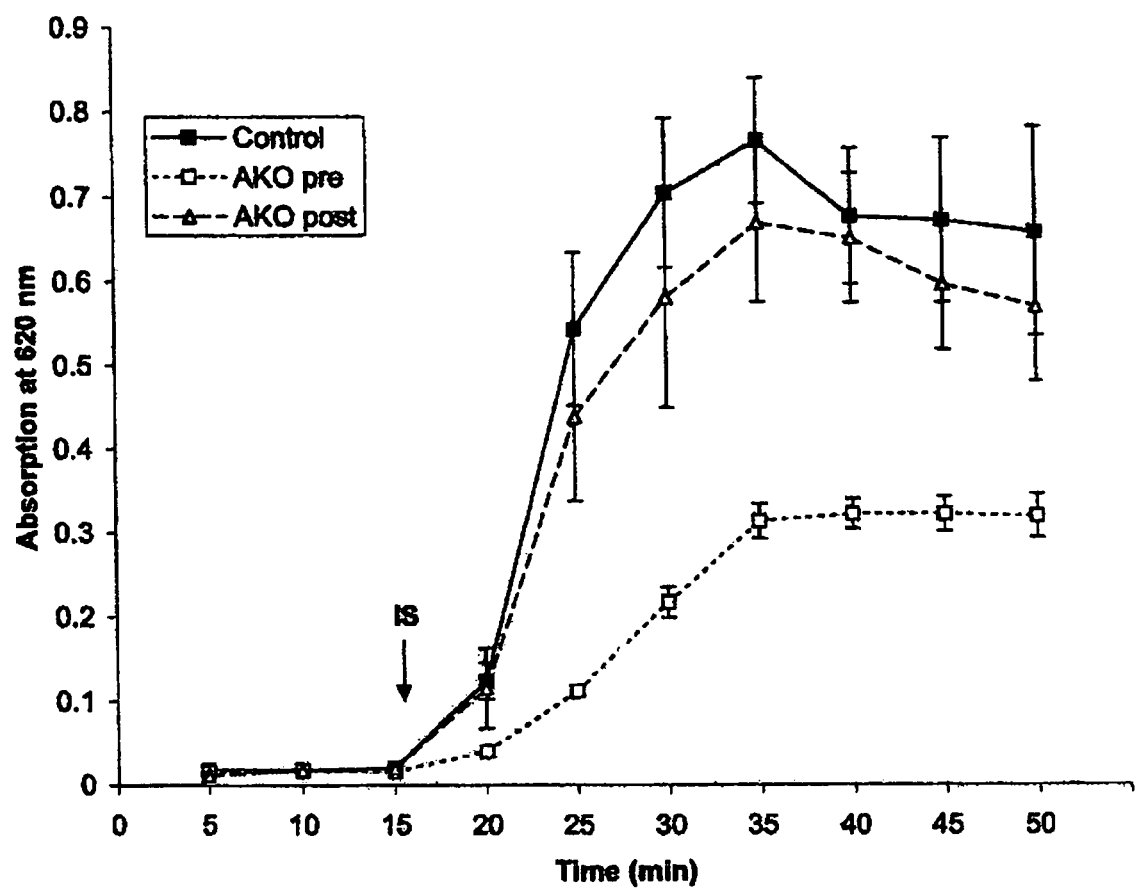

The present invention will now be described in greater detail, by way of example, with reference to the accompanying drawings in which:

FIGS. 1-3 provide charts showing the effects of agents that are suitable for use in a solution of the present invention on inflammatory solution-induced plasma extravasation in a rat knee joint model, as described in Example VI. FIGS. 1, 2 and 3 illustrate the effects of single agents, two agent combinations, and three agent combinations, respectively, as now described in greater detail.

FIG. 1 shows the effect of individual drugs on inflammatory solution (IS)-induced plasma extravasation. Baseline was established by perfusion with saline for 5 min followed by saline (control; n=16), amitriptyline (control; n=6), ketoprofen (control; n=6), or oxymetazoline (control; n=6), for 10 min. The inflammatory solution then was added to the perfusion fluid. Values are mean±SEM; n=number of knees.

FIG. 2 shows the effect of two-drug combinations and the three-drug combination on inflammatory solution-induced plasma extravasation. Baseline was established by perfusion with saline for 5 min followed by saline (control; n=16), amitriptyline+ketoprofen (Ami+Ket; n=6), amitriptyline+oxymetazoline (Ami+Oxy; n=6), ketoprofen+oxymetazoline (Ket+Oxy; n=6), or amitriptyline+ketoprofen+oxymetazoline (AKO; n=10) for 10 min. The inflammatory solution (IS) then was added to the perfusion fluid. Values are mean±SEM; n=number of knees. *P<0.0001 vs. control. **P<0.05 vs. Ket+Oxy.

FIG. 3 shows the effect of the three-drug combination (preemptive and post-inflammatory) on inflammatory solution-induced plasma extravasation. In the control (n=16), baseline was established by perfusion with saline for 15 min followed by the inflammatory solution (IS). In the preemptive group (AKO pre; n=10), saline was perfused for 5 min (baseline) and amitriptyline+ketoprofen+oxymetazoline for the next 10 min; then the inflammatory solution was added to the perfusion fluid. In the post-inflammatory group (AKO post; n=6), baseline was established by perfusion with saline for 15 min; then the inflammatory solution was started, followed by the addition of amitriptyline+ketoprofen+oxymetazoline after 10 min. Values are mean±SEM; n=number of knees.

V. DETAILED DESCRIPTION OF THE PREFERRED EMBODIMENT

The irrigation solutions of the present invention are dilute solutions including at least one adrenergic receptor agonist that demonstrates substantial agonist activity at alpha adrenergic receptors and that is selected for peripheral (local) vasoconstrictor activity, and one or more additional pain/inflammation inhibitory agents in a physiologic carrier. The carrier is a liquid, which as used herein is intended to encompass biocompatible solvents, suspensions, polymerizable and non-polymerizable gels, pastes and salves. Preferably the carrier is an aqueous solution that may include physiologic electrolytes, such as normal saline or lactated Ringer's solution.

In a first embodiment, the adrenergic receptor agonist selected for use as the vasoconstrictor is an agonist that demonstrates interactions with at least one member of the alpha receptor subfamily and that may also interact with members of the beta receptor subfamily, and thus may be either an agonist that is non-selective for activity at alpha adrenergic receptors relative to beta adrenergic receptors (a "mixed alpha and beta agonist") or may be selective for activity at alpha adrenergic receptors relative to beta adrenergic receptors.

In a preferred embodiment, the alpha adrenergic receptor agonist selected for use as the vasoconstrictor is an agonist that is primarily selective for direct agonist activity at alpha receptors, and that has relatively minor interaction with beta adrenergic receptors (also referred to herein as "beta receptors" or "β receptors").

Agonists that are primarily selective for direct agonist activity at alpha receptors and that have relatively minor interaction with beta receptors ("α selective agonists") include agonists that (a) act primarily at $\alpha_1$-receptors ("$\alpha_1$-receptor selective agonists"), (b) act primarily at $\alpha_2$-receptors ("$\alpha_2$-receptor selective agonists"), or (c) act substantially at both $\alpha_1$-receptors and $\alpha_2$-receptors ("mixed $\alpha_1$ and $\alpha_2$ agonists").

More preferably, the alpha agonist selected for use in the present invention is a mixed $\alpha_1$ and $\alpha_2$ agonist, as long as such mixed agonist provides vasoconstriction at the target tissue. Most preferably, the alpha agonist selected for use in the present invention has agonist activity at both $\alpha_{2A}$-receptors and $\alpha_{1A}$-receptors with high potency at both $\alpha_{1A}$ and $\alpha_{2A}$-receptors, as long as such agonist provides vasoconstriction at the target tissue.

When the α-receptor agonist selected for peripheral vasoconstrictor activity for use in the present invention has at least partial agonist activity at alpha-2 receptors, this vasoconstrictive agent may also function as an analgesic agent in the solution, and may play a role in inhibiting the vasodilation component of inflammation. These functions are dependent on agonist concentration and the local tissue receptor characteristics.

The one or more additional anti-inflammation/anti-pain agents are selected from the group consisting of: (1) serotonin receptor antagonists; (2) serotonin receptor agonists; (3) histamine receptor antagonists; (4) bradykinin receptor antagonists; (5) kallikrein inhibitors; (6) tachykinin receptor antagonists, including neurokinin, and neurokinin$_2$ receptor subtype antagonists; (7) calcitonin gene-related peptide (CGRP) receptor antagonists; (8) interleukin receptor antagonists; (9) inhibitors of enzymes active in the synthetic pathway for arachidonic acid metabolites, including (a) phospholipase inhibitors, including PLA$_2$ isoform inhibitors and PLCY isoform inhibitors, (b) cyclooxygenase inhibitors, including non-selective cyclooxygenase inhibitors and cyclooxygenase-2 (COX-2) selective inhibitors, and (c) lipoxygenase inhibitors; (10) prostanoid receptor antagonists including eicosanoid EP-1 and EP-4 receptor subtype antagonists and thromboxane receptor subtype antagonists; (11) leukotriene receptor antagonists including leukotriene B$_4$ receptor subtype antagonists and leukotriene D$_4$ receptor subtype antagonists; (12) opioid receptor agonists, including μ-opioid, δ-opioid, and κ-opioid receptor subtype agonists; (13) purinoceptor agonists and antagonists including P$_{2X}$ receptor antagonists and P$_{2Y}$ receptor agonists; (14) adenosine triphosphate (ATP)-sensitive potassium channel openers; (15) mitogen-activated protein kinase (MAPK) inhibitors; (16) neuronal nicotinic acetylcholine receptor agonists; and (17) soluble receptors.

In each of the surgical solutions of the present invention, the agents are included in low concentrations and are delivered locally in low doses relative to concentrations and doses required with conventional methods of drug administration to achieve the desired therapeutic effect. It is impossible to obtain an equivalent therapeutic effect by delivering similarly dosed agents via other (i.e., intravenous, subcutaneous, intramuscular or oral) routes of drug administration since drugs given systemically are subject to first- and second-pass metabolism. The concentration of each agent is determined in part based on its dissociation constant, $K_d$. As used herein, the term dissociation constant is intended to encompass both the equilibrium dissociation constant for its respective agonist-receptor or antagonist-receptor interaction and the equilibrium inhibitory constant for its respective activator-enzyme or inhibitor-enzyme interaction. Each agent is preferably included at a low concentration of 0.1 to 10,000 times $K_d$, except for cyclooxygenase inhibitors, which may be required at larger concentrations depending on the particular inhibitor selected. Preferably, each agent is included at a concentration of 1.0 to 1,000 times $K_d$ and most preferably at approximately 100 times $K_d$. These concentrations are adjusted as needed to account for dilution in the absence of metabolic transformation at the local delivery site. The exact agents selected for use in the solution, and the concentration of the agents, varies in accordance with the particular application, as described below.

In one embodiment, the surgical solutions constitute a novel therapeutic approach by combining multiple pharmacologic agents acting at distinct receptor and enzyme molecular targets. To date, pharmacologic strategies have focused on the development of highly specific drugs that are selective for individual receptor subtypes and enzyme isoforms that mediate responses to individual signaling neurotransmitters and hormones. This standard pharmacologic strategy, although well accepted, is not optimal since many other agents simultaneously may be responsible for initiating and maintaining inflammation and pain. Furthermore, despite inactivation of a single receptor subtype or enzyme, activation of other receptor subtypes or enzymes and the resultant signal transmission often can trigger a cascade effect. This explains the significant difficulty in employing a single receptor-specific drug to block a pathophysiologic process in which multiple transmitters play a role. Therefore, targeting only a specific individual receptor subtype, such as ET$_A$, is likely to be ineffective.

In contrast to the standard approach to pharmacologic therapy, the therapeutic approach of the present surgical solutions is based on the rationale that a combination of drugs acting simultaneously on distinct molecular targets is required to inhibit the full spectrum of events that underlie the development of a pathophysiologic state. Furthermore, instead of targeting a specific receptor subtype alone, the surgical solutions are composed of drugs that target common molecular mechanisms operating in different cellular physiologic processes involved in the development of pain and/or inflammation. In this way, the cascading of additional receptors and enzymes in the nociceptive and inflammatory pathways is minimized by the surgical solutions. In these pathophysiologic pathways, the surgical solutions inhibit the cascade effect both "upstream" and "downstream".

An example of "upstream" inhibition is the cyclooxygenase antagonists in the setting of pain and inflammation. The cyclooxygenase enzymes (COX$_1$ and COX$_2$) catalyze the conversion of arachidonic acid to prostaglandin H, which is an intermediate in the biosynthesis of inflammatory and nociceptive mediators including prostaglandins, leukotrienes, and thromboxanes. The cyclooxygenase inhibitors block "upstream" the formation of these inflammatory and nociceptive mediators. This strategy precludes the need to block the interactions of the seven described subtypes of prostanoid receptors with their natural ligands. A similar "upstream" inhibitor included in the surgical solutions is aprotinin, a kallikrein inhibitor. The enzyme kallikrein, a serine protease, cleaves the high molecular weight kininogens in plasma to produce bradykinins, important mediators of pain and inflammation. By inhibition of kallikrein, aprotinin effectively inhibits the synthesis of bradykinins, thereby providing an effective "upstream" inhibition of these inflammatory mediators. The surgical solutions also make use of "downstream" inhibitors to control the pathophysiologic pathways.

The agents included in the solutions of the present invention may be delivered in combination with other small molecule drugs, peptides, proteins, recombinant chimeric proteins, antibodies, or gene therapy vectors (viral and nonviral) to the spaces of the joint. The agents exert actions on any cells associated with the fluid spaces of the joint and structures comprising the joint, and which are involved in the normal function of the joint or are present due to a pathological condition. These cells and structures include, but are not limited to: synovial cells including both Type A fibroblast and type B macrophage cells; the cartilaginous components of the joint such as chondrocytes; cells associated with bone, including periosteal cells, osteoblasts, osteoclasts; the immunological components such as inflammatory cells including lymphocytes, mast cells, monocytes, eosinophils; and other cells like fibroblasts; and combinations of the above cell types.

A. Vasoconstrictors

The solutions of the present invention, and methods for delivering these solutions, utilize a vasoconstrictor delivered locally and perioperatively together with at least one, and preferably a combination, of additional agents that are inhibitors of inflammation or pain.

1. Rationale for Inclusion of a Vasoconstrictor

One rationale for including a vasoconstrictor agent is to increase the effectiveness of local drug delivery during arthroscopic surgery. The addition of a vasoconstrictor increases duration of action, decreases local bleeding and potentially decreases systemic toxic reactions. The ability to combine a vasoconstrictor with other anti-pain and anti-inflammatory agents in the perioperative setting provides several advantages, including potentially decreased analgesia and anti-inflammatory drug usage, and decreased surgical blood loss. Control of bleeding and improved visualization of the operative field is crucial to the outcome of endoscopic surgery. Certain operative procedures, such as arthroscopy of the knee, often employ the use of a tourniquet to minimize bleeding. The inclusion of the vasoconstrictor in the irrigation fluid may reduce the need for a tourniquet in such procedures. Using a vasoconstrictor agent reduces vascular uptake and delays clearance of the locally delivered drug combination, thus prolonging the anti-pain and anti-inflammatory effects. Furthermore, use of the vasoconstrictor has the potential to reduce peak blood plasma concentrations of the locally delivered combination of agents, thus enabling a higher maximum concentration of each drug to be delivered in the irrigation fluid without a concomitant increase in blood levels. In addition, because vasodilation is a well accepted component of inflammation, a vasoconstrictor can play a role in inhibiting this component of inflammation.

2. Adrenergic Receptor Agonists

Agonists that act on alpha adrenergic receptors exhibit vasoconstrictive activity. Certain types of adrenergic receptor agonists are suitable for use as vasoconstrictors in the solutions and methods of the present invention, for local perioperative delivery together with one or more anti-inflammatory or analgesic agents. Adrenergic receptor agonists that exhibit activity at both alpha and beta adrenergic receptors, e.g. epinephrine, have been demonstrated to have vasoconstrictive activity. Adrenergic receptor agonists that are selective for alpha-1 receptors are also known as having vasoconstrictive effects. Adrenergic receptor agonists that are selective for alpha-2 receptors are generally considered to have vasodilator effects. However, in some tissues exhibiting acute or chronic inflammation, such as in the knee, adrenergic receptor agonists that are active at alpha-2 receptors may have a vasoconstrictive effect. Adrenergic receptor agonists exhibiting at least partial agonist activity at alpha-2 receptors may also have analgesic and/or anti-inflammatory effects. In near-normal knees (for example), alpha-1 selective agonists may suitably be used as vasoconstrictors in the present invention. In knees (for example) exhibiting chronic or acute inflammation, or subject to surgical trauma, an agonist with alpha-2 activity or partial selectivity (e.g., mixed alpha-1 and alpha-2 agonists) may be preferred for use in the present invention, and such agonists will also provide analgesic and/or anti-inflammatory effect.

Before further describing the characteristics of preferred adrenergic agents, some background may be useful. All the individual nine receptors that comprise the adrenergic amine receptor family belong to the G-protein linked superfamily of receptors. The classification of the adrenergic family into three distinct subfamilies, namely $\alpha_1$, $\alpha_2$, and $\beta$, is based upon a wealth of binding, functional and second messenger studies. Each adrenergic receptor subfamily is itself composed of three homologous receptor subtypes that have been defined by cloning and pharmacological characterization of the recombinant receptors. Among adrenergic receptors in different subfamilies ($\alpha_1$ vs. $\alpha_2$ VS. $\beta$), amino acid identities in the membrane spanning domain range from 36-73%. However, between members of the same subfamily ($\alpha_{1A}$ vs. $\alpha_{1B}$) the identity between membrane domains is usually 70-80%. Together, these distinct receptor subtypes mediate the effects of two physiological agonists, epinephrine and norepinephrine.

Distinct adrenergic receptor types couple to unique sets of G-proteins and are thereby capable of activating different signal transduction effectors. The classification of $\alpha_1$, $\alpha_2$, and $\beta$ subfamilies not only defines the receptors with regard to signal transduction mechanisms, but also accounts for their ability to differentially recognize various natural and synthetic adrenergic amines. In this regard, a number of selective ligands have been developed and utilized to characterize the pharmacological properties of each of these receptor types. Functional responses of $\alpha_1$-receptors have been shown in certain systems to stimulate phosphatidylinositol turnover and promote the release of intracellular calcium (via $G_q$), while stimulation of $\alpha_2$-receptors inhibits adenylate cyclase (via $G_i$). In contrast, functional responses of $\beta$-receptors are coupled to increases in adenylate cyclase activity and increases in intracellular calcium (via $G_s$).

It is now accepted that there are three different $\alpha_1$ receptor subtypes which all exhibit a high affinity (subnanomolar) for the antagonist prazosin. The subdivision of $\alpha_1$-adrenoceptors into three different subtypes, designated $\alpha_{1A}$, $\alpha_{1B}$, and $\alpha_{1D}$, has been primarily based on extensive ligand binding studies of endogenous receptors and cloned receptors. Pharmacological characterization of the cloned receptors led to revisions of the original classification such that the clone originally called the $\alpha_{1C}$ subtype corresponds to the pharmacologically defined $\alpha_{1A}$ receptor. Agonist occupation of $\alpha_{1A-D}$-receptor subtypes results in activation of phospholipase C, stimulation of PI breakdown, generation of the $IP_3$ as second messenger and an increase in intracellular calcium.

Three different $\alpha_2$-receptor subtypes have been cloned, sequenced, and expressed in mammalian cells, referred to as $\alpha_{2A}$ ($\alpha_2$-C10), ($\alpha_{2B}$ ($\alpha_2$-C2), $\alpha_{2C}$ ($\alpha_2$-C4). These subtypes not only differ in their amino acid composition but also in their pharmacological profiles and distributions. An additional $\alpha_2$-receptor subtype, $\alpha_{2D}$ (gene rg20), was originally proposed based on radioligand binding studies of rodent tissues but is now considered to represent a species homolog to the human $\alpha_{2A}$-receptor.

Functionally, the signal transduction pathways are similar for all three $\alpha_{2A}$-receptor subtypes; each is negatively coupled to adenylate cyclase via $G_{i/o}$. In addition, the $\alpha_{2A}$ and $\alpha_{2B}$-receptors have also been reported to mediate activation of a G-protein coupled potassium channel (receptor-operated) as well as inhibition of a G-protein associated calcium channel.

Pharmacologically, $\alpha_2$-adrenergic receptors are defined as highly sensitive to the antagonists yohimbine (Ki=0.5-25 µM), atipamezole (Ki=0.5-2.5 µM), and idazoxan (Ki=21-35 µM) and with low sensitivity to the $\alpha_1$-receptor antagonist prazosin. Agonists selective for the $\alpha_2$-adrenergic receptor class relative to the $\alpha_1$-adrenergic receptor class are UK14304, BHT920 and BHT933. Oxymetazoline binds with high affinity and selectivity to the $\alpha_{2A}$-receptor subtype, but in addition binds with high affinity to $\alpha_1$-adrenergic receptors and 5HT1 receptors. An additional complicating factor is that $\alpha_2$-adrenergic receptor ligands that are imidazolines (clonidine, idazoxan) and others (oxymetazoline and UK14304) also bind with high affinity (nanomolar) to non-adrenoceptor imidazoline binding sites. Furthermore, species variation in the pharmacology of the $\alpha_{2A}$-adrenoceptor exists. To date, subtype-selective $\alpha_2$-adrenergic receptor ligands show only minimal selectivity or are nonselective with respect to other specific receptors, such that the therapeutic properties of subtype selective drugs are still under development.

3. Role of Alpha Receptors in the Regulation of Blood Flow

A study has been carried out to examine the effect of acute inflammation on the response of articular blood vessels in the knee joints of rabbits to adrenergic receptor agonists. Gray E, et al, Ann. Rheum. Dis., 51(10):1129-33 (1992). Acute joint inflammation was found to alter the response of articular blood vessels in the knee joints of rabbits to various adrenoceptor agonists. The responses to noradrenaline, phenylephrine, clonidine, UK-14304, and isoprenaline were examined 24 hours after intra-articular carrageenan injection and compared with those of normal animals. Antagonists specific for alpha-1 and alpha-2 receptors were used to identify the adrenergic receptors through which the responses were mediated, and to examine if carrageenan treatment altered the receptor response profile of these blood vessels. The study reported that, in the carrageenan treated animals, there is a reduction in the alpha-1 response with an associated increase in the alpha-2 response. A decrease in the number or affinity of alpha-1 adrenergic receptors is indicated by a shift to the right of the noradrenaline and phenylephrine dose/response-curves, whereas an increase in alpha-2 affinity or number is suggested by an associated leftward shift in the alpha-2 adrenoceptor agonist curves. This change in receptor response profile appears to arise as a direct result of carrageenan-induced joint inflammation. Clonidine, a mixed $\alpha_2$ and $\alpha_2$ agonist with greater $\alpha_2$ activity, nearly produced no response in normal animals, whereas in the inflammatory knee a distinct dose-dependent vasoconstriction was observed. Based on this study and similar studies, drugs possessing mixed $\alpha_2$ and $\alpha_1$ receptor selectivity profiles activate alpha-1 adrenergic receptors that mediate the vasoconstrictor response within synovial blood vessels of the normal knee, as well as alpha-2 receptors that become important in the injured or inflamed knee. While clonidine has weak alpha-1 activity, other mixed alpha-1 and alpha-2 agonists, such as oxymetazoline, will exhibit both significant alpha-1 and alpha-2 effect. In a near normal knee, a preferred agent for use in irrigation solutions will be an alpha-1 selective agent, or a mixed alpha-1 and alpha-2 agent with strong alpha-1 effect. However, a preferred agent to achieve vasoconstriction for use in arthroscopic irrigating solutions of the present invention, particularly for use in an injured knee with a pre-existing acute or chronic inflammatory state, may be a mixed alpha-1 and 2 receptor agonist having potent alpha-2 selective activity.

It has been shown that chronic inflammation may cause a reduction in sympathetic nerve-mediated vasoconstriction in rat knees. McDougall (Am J Physiol Regul Integr Comp Physiol, 281(3):R821-7 (2001)) studied the role of alpha-adrenergic receptors in regulating vasoactivity in chronically inflamed rat knee joints. To determine whether this phenomenon is due to an alteration in smooth muscle adrenoceptor function, the study compared the alpha-adrenoceptor profile of blood vessels supplying the anteromedial capsule of normal and chronically inflamed rat knee joints. The alpha-1 adrenoceptor agonists methoxamine and phenylephrine and the predominantly alpha-2 adrenoceptor agonist clonidine (0.1 ml bolus; dose range $10^{-12}$-$10^{-7}$ mol) were applied to exposed normal rat knees, resulting in a dose-dependent fall in capsular perfusion. One week after intra-articular injection of Freund's complete adjuvant (FCA) to induce chronic joint inflammation, the vasoconstrictor effects of methoxamine, phenylephrine, and clonidine were all significantly attenuated compared with normal controls. These changes may be due to an increase in sympathetic nerve hyperactivity that leads to a substantial increase in norepinephrine in the knee, resulting in vasoconstriction. Because norepinepherine acts on both alpha-1 and alpha-2 receptors, the continuous activation may lead to chronic sympathetic hyperactivity and down-regulation and/or desensitization of all alpha-receptors binding sites in the joint.

In summary, knee blood vessels possess vasoconstrictor tone due to basal activation of alpha-1 and alpha-2 receptors. Thus, both acute and chronic joint inflammation alter the alpha-1 and alpha-2 adrenergic receptor response profile, and this change in alpha-adrenergic pharmacologic responsiveness provides a rationale for the therapeutic advantage obtained using a mixed alpha agonist with significant alpha-2 agonist efficacy for irrigation associated with arthroscopic procedures following joint trauma.

A variety of other studies confirm that vasoconstrictive responses in the chronically inflamed knee are locally mediated by both vascular alpha-1 and -2 adrenergic receptors. A study of blood flow changes in response to selected alpha-1 and alpha-2 adrenoceptor agonists compared inflamed and untreated knee joints using the laser Doppler flowmetery (LDF) technique. Badavi, M. et al, Exp. Physiol., 85(1):49-55 (2000). Yohimbine (an alpha-2 antagonist) was injected (0.5 mg kg-1, I.P.) 30 min before phenylephrine application. Yohimbine blocked the vasoconstrictor effect of $10^{-10}$-$10^{-7}$ molar clonidine (topical application) by 44-67.7% inhibition. Prazosin (an alpha1 antagonist) blocked the vasoconstrictor effect of phenylephrine ($10^{-10}$-$10^{-7}$ molar, topical application) effectively (42 to 69.8% inhibition). This study also confirms the need and therapeutic advantage of using a mixed alpha-1 and alpha-2 agonist.

4. Adrenergic Drug Selectivity

Drug selectivity is extremely important in relation to pharmacological effects mediated by drugs affecting the sympathetic nervous system and the vasculature. Selectivity of a drug is typically a concentration- or dose-dependent property of a particular drug. At high concentration, a so-called selective drug may stimulate more than one type of receptor(s). The concentration at which this loss of selectivity occurs is used as a measurement for this aspect of a drug's selectivity characteristics, and when comparing the selectivity of one drug to that of another, often is expressed as a ratio of each drug's $IC_{50}$ or $K_d$. For example, epinephrine stimulates the two main types of adrenergic receptors, alpha and beta, and the subtypes in each family. In this respect, epinephrine is a non-selective alpha and beta agonist.

The selectivity of a drug used as a vasoconstrictor in an arthroscopic surgical procedure not only affects its action in the joint, but also plays a role in the side-effects it produces elsewhere in the body on adrenergic receptors (e.g., the heart, lungs stomach, urinary bladder, ureter and uterus), to the extent that there is any systemic uptake of the drug. The chief vascular actions of epinephrine, a non-selective $\alpha$ and $\beta$ agonist, for example, are exerted on the smaller arterioles and precapillary sphincters, although veins and arteries also respond to the drug. Vascular beds vary in their response to the drug, depending on the rate of infusion, the dose, and the ratio of alpha to beta adrenergic receptor types and responses characteristic of the various vascular beds. Total peripheral vascular resistance may drop due to beta-2 receptor vasodilation action, which is opposed by vasoconstrictor action mediated through alpha receptors. While non-selective alpha and beta agonists are included within the invention, a vasoconstrictor drug possessing enhanced selectivity for alpha receptors relative to beta receptors would minimize beta mediated receptor responses, and thus is preferred for use in the present invention.

5. Pharmacology of Oxymetazoline

Oxymetazoline is an adrenergic receptor agonist that has high selectivity for alpha receptors relative to beta receptors, and is a preferred vasoconstrictive agent for use in the present invention. Oxymetazoline is relatively unique in its receptor selectivity profile and pharmacological efficacy and kinetic characteristics. Interestingly, it can be defined as a high affinity/low efficacy mixed alpha adrenergic agonist. In many tissues, it is a highly potent, partial agonist acting on alpha-2 receptors. Binding constants and activation constants for oxymetazoline are in the low nanomolar range for this receptor target. Among the alpha-2 receptor subtypes, oxymetazoline is specific in its interaction with the alpha-2A subtype. In addition, oxymetazoline also demonstrates alpha-1 receptor agonist activity, demonstrating specificity for the alpha1 subtypes. Unlike epinephrine, oxymetazoline does not interact with the beta-adrenergic receptor family. Within the adrenergic receptor family, oxymetazoline is a partial agonist at alpha-2A receptors and an agonist at alpha-1A receptors. Based upon binding affinities determined by competition at cloned alpha-1 subtype membrane preparations, oxymetazoline shows much higher affinity (selectivity) for the alpha-1A subtype compared to the alpha-1B and the alpha-1D subtypes.

The selectivity of alpha-2 receptor agonist mechanisms accounts for use of these agonists as vasoconstrictors. Oxymetazoline is preferable to epinephrine for use in the present invention because it is essentially free of beta receptor mediated effects, and through its vasoconstrictor activity, will have a significantly longer duration of action in prolonging the effectiveness of local drug delivery. Additionally, because oxymetazoline is highly water soluble, it is less able to cross the blood-brain barrier and is more likely to have effects on the periphery, which is desirable.

Among the many known alpha-2 agonists, oxymetazoline is relatively unique in its receptor specificity profile. For example, both clonidine and UK14303 (brimonidine) are non-subtype selective agonists among the members of the alpha-2 receptor family. Non-subtype selective alpha-2 agonists will have fewer side effects than a relatively selective alpha.2 agonist, such as apraclonidine (iodipine). Following injury and inflammation, the peripheral excitability of nociceptor nerve endings is attenuated by locally delivered alpha-2 agents due to a peripheral mechanism. Alpha-1 selective and beta selective agonists do not mimic the anti-nociceptive property inherent in alpha-2 agonists.

In addition, there also is evidence for interaction of oxymetazoline at an imidazoline binding site or sites in various tissues based upon radioligand binding studies. The signal transduction pathway and the endogenous ligand for the putative one or more imidazoline receptors remains speculative since the imidazoline receptors are not yet fully characterized. It appears that imidazolines, such as oxymetazoline, may interact with both types of receptors, namely the alpha adrenergic receptors and the imidazoline receptor. Other drugs, such as clonidine and cirazoline share this dual receptor specificity, and such drugs are suitable vasoconstrictors for use in the present invention. Clonidine is an alpha-2 receptor agonist with some alpha-1 agonist properties. While not wishing to be limited by theory, this may provide an additional basis for the activity associated with oxymetazoline's vasoconstrictive action.

Another advantage of oxymetazoline for use in the procedures of the present invention is its long duration of action after initial exposure to the tissue. This long duration of action does not depend upon the continued presence of the drug at therapeutic concentrations. Rather, it appears to be a result of the oxymetazoline-induced receptor desensitization. This property provides for continued action after the completion of the surgical procedure. For example, topical intranasal application of oxymetazoline results in constriction of dilated arterioles and reduction in nasal blood flow. Reigle, et al., Laryngoscope 102: 800-823, (1992). Following intranasal application of oxymetazoline solutions, local vasoconstriction occurs within 5-10 minutes and persists for 5-6 hours with a gradual decline over the ensuing 6 hours.

For purposes of therapeutic selectivity in intraoperative irrigation fluids, the high affinity/low efficacy properties of oxymetazoline could be important since high affinity/low efficacy agonists theoretically have a much greater potential for tissue selectivity. Kenakin studied the relative contribution of affinity and efficacy to the selectivity of action to oxymetazoline. Kenakin, Br. J. Pharmacol., 81(1):131-41 (1984). Oxymetazoline demonstrated a pronounced tissue selectivity, when compared to noradrenaline, by being a potent full agonist in rat anococcygeus muscle and a partial agonist in rat vas deferens. Schild analysis with phentolamine, corynanthine, prazosin and yohimbine indicated no alpha-adrenoceptor heterogeneity within the rat anococcygeus muscle or between this tissue and rat vas deferens. Measurement of agonist $K_d$ values and Schild analysis of oxymetazoline's ability to inhibit the effects of noradrenaline (after alkylation) confirmed the homogeneity of alpha-adrenoceptors with respect to these two agonists. The above profiles of activity were predicted based upon modeling that oxymetazoline had a higher affinity but lower efficacy than noradrenaline. Experimentally, it was confirmed that oxymetazoline had 5 times the affinity but 0.2 to 0.3 times the efficacy of noradrenaline, thus defining its partial agonist activity in this tissue. It also behaves as a partial agonist in the rat aorta, producing only about 75% of the maximal response of phenylephrine.

Based on the above factors, suitable adrenergic receptor agonists for use in the present invention include both selective alpha agonists and non-selective alpha agonists (i.e., substantial agonist activity at both alpha and beta receptors). Suitable non-selective alpha agonists include epinephrine and norepinephrine, and exemplary concentrations (as delivered locally) for these agents when used as vasoconstrictors in the solutions of the present invention are provided in Table 1. While such non-selective alpha agonists are suitable for use in the invention, they are less preferred than agonists that are selective for alpha receptors relative to beta receptors.

Preferred alpha selective receptor agonists for use as vasoconstrictors in the present invention may include, depending on the application, alpha-1 selective agonists, alpha-2 selective agonists, and mixed alpha-1 and alpha-2 agonists. Suitable alpha-2 selective agonists are discussed below relative to their co-function of providing analgesic and potentially anti-inflammatory effects.

Suitable adrenergic receptor agonists for use in the present invention do not include dihydroergotamine, and as used herein the terms adrenergic receptor agonist, alpha receptor agonist, and subtypes thereof, are not intended to encompass dihydroergotamine. Dihydroergotamine, typically classified as a serotonin receptor agonist, also exhibits activity at alpha adrenergic receptors. However, dihydroergotamine is highly non-selective, also acting at dopaminergic, muscarinic and benzodiazepine receptors, and thus presents an elevated risk of undesirable or unintended effects, and highly non-specific agents are not preferred as vasoconstrictors for use in the present invention. In addition, dihydroergotamine potentially is highly toxic when delivered peripherally and, therefore, is even more undesirable for inclusion in the present invention.

Suitable alpha-1 selective agonists include phenylephrine, methoxamine and cirazoline, by way of example. Suitable concentrations (as delivered locally) for these agents when used as vasoconstrictors in the solutions of the present invention are provided in Table 1. Suitable mixed alpha-1 and alpha-2 agonists include, by way of example: oxymetazoline, p-aminoclonidine, naphazoline, tetrahydrozoline, anatazoline, tramazoline, monoxidine, apraclonidine (iopidine), guanfacine, guanabenz and xylazine. These and other mixed alpha-1 and alpha-2 agonists may be preferred for perioperative delivery during arthroscopic surgery on acute or chronically inflamed joints. Suitable concentrations (as delivered locally) for exemplary mixed alpha-1 and alpha-2 agonists when used as vasoconstrictors in the solutions of the present invention are also provided in Table 1.

pain and blockade of neurogenic inflammation. Sympathetic nervous system stimulation releases norepinephrine after tissue injury, and thus influences nociceptor activity. $\alpha_2$-receptor agonists, such as clonidine, can inhibit norepinephrine release at terminal nerve fiber endings and thus may induce analgesia directly at peripheral sites (without actions on the CNS). The ability of primary afferent neurons to release neurotransmitters from both their central and peripheral endings enables them to exert a dual, sensory and "efferent" or "local effector" function. The term, neurogenic inflammation, is used to describe the efferent function of the sensory nerves that includes the release of sensory neuropeptides that

TABLE 1

Exemplary Alpha-1 Selective and Mixed Alpha-1 and Alpha-2
Adrenergic Receptor Agonist Vasoconstrictors

| Compounds | Therapeutic Acceptable Concentrations (nM) | Therapeutic Efficient Concentrations (nM) | Preferred Concentrations (nM) | Most Preferred Concentration (nM) |
|---|---|---|---|---|
| Mixed $\alpha$-1/$\alpha$-2: | | | | |
| p-aminoclonidine | 0.002-200,000 | 0.01-50,000 | 0.1-10,000 | 10-2,000 |
| naphazoline | 0.002-200,000 | 0.01-50,000 | 0.1-10,000 | 100-10,000 |
| oxymetazoline | 0.001-100,000 | 0.01-25,000 | 0.05-15,000 | 5-10,000 |
| xylazine | 0.015-300,000 | 0.06-75,000 | 0.6-25,000 | 5-10,000 |
| $\alpha$-1 selective: | | | | |
| phenylephrine | 0.001-200,000 | 0.02-50,000 | 0.1-25,000 | 200-20,000 |
| cirazoline | 0.001-100,000 | 0.02-50,000 | 0.1-25,000 | 200-20,000 |
| methoxamine | 0.001-200,000 | 0.02-50,000 | 0.1-25,000 | 500-20,000 |
| Non-selective $\alpha$: | | | | |
| epinephrine | 0.001-200,000 | 0.02-50,000 | 0.1-25,000 | 1-5,000 |
| norepinephrine | 0.001-200,000 | 0.02-50,000 | 0.1-25,000 | 1,5000 |

B. Anti-Inflammatory and Analgesic Agents

The following is a description of exemplary suitable anti-inflammation/anti-pain agents for combination with a vasoconstrictor selected in accordance with the present invention. Preferably at least one anti-inflammation/anti-pain agent is selected that acts on a different receptor or molecular target than the selected vasoconstrictive agent. More preferably multiple anti-inflammation/anti-pain agents are selected, each acting on a different receptor or molecular target than the other anti-inflammation/anti-pain agent(s) and the selected vasoconstrictive agent in the solution. The exact agents selected for a given solution in accordance with the present invention will be determined by the application and the associated pain and inflammation actions. While not wishing to be limited by theory, the justification behind the selection of the various classes of agents that is believed to render the agents operative is also set forth.

1. Alpha-2 Adrenergic Receptor Agonists

Alpha receptor agonists have been discussed above with respect to their potential function as vasoconstrictive agents when applied locally in the setting of chronic or acute inflammation, an example of which is the local trauma associated with a surgical procedure. Alpha receptor agonists that are selective for alpha-2 receptors or having at least partial agonist activity at alpha-2 receptors also serve the dual function of being anti-pain/anti-inflammation agents. A therapeutic field in which $\alpha_2$-receptor agonists may be considered to have potential use is as an adjunct to anesthesia, for the control of contribute to the inflammatory process. Agents that induce the release of sensory neuropeptides from peripheral endings of sensory nerves, such as capsaicin, produce pain, inflammation and increased vascular permeability resulting in plasma extravasation. Drugs that block release of neuropeptides (substance P, CGRP) from sensory endings are predicted to possess analgesic and anti-inflammatory activity. This mechanism of action has been established for other drugs that exhibit analgesic and anti-inflammatory action in the periphery, such as sumatriptan and morphine, which act on 5HT1 and μ-opioid receptors, respectively. Both of these drugs are agonists that activate receptors that share a common mechanism of signal transduction with the $\alpha_2$-receptors. UK14304 (brimonidine), like sumatriptan, has been shown to block plasma extravasation within the dura mater through a prejunctional action on $\alpha_2$-receptors.

Evidence supporting a peripheral analgesic effect of clonidine was obtained in a study of the effect of intra-articular injection of the drug at the end of an arthroscopic knee surgery. Gentili, M et al Pain 64: 593-596 (1996). Clonidine is considered to exhibit nonopiate antinociceptive properties, which might allow its use as an alternative for postoperative analgesia. In a study undertaken to evaluate the analgesic effects of clonidine administered intravenously to patients during the postoperative period, clonidine was found to delay the onset of pain and decrease the pain score. Thus, a number of studies have demonstrated intra- and postoperative analgesia effects from drugs acting either at $\alpha_2$-adrenergic receptors, indicating these receptors are good therapeutic targets for new drugs to treat pain.

From the molecular and cellular mechanism of action defined for $\alpha_2$-receptor agonists, such as UK14304, these compounds are expected to exhibit anti-nociceptive action on the peripheral terminals of primary afferent nerves when applied intraoperatively in an irrigation solution directly to a tissue or a joint. In particular, an $\alpha_2$-receptor agonist is expected to be an effective drug delivered to a joint by an irrigation solution during an arthroscopic surgical procedure (periprocedurally). The $\alpha_2$-receptor agonist may be delivered alone, or in combination with other small molecule drugs, peptides, proteins, recombinant chimeric proteins, antibodies, or gene therapy vectors (viral and nonviral) to the fluid spaces of the joint. The $\alpha_2$-receptor agonist can exert its actions on any cells associated with the fluid spaces of the joint and structures comprising the joint and are involved in the normal function of the joint or are present due to a pathological condition. These cells and structures include, but are not limited to: synovial cells including both Type A fibroblast and type B macrophage cells; the immunological components such as inflammatory cells including lymphocytes, mast cells, monocytes, eosinophils; and other cells like fibroblasts and vascular endothelial cells; and combinations of the above.

$\alpha_2$-receptors agonists are suitable for use in the current invention, delivered locally and perioperatively either as a single agent or preferably in combination with other anti-pain and/or anti-inflammatory drugs, to inhibit pain and inflammation. Representative $\alpha_2$-receptors agonists for the practice of the present invention include, for example: clonidine; dexmedetomidine; oxymetazoline; ((R)-(–)-3'-(2-amino-1-hydroxyethyl)-4'-fluoro-methanesulfoanilide (NS-49); 2-[(5-methylbenz-1-$\alpha$-4-azin-6-yl)imino]imidazoline (AGN-193080); AGN 191103 and AGN 192172, as described in Munk, S. et al., *J. Med. Chem.* 39: 3533-3538 (1996); 5-bromo-N-(4,5-dihydro-1H-imidazol-2-yl)-6-quinoxalinamine (UK14304, brimonidine); 5,6,7,8-tetrahydro-6-(2-propenyl)-4H-thiazolo[4,5-d]azepin-2-amine (BHT920); 6-ethyl-5,6,7,8-tetrahydro-4H-oxaazolo[4,5-d]azepin-2-amine (BHT933), 5,6-dihydroxy-1,2,3,4-tetrahydro-1-naphyl-imidazoline (A-54741). Suitable concentrations for these agents when used in the present invention are set forth in Table 2.

nociceptive neurons in the periphery. Most researchers agree that 5-$HT_3$ receptors on peripheral nociceptors mediate the immediate pain sensation produced by 5-HT (Richardson et al., 1985). In addition to inhibiting 5-HT-induced pain, 5-$HT_3$ receptor antagonists, by inhibiting nociceptor activation, also may inhibit neurogenic inflammation. Barnes P. J., et al., *Modulation of Neurogenic Inflammation: Novel Approaches to Inflammatory Disease*, Trends in Pharmacological Sciences 11, pp. 185-189 (1990). A study in rat ankle joints, however, claims the 5-$HT_2$ receptor is responsible for nociceptor activation by 5-HT. Grubb, B. D., et al., *A Study of 5-HT-Receptors Associated with Afferent Nerves Located in Normal and Inflamed Rat Ankle Joints*, Agents Actions 25, pp. 216-18 (1988). Therefore, activation of 5-$HT_2$ receptors also may play a role in peripheral pain and neurogenic inflammation.

One goal of the solution of the present invention is to block pain and a multitude of inflammatory processes. Thus, 5-$HT_2$ and 5-$HT_3$ receptor antagonists are both suitably used, either individually or together, in the solution of the present invention, as shall be described subsequently. Amitriptyline (Elavil™) is a suitable 5-$HT_2$ receptor antagonist for use in the present invention. Amitriptyline has been used clinically for numerous years as an anti-depressant, and is found to have beneficial effects in certain chronic pain patients. Metoclopramide (Reglan™) is used clinically as an anti-emetic drug, but displays moderate affinity for the 5-$HT_3$ receptor and can inhibit the actions of 5-HT at this receptor, possibly inhibiting the pain due to 5-HT release from platelets. Thus, it also is suitable for use in the present invention.

Other suitable 5-$HT_2$ receptor antagonists include imipramine, trazodone, desipramine and ketanserin. Ketanserin has been used clinically for its anti-hypertensive effects. Hedner, T., et al., *Effects of a New Serotonin Antagonist, Ketanserin, in Experimental and Clinical Hypertension*, Am J of Hypertension, pp. 317s-23s (July 1988). Other suitable 5-$HT_3$ receptor antagonists include cisapride and ondansetron. Solution also may contain a serotonin$_{1B}$ (also known as serotonin$_{1D_\beta}$) antagonist. Suitable serotonin$_{1B}$ receptor antagonists include yohimbine, N-[-methoxy-3-(4-methyl-1-piperanzinyl)phenyl]-2'-methyl-4'-(5-methyl-1,2,4-oxadiazol-3-yl)[1,1-biphenyl]-4-carboxamide

TABLE 2

Exemplary Alpha-2 selective and Mixed Alpha-1 and Alpha-2 Adrenergic Receptor Agonist Vasoconstrictors and Anti-Pain/Inflammation Agents

| Compounds | Therapeutic Acceptable Concentrations (nM) | Therapeutic Efficient Concentrations (nM) | Preferred Concentrations (nM) | Most Preferred Concentration (nM) |
|---|---|---|---|---|
| clonidine | 0.002-200,000 | 0.01-50,000 | 0.1-10,000 | 10-2,000 |
| dexmedetomidine | 0.002-200,000 | 0.01-50,000 | 0.1-10,000 | 10-2,000 |
| UK14304 | 0.002-200,000 | 0.01-50,000 | 0.1-10,000 | 10-2,000 |
| oxymetazoline | 0.001-100,000 | 0.01-25,000 | 0.05-15,000 | 5-10,000 |
| NS-49 | 0.002-200,000 | 0.01-50,000 | 0.1-10,000 | 10-2,000 |
| AGN192172 | 0.005-100,000 | 0.1-25,000 | 1-5,000 | 10-1,000 |
| AGN193080 | 0.005-100,000 | 0.1-25,000 | 1-5,000 | 10-1,000 |
| AGN191103 | 0.002-200,000 | 0.1-25,000 | 1-5,000 | 10-1,000 |
| A-54741 | 0.002-200,000 | 0.1-50,000 | 1-10,000 | 10-2,000 |
| BHT920 | 0.003-200,000 | 0.3-50,000 | 3-30,000 | 30-5,000 |
| BHT933 | 0.003-200,000 | 0.3-50,000 | 3-30,000 | 30-5,000 |

2. Serotonin Receptor Antagonists

Serotonin (5-HT) is thought to produce pain by stimulating serotonin$_2$ (5-$HT_2$) and/or serotonin$_3$ (5-$HT_3$) receptors on ("GR127935") and methiothepin. Therapeutic and preferred concentrations for use of these drugs in the solution of the present invention are set forth in Table 3.

TABLE 3

Therapeutic and Preferred Concentrations of
Pain/Inflammation Inhibitory Agents

| Class of Agent | Therapeutic Concentrations (Nanomolar) | Preferred Concentrations (Nanomolar) |
|---|---|---|
| Serotonin$_2$ Receptor Antagonists: | | |
| Amitriptyline | 100-50,000 | 1,000-25,000 |
| imipramine | 0.1-1,000 | 50-500 |
| trazodone | 0.1-2,000 | 50-500 |
| desipramine | 0.1-1,000 | 50-500 |
| ketanserin | 0.1-1,000 | 50-500 |
| Serotonin$_3$ Receptor Antagonists: | | |
| tropisetron | 0.01-100 | 0.05-50 |
| metoclopramide | 10-10,000 | 200-2,000 |
| cisapride | 0.1-1,000 | 20-200 |
| ondansetron | 0.1-1,000 | 20-200 |
| Serotonin$_{1B}$ (Human 1D$_\beta$) Antagonists: | | |
| yohimbine | 0.1-1,000 | 50-500 |
| GR127935 | 0.1-1,000 | 10-500 |
| methiothepin | 0.1-500 | 1-100 |

3. Serotonin Receptor Agonists

5-HT$_{1A}$, 5-HT$_{1B}$ and 5-HT$_{1D}$ receptors are known to inhibit adenylate cyclase activity. Thus including a low dose of these serotonin$_{1A}$, serotonin$_{1B}$ and serotonin$_{1D}$ receptor agonists in the solution should inhibit neurons mediating pain and inflammation. The same action is expected from serotonin$_{1E}$ and serotonin$_{1F}$ receptor agonists because these receptors also inhibit adenylate cyclase.

Buspirone is a suitable 1A receptor agonist for use in the present invention. Sumatriptan is a suitable 1A, 1B, 1D and 1F receptor agonist. A suitable 1E receptor agonist is ergonovine. Therapeutic and preferred concentrations for these receptor agonists are provided in Table 4.

TABLE 4

Therapeutic and Preferred Concentrations of
Pain/Inflammation Inhibitory Agents

| Class of Agent | Therapeutic Concentrations (Nanomolar) | Preferred Concentrations (Nanomolar) |
|---|---|---|
| Serotonin$_{1A}$ Agonists: | | |
| buspirone | 1-1,000 | 10-200 |
| sumatriptan | 1-1,000 | 10-200 |
| Serotonin$_{1B}$ Agonists: | 1-1,000 | 10-200 |
| sumatriptan | | |
| Serotonin$_{1D}$ Agonists: | 10-2,000 | 100-1,000 |
| sumatriptan | | |
| Serotonin$_{1E}$ Agonists: | 10-2,000 | 100-1,000 |
| ergonovine | | |
| Serotonin$_{1F}$ Agonists: | 1-1,000 | 10-200 |
| sumatriptan | | |

4. Histamine Receptor Antagonists

Histamine receptors generally are divided into histamine$_1$ (H$_1$) and histamine$_2$ (H$_2$) subtypes. The classic inflammatory response to the peripheral administration of histamine is mediated via the H$_1$ receptor. Douglas, 1985. Therefore, the solution of the present invention preferably includes a histamine H$_1$ receptor antagonist. Promethazine (Phenergan™) is a commonly used anti-emetic drug, which potently blocks H$_1$ receptors, and is suitable for use in the present invention. Interestingly, this drug also has been shown to possess local anesthetic effects but the concentrations necessary for this effect are several orders higher than that necessary to block H$_1$ receptors, thus, the effects are believed to occur by different mechanisms. The histamine receptor antagonist concentration in the solution is sufficient to inhibit H$_1$ receptors involved in nociceptor activation, but not to achieve a "local anesthetic" effect, thereby eliminating the concern regarding systemic side effects.

Other suitable H$_1$ receptor antagonists include terfenadine, diphenhydramine, amitriptyline, mepyramine and tripolidine. Because amitriptyline is also effective as a serotonin$_2$ receptor antagonist, it has a dual inflammation/pain inhibitory function as used in the present invention. Suitable therapeutic and preferred concentrations for each of these H$_1$ receptor antagonists are set forth in Table 5.

TABLE 5

Therapeutic and Preferred Concentrations of
Pain/Inflammation Inhibitory Agents

| Class of Agent Histamine$_1$ Receptor Antagonists: | Therapeutic Concentrations (Nanomolar) | Preferred Concentrations (Nanomolar) |
|---|---|---|
| promethazine | 0.1-1,000 | 50-200 |
| diphenhydramine | 0.1-1,000 | 50-200 |
| amitriptyline | 0.1-1,000 | 50-500 |
| terfenadine | 0.1-1,000 | 50-500 |
| mepyramine (pyrilamine) | 0.1-1,000 | 5-200 |
| tripolidine | 0.01-100 | 5-20 |

5. Bradykinin Receptor Antagonists

Bradykinin receptors generally are divided into bradykinin$_1$ (B$_1$) and bradykinin$_2$ (B$_2$) subtypes. Studies have shown that acute peripheral pain and inflammation produced by bradykinin are mediated by the B$_2$ subtype whereas bradykinin-induced pain in the setting of chronic inflammation is mediated via the B$_1$ subtype. Perkins, M. N., et al., *Antinociceptive Activity of the Bradykinin B1 and B2 Receptor Antagonists, des-Arg$^9$, [Leu$^8$]-BK and HOE 140, in Two Models of Persistent Hyperalgesia in the Rat*, Pain 53, pp. 191-97 (1993); Dray, A., et al., *Bradykinin and Inflammatory Pain*, Trends Neurosci 16, pp. 99-104 (1993), each of which references is hereby expressly incorporated by reference.

At present, bradykinin receptor antagonists are not used clinically. These drugs are peptides (small proteins), and thus they cannot be taken orally, because they would be digested. Antagonists to B$_2$ receptors block bradykinin-induced acute pain and inflammation. Dray et al., 1993. B$_1$ receptor antagonists inhibit pain in chronic inflammatory conditions. Perkins et al., 1993; Dray et al., 1993. Therefore, depending on the application, the solution of the present invention preferably includes either or both bradykinin B$_1$ and B$_2$ receptor antagonists. For example, arthroscopy is performed for both acute and chronic conditions, and thus an irrigation solution for arthroscopy could include both B$_1$ and B$_2$ receptor antagonists.

Suitable bradykinin receptor antagonists for use in the present invention include the following bradykinin$_1$ receptor antagonists: the [des-Arg$^{10}$] derivative of D-Arg-(Hyp$^3$-Thi$^5$-D-Tic$^7$-Oic$^8$)-BK ("the [des-Arg$^{10}$] derivative of HOE 140", available from Hoechst Pharmaceuticals); and [Leu$^8$] des-Arg$^9$-BK. Suitable bradykinin$_2$ receptor antagonists include: [D-Phe$^7$]-BK; D-Arg-(Hyp$^3$-Thi$^{5,8}$-D-Phe$^7$)-BK ("NPC 349"); D-Arg-(Hyp$^3$-D-Phe$^7$)-BK ("NPC 567"); and D-Arg-(Hyp$^3$-Thi$^5$-D-Tic$^7$-Oic$^8$)-BK ("HOE 140"). These compounds are more fully described in the previously incorporated Perkins et al. 1993 and Dray et al. 1993 references. Suitable therapeutic and preferred concentrations are provided in Table 6.

TABLE 6

Therapeutic and Preferred Concentrations of Pain/Inflammation Inhibitory Agents

| Class of Agent | Therapeutic Concentrations (Nanomolar) | Preferred Concentrations (Nanomolar) |
|---|---|---|
| Bradykinin$_1$ Receptor Antagonists: | | |
| [Leu$^8$] des-Arg$^9$-BK | 1-1,000 | 50-500 |
| [des-Arg$^{10}$] derivative of HOE 140 | 1-1,000 | 50-500 |
| [leu$^9$] [des-Arg$^{10}$] kalliden | 0.1-500 | 10-200 |
| Bradykinin$_2$ Receptor Antagonists: | | |
| [D-Phe$^7$]-BK | 100-10,000 | 200-5,000 |
| NPC 349 | 1-1,000 | 50-500 |
| NPC 567 | 1-1,000 | 50-500 |
| HOE 140 | 1-1,000 | 50-500 |

6. Kallikrein Inhibitors

The peptide bradykinin is an important mediator of pain and inflammation, as noted previously. Bradykinin is produced as a cleavage product by the action of kallikrein on high molecular weight kininogens in plasma. Therefore kallikrein inhibitors are believed to be therapeutic in inhibiting bradykinin production and resultant pain and inflammation. A suitable kallikrein inhibitor for use in the present invention is aprotinin. Suitable concentrations for use in the solutions of the present invention are set forth below in Table 7.

TABLE 7

Therapeutic and Preferred Concentrations of Pain/Inflammation Inhibitory Agents

| Class of Agent Kallikrein Inhibitor: | Therapeutic Concentrations (Nanomolar) | Preferred Concentrations (Nanomolar) |
|---|---|---|
| Aprotinin | 0.1-1,000 | 50-500 |

7. Tachykinin Receptor Antagonists

Tachykinins (TKs) are a family of structurally related peptides that include substance P, neurokinin A (NKA) and neurokinin B (NKB). Neurons are the major source of TKs in the periphery. An important general effect of TKs is neuronal stimulation, but other effects include endothelium-dependent vasodilation, plasma protein extravasation, mast cell recruitment and degranulation and stimulation of inflammatory cells. Maggi, C. A., *Gen. Pharmacol.*, Vol. 22, pp. 1-24 (1991). Due to the above combination of physiological actions mediated by activation of TK receptors, targeting of TK receptors is a reasonable approach for the promotion of analgesia and the treatment of neurogenic inflammation.

a. Neurokinin$_1$ Receptor Subtype Antagonists

Substance P activates the neurokinin receptor subtype referred to as NK$_1$. Substance P is an undecapeptide that is present in sensory nerve terminals. Substance P is known to have multiple actions, which produce inflammation and pain in the periphery after C-fiber activation, including vasodilation, plasma extravasation and degranulation of mast cells. Levine, J. D., et al., *Peptides and the Primary Afferent Nociceptor*, J. Neurosci. 13, p. 2273 (1993). A suitable Substance P antagonist is ([D-Pro$^9$[spiro-gamma-lactam]Leu$^{10}$, Trp$^{11}$] physalaemin-(1-11)) ("GR 82334"). Other suitable antagonists for use in the present invention which act on the NK$_1$ receptor are: 1-imino-2-(2-methoxy-phenyl)-ethyl)-7,7-diphenyl-4-perhydroisoindolone(3aR,7aR) ("RP 67580"); and 2S,3S-cis-3-(2-methoxybenzylamino)-2-benzhydrylquinuclidine ("CP 96,345"). Suitable concentrations for these agents are set forth in Table 8.

TABLE 8

Therapeutic and Preferred Concentrations of Pain/Inflammation Inhibitory Agents

| Class of Agent Neurokinin$_1$ Receptor Subtype Antagonists | Therapeutic Concentrations (Nanomolar) | Preferred Concentrations (Nanomolar) |
|---|---|---|
| GR 82334 | 1-1,000 | 10-500 |
| CP 96,345 | 1-10,000 | 100-1,000 |
| RP 67580 | 0.1-1,000 | 100-1,000 | b. Neurokinin$_2$ Receptor Subtype Antagonists

Neurokinin A is a peptide which is co-localized in sensory neurons with substance P and which also promotes inflammation and pain. Neurokinin A activates the specific neurokinin receptor referred to as NK$_2$. Edmonds-Alt, S., et al., *A Potent and Selective Non-Peptide Antagonist of the Neurokinin A (NK$_2$) Receptor*, Life Sci. 50:PL101 (1992). Examples of suitable NK$_2$ antagonists include: ((S)—N-methyl-N-[4-(4-acetylamino-4-phenylpiperidino)-2-(3,4-dichlorophenyl) butyl]benzamide ("(±)-SR 48968"); Met-Asp-Trp-Phe-Dap-Leu ("MEN 10,627"); and cyc(Gln-Trp-Phe-Gly-Leu-Met) ("L 659,877"). Suitable concentrations of these agents are provided in Table 9.

TABLE 9

Therapeutic and Preferred Concentrations of Pain/Inflammation Inhibitory Agents

| Class of Agent Neurokinin$_2$ Receptor Subtype Antagonists: | Therapeutic Concentrations (Nanomolar) | Preferred Concentrations (Nanomolar) |
|---|---|---|
| MEN 10,627 | 1-1,000 | 10-1,000 |
| L 659,877 | 10-10,000 | 100-10,000 |
| (±)-SR 48968 | 10-10,000 | 100-10,000 |

8. CGRP Receptor Antagonists

Calcitonin gene-related peptide (CGRP) is a peptide which is also co-localized in sensory neurons with substance P, and which acts as a vasodilator and potentiates the actions of substance P. Brain, S. D., et al., *Inflammatory Oedema Induced by Synergism Between Calcitonin Gene-Related Peptide (CGRP) and Mediators of Increased Vascular Permeability*, Br. J. Pharmacol. 99, p. 202 (1985). An example of a suitable CGRP receptor antagonist is α-CGRP-(8-37), a truncated version of CGRP. This polypeptide inhibits the activation of CGRP receptors. Suitable concentrations for this agent are provided in Table 10.

TABLE 10

Therapeutic and Preferred Concentrations of Pain/Inflammation Inhibitory Agents

| Class of Agent CGRP Receptor Antagonist: | Therapeutic Concentrations (Nanomolar) | Preferred Concentrations (Nanomolar) |
|---|---|---|
| α-CGRP-(8-37) | 1-1,000 | 10-500 |

9. Interleukin Receptor Antagonist

Interleukins are a family of peptides, classified as cytokines, produced by leukocytes and other cells in response to inflammatory mediators. Interleukins (IL) may be potent hyperalgesic agents peripherally. Ferriera, S. H., et al., *Interleukin-1β as a Potent Hyperalgesic Agent Antagonized by a Tripeptide Analogue*, Nature 334, p. 698 (1988). An example of a suitable IL-1β receptor antagonist is Lys-D-Pro-Thr, which is a truncated version of IL-1β. This tripeptide inhibits the activation of IL-1β receptors. Suitable concentrations for this agent are provided in Table 11.

TABLE 11

Therapeutic and Preferred Concentrations of Pain/Inflammation Inhibitory Agents

| Class of Agent Interleukin Receptor Antagonist: | Therapeutic Concentrations (Nanomolar) | Preferred Concentrations (Nanomolar) |
|---|---|---|
| Lys-D-Pro-Thr | 1-1,000 | 10-500 |

10. Inhibitors of Enzymes Active in the Synthetic Pathway for Arachidonic Acid Metabolites a. Phospholipase Inhibitors

The production of arachidonic acid by phospholipase $A_2$ ($PLA_2$) results in a cascade of reactions that produces numerous mediators of inflammation, know as eicosanoids. There are a number of stages throughout this pathway that can be inhibited, thereby decreasing the production of these inflammatory mediators. Examples of inhibition at these various stages are given below.

Inhibition of the enzyme $PLA_2$ isoform inhibits the release of arachidonic acid from cell membranes, and therefore inhibits the production of prostaglandins and leukotrienes resulting in decreased inflammation and pain. Glaser, K. B., *Regulation of Phospholipase A2 Enzymes. Selective Inhibitors and Their Pharmacological Potential*, Adv. Pharmacol. 32, p. 31 (1995). An example of a suitable $PLA_2$ isoform inhibitor is manoalide. Suitable concentrations for this agent are included in Table 12. Inhibition of the phospholipase $C_\gamma$ ($PLC_\gamma$) isoform also will result in decreased production of prostanoids and leukotrienes, and, therefore, will result in decreased pain and inflammation. An example of a $PLC_\gamma$ isoform inhibitor is 1-[6-((17β-3-methoxyestra-1,3,5(10)-trien-17-yl)amino)hexyl]-1H-pyrrole-2,5-dione.

TABLE 12

Therapeutic and Preferred Concentrations of Pain/Inflammation Inhibitory Agents

| Class of Agent $PLA_2$ Isoform Inhibitor: | Therapeutic Concentrations (Nanomolar) | Preferred Concentrations (Nanomolar) |
|---|---|---|
| manoalide | 100-100,000 | 500-10,000 | b. Cyclooxygenase Inhibitors

Nonsteroidal anti-inflammatory drugs (NSAIDs) are widely used as anti-inflammatory, anti-pyretic, anti-thrombotic and analgesic agents. Lewis, R. A., *Prostaglandins and Leukotrienes*, In: Textbook of Rheumatology, 3d ed. (Kelley W. N., et al., eds.), p. 258 (1989). The molecular targets for these drugs are type I and type II cyclooxygenases (COX-1 and COX-2). These enzymes are also known as Prostaglandin H Synthase (PGHS)-1 (constitutive) and -2 (inducible), and catalyze the conversion of arachidonic acid to Prostaglandin H which is an intermediate in the biosynthesis of prostaglandins and thromboxanes. The COX-2 enzyme has been identified in endothelial cells, macrophages, and fibroblasts. This enzyme is induced by IL-1 and endotoxin, and its expression is upregulated at sites of inflammation. Constitutive activity of COX-1 and induced activity of COX-2 both lead to synthesis of prostaglandins which contribute to pain and inflammation.

i. Non-Selective Cyclooxygenase Inhibitors

NSAIDs currently on the market (diclofenac, naproxen, indomethacin, ibuprofen, etc.) are generally nonselective inhibitors of both isoforms of COX, but may show greater selectively for COX-1 over COX-2, although this ratio varies for the different compounds. Use of COX-1 and 2 inhibitors to block formation of prostaglandins represents a better therapeutic strategy than attempting to block interactions of the natural ligands with the seven described subtypes of prostanoid receptors. Reported antagonists of the eicosanoid receptors (EP-1, EP-2, EP-3) are quite rare and only specific, high affinity antagonists of the thromboxane A2 receptor have been reported. Wallace, J. and Cirino, G. *Trends in Pharm. Sci.*, Vol. 15 pp. 405-406 (1994).

The oral, intravenous or intramuscular use of cyclooxygenase inhibitors is contraindicated in patients with ulcer disease, gastritis or renal impairment. In the United States, the only available injectable form of this class of drugs is ketorolac (Toradol™), available from Syntex Pharmaceuticals, which is conventionally used intramuscularly or intravenously in postoperative patients but, again, is contraindicated for the above-mentioned categories of patients. The use of ketorolac, or any other cyclooxygenase inhibitor(s), in the solution in substantially lower dosages than currently used perioperatively may allow the use of this drug in otherwise contraindicated patients. The addition of a cyclooxygenase inhibitor to the solutions of the present invention adds a distinct mechanism for inhibiting the production of pain and inflammation during arthroscopy or other therapeutic or diagnostic procedure.

Another cyclooxygenase inhibitor suitable for use in the present invention to inhibit pain and inflammation is ketoprofen. Ketoprofen is a non-selective COX inhibitor, and is also reported to have an additional mechanism of action, namely the inhibition of the lipoxygenase pathway. Ketoprofen's action on COX-1 and COX-2 blocks the production of both prostaglandins and thromboxanes, and through action on 5-lipoxygenase, it is also expected to inhibit formation of leukotrienes and 5-HETE. Ketoprofen prevents the formation of both COX and lipoxygenase products (e.g., prostaglandins and leukotrienes, respectively) via inhibition of the release of arachidonic acid from phospholipid membranes. This dual mechanism of action may have therapeutic advantage, particularly in inflammatory pain states. Indeed, the efficacy of ketoprofen in a carrageenan model of inflammatory pain was greater than that obtained with other NSAIDs in the same experimental paradigm. Buritova, J., et al, Pain 6: 379-389 (1996); Honore P, et al, Pain 6: 365-375 (1995). Ketoprofen also exhibits high potency characterized in cellular and animal models of joint neuroinflammation, rapid onset kinetics characterized in experimental systems, and an absence of effects on cartilage metabolism. Ketoprofen's local anti-inflammatory action due to reduced synthesis of vasodilator prostaglandins (PGE2 and PGI2) also inhibits local vasodilatation and increased capillary permeability associated with the acute inflammatory response.

Preferred cyclooxygenase inhibitors for use in the present invention are ketoprofen, keterolac and indomethacin. Of these agents, ketoprofen is most preferred. Therapeutic and preferred concentrations for use in the solution are provided in Table 13.

TABLE 13

Therapeutic and Preferred Concentrations of Pain/Inflammation Inhibitory Agents

| Class of Agent Cyclooxygenase Inhibitors: | Therapeutic Concentrations (Nanomolar) | Preferred Concentrations (Nanomolar) |
| --- | --- | --- |
| ketorolac | 100-10,000 | 500-5,000 |
| indomethacin | 1,000-500,000 | 10,000-200,000 |
| Ketoprofen | 1,000-500,000 | 5,000-100,000 | ii. Cyclooxygenase-2 (COX-2) Inhibitors

As noted above, it is now appreciated that there are two forms of cyclooxygenase, termed cyclooxygenase-1 or type 1 (COX-1) and cyclooxygenase-2 or type 2 (COX-2). These isozymes are also known as Prostaglandin H Synthase (PGHS)-1 and PGHS-2, respectively. Both enzymes catalyze the conversion of arachidonic acid to unstable intermediates, $PGG_2$ and $PGH_2$, which are intermediates in the biosynthesis of prostaglandins and thromboxanes. COX-1 is present in platelets and endothelial cells and exhibits constitutive activity. COX-2 has been identified in endothelial cells, macrophages and fibroblasts, including synovial cells after treatment (induction) with cytokines.

The COX-2 isozyme is induced in settings of inflammation by cytokines and inflammatory mediators, such as IL-1, TNF-$\alpha$ and endotoxin, and its expression is upregulated at sites of inflammation. The large increase in activity of COX-2 above basal COX-1 activity concomitant with its upregulation, leads to synthesis of prostaglandins, which contribute to pain and inflammation. Because COX-2 is usually expressed only in inflamed tissue or after exposure to mediators of inflammation, selective inhibitors may exhibit anti-inflammatory activity without simultaneous effects on constitutively expressed COX-1 activity present in platelets and other cell types. This is considered to be a cause of undesirable side effects associated with certain usages of some nonselective NSAID drugs (e.g., clotting time, bleeding and ulceration).

It has been established that the two COX isozymes are pharmacologically distinct and therefore it has been possible to develop isozyme-specific (selective) cyclooxygenase inhibitors that are useful for anti-inflammatory therapy. A variety of biochemical, cellular and animal assays have been developed to assess the relative selectivity of inhibitors for the COX-1 and COX-2 isoforms. These assays include measurements of prostaglandin E2 production in microsomes prepared from various cell types and bioassay systems using intact human cells. For any given drug, despite experimental variation in the degree of selectivity noted among assay systems and between biological sources, compounds that are selective inhibitors for COX-2 have been identified. In general, a criteria for defining selectivity is the ratio of the COX-1/COX-2 inhibitory constants (or COX-2/COX-1) obtained for a given biochemical or cellular assay system. The selectivity ratio accounts for different absolute $IC_{50}$ values for inhibition of enzymatic activity that are obtained between microsomal and cellular assay systems (e.g. platelets and macrophages, cell lines stably expressing recombinant human COX isozymes).

Many of the conventional NSAIDs currently on the market (naproxen, indomethacin, ibuprofen) are generally nonselective inhibitors of both isoforms of COX, but may show greater selectively for COX-1 over COX-2, although this ratio varies for the different compounds. The use of a COX-2 inhibitor to block formation of prostaglandins represents a preferred therapeutic strategy rather than attempting to block interactions of the endogenous prostanoid ligands, (such as PGE2, which are produced by COX-2 at the inflammatory site, with any of the eight described subtypes of prostanoid receptors. This approach is not currently feasible since selective and potent antagonists for all of the prostanoid receptors (EP-1, EP-2, EP-3, EP-4, DP, FP, IP and TP) do not exist.

A study by Riendeau and coworkers compared the selectivity of more than 45 NSAIDs and selective COX-2 inhibitors using sensitive microsomal and platelet assays for the inhibition of human COX-1 based on the production of prostaglandin E2 by microsomes (Can J. Physiol. Pharmacol (1997) 75:1088-95). In this study, among the compounds that were reported to show selectivity for COX-2 vs. COX I, the rank order of potency was DuP 697>SC-58451, celecoxib>nimesulide=meloxicam=piroxicam=NS-398=RS-57067>SC-57666>SC-58125>flosulide>etodolac>L-745337>DFU-T-614, with $IC_{50}$ values ranging from 7 μM to 17 μM. A good correlation was obtained between the $IC_{50}$ values for the inhibition of microsomal COX-1 and both the inhibition of $TXB_2$ production by $Ca^{2+}$ ionophore challenged platelets and the inhibition of prostaglandin E2 production by CHO cells stably expressing human COX-1. The microsomal assay was more sensitive to inhibition than cell-based assays and allowed the detection of inhibitory effects on COX-1 for all NSAIDs and selective COX-2 inhibitors examined with discrimination of their potency under conditions of limited availability of arachidonic acid.

From the molecular and cellular mechanism of action defined for selective COX-2 inhibitors, such as celecoxib, as well as animal studies, these compounds are expected to exhibit anti-inflammatory action when applied intraoperatively in an irrigation solution directly to a tissue or a joint. In particular, it is expected to be an effective drug delivered by an irrigation solution during an arthroscopic procedure (periprocedural).

Representative examples of suitable COX-2 inhibitors for use in connection with the practice of the present invention include, without limitation: celecoxib, meloxicam, nimesulide, nimesulide, diclofenac, flosulide, N-[2-(cyclohexyloxy)-4-nitrophenyl]-methanesulfonamide (NS-398), 1-[(4-methylsulfonyl)phenyl]-3-trifluoromethyl-5-[(4-fluoro)phenyl]pyrazole (SC58125), and the following compounds as described in Riendeau, D. et al., (1997) *Can. J. Physiol. Pharmacol.* 75: 1088-95: DuP 697, SC-58451, RS-57067, SC-57666 and L-745,337. Representative dosage levels for administration in connection with the invention are listed in Table 14 below.

TABLE 14

Cyclooxygenase-2 Inhibitors

| Compounds | Therapeutic Acceptable Concentrations (nM) | Therapeutic Efficient Concentrations (nM) | Therapeutic Preferred Concentrations (nM) | Most Preferred Concentrations (nM) |
|---|---|---|---|---|
| DuP 697 | 0.01-50,000 | 0.05-15,000 | 0.3-3,000 | 3-500 |
| SC-58451 | 0.01-50,000 | 0.05-15,000 | 0.3-3,000 | 3-500 |
| celecoxib | 0.01-50,000 | 0.05-15,000 | 0.3-3,000 | 3-500 |
| meloxicam | 0.02-100,000 | 0.1-20,000 | 0.5-5,000 | 5-1,000 |
| nimesulide | 0.02-100,000 | 0.1-20,000 | 0.5-5,000 | 5-1,000 |
| diclofenac | 0.02-50,000 | 0.1-15,000 | 0.3-3,000 | 3-500 |
| NS-398 | 0.01-50,000 | 0.06-15,000 | 0.3-3,000 | 3-500 |
| L-745,337 | 0.01-150,000 | 0.04-50,000 | 0.2-10,000 | 2-2,000 |
| RS57067 | 0.01-150,000 | 0.04-50,000 | 0.2-10,000 | 2-2,000 |
| SC-58125 | 0.01-150,000 | 0.04-50,000 | 0.2-10,000 | 2-2,000 |
| SC-57666 | 0.01-150,000 | 0.04-50,000 | 0.2-10,000 | 2-2,000 |
| flosulide | 0.02-150,000 | 0.05-50,000 | 0.2-10,000 | 2-2,000 | c. Lipoxygenase Inhibitors

Inhibition of the enzyme lipoxygenase inhibits the production of leukotrienes, such as leukotriene $B_4$, which is known to be an important mediator of inflammation and pain. Lewis, R. A., *Prostaglandins and Leukotrienes*, In: Textbook of Rheumatology, 3d ed. (Kelley W. N., et al., eds.), p. 258 (1989). An example of a 5-lipoxygenase antagonist is 2,3,5-trimethyl-6-(12-hydroxy-5,10-dodecadiynyl)-1,4-benzoquinone ("AA 861"), suitable concentrations for which are listed in Table 15.

TABLE 15

Therapeutic and Preferred Concentrations of Pain/Inflammation Inhibitory Agents

| Class of Agent Lipoxygenase Inhibitor: | Therapeutic Concentrations (Nanomolar) | Preferred Concentrations (Nanomolar) |
|---|---|---|
| AA 861 | 100-10,000 | 500-5,000 |

11. Prostanoid Receptor Antagonists

Specific prostanoids produced as metabolites of arachidonic acid mediate their inflammatory effects through activation of prostanoid receptors. Examples of classes of specific prostanoid antagonists are the eicosanoid EP-1 and EP-4 receptor subtype antagonists and the thromboxane receptor subtype antagonists. A suitable prostaglandin $E_2$ receptor antagonist is 8-chlorodibenz[b,f][1,4]oxazepine-10(1H)-carboxylic acid, 2-acetylhydrazide ("SC 19220"). A suitable thromboxane receptor subtype antagonist is [15-[1α, 2β(5Z), 3β, 4α]-7-[3-[2-(phenylamino)-carbonyl]hydrazino]methyl]-7-oxobicyclo-[2,2,1]-hept-2-yl]-5-heptanoic acid ("SQ29548"). Suitable concentrations for these agents are set forth in Table 16.

TABLE 16

Therapeutic and Preferred Concentrations of Pain/Inflammation Inhibitory Agents

| Class of Agent Eicosanoid EP-1 Antagonist: | Therapeutic Concentrations (Nanomolar) | Preferred Concentrations (Nanomolar) |
|---|---|---|
| SC 19220 | 100-10,000 | 500-5,000 |

12. Leukotriene Receptor Antagonists

The leukotrienes ($LTB_4$, $LTC_4$, and $LTD_4$) are products of the 5-lipoxygenase pathway of arachidonic acid metabolism that are generated enzymatically and have important biological properties. Leukotrienes are implicated in a number of pathological conditions including inflammation. Specific antagonists are currently being sought by many pharmaceutical companies for potential therapeutic intervention in these pathologies. Halushka, P. V., et al., Annu. Rev. Pharmacol. Toxicol. 29: 213-239 (1989); Ford-Hutchinson, A. Crit. Rev. Immunol. 10:1-12 (1990). The $LTB_4$ receptor is found in certain immune cells including eosinophils and neutrophils. $LTB_4$ binding to these receptors results in chemotaxis and lysosomal enzyme release thereby contributing to the process of inflammation. The signal transduction process associated with activation of the $LTB_4$ receptor involves G-protein-mediated stimulation of phosphotidylinositol (PI) metabolism and elevation of intracellular calcium.

An example of a suitable leukotriene $B_4$ receptor antagonist is SC (+)-(S)-7-(3-(2-(cyclopropylmethyl)-3-methoxy-4-[(methylamino)-carbonyl]phenoxy-(propoxy)-3,4-dihydro-8-propyl-2H-1-benzopyran-2-propanoic acid ("SC 53228"). Concentrations for this agent that are suitable for the practice of the present invention are provided in Table 17. Other suitable leukotriene $B_4$ receptor antagonists include [3-[-2(7-chloro-2-quinolinyl)ethenyl]phenyl] [[3-(dimethylamino-3-oxopropyl)thio]methyl]thiopropanoic acid ("MK 0571") and the drugs LY 66,071 and ICI 20,3219. MK 0571 also acts as a $LTD_4$ receptor subtype antagonist.

TABLE 17

Therapeutic and Preferred Concentrations of
Pain/Inflammation Inhibitory Agents

| Class of Agent<br>Leukotriene B$_4$ Antagonist: | Therapeutic<br>Concentrations<br>(Nanomolar) | Preferred<br>Concentrations<br>(Nanomolar) |
|---|---|---|
| SC 53228 | 100-10,000 | 500-5,000 |

13. Opioid Receptor Agonists

Activation of opioid receptors results in anti-nociceptive effects and, therefore, agonists to these receptors are desirable. Opioid receptors include the μ-, δ- and κ-opioid receptor subtypes. The μ-receptors are located on sensory neuron terminals in the periphery and activation of these receptors inhibits sensory neuron activity. Basbaum, A. I., et al., *Opiate analgesia. How Central is a Peripheral Target?*, N. Engl. J. Med., 325:1168 (1991). δ- and κ-receptors are located on sympathetic efferent terminals and inhibit the release of prostaglandins, thereby inhibiting pain and inflammation. Taiwo, Y. O., et al., *Kappa-and Delta-Opioids Block Sympathetically Dependent Hyperalgesia*, J. Neurosci., Vol. 11, page 928 (1991). The opioid receptor subtypes are members of the G-protein coupled receptor superfamily. Therefore, all opioid receptor agonists interact and initiate signaling through their cognate G-protein coupled receptor. Examples of suitable μ-opioid receptor agonists are fentanyl and Try-D-Ala-Gly-[N-MePhe]-NH(CH$_2$)—OH ("DAMGO"). An example of a suitable δ-opioid receptor agonist is [D-Pen$^2$,D-Pen$^5$]enkephalin ("DPDPE"). An example of a suitable κ-opioid receptor agonist is (trans)-3,4-dichloro-N-methyl-N-[2-(1-pyrrolidnyl)cyclohexyl]-benzene acetamide ("U50,488"). Suitable concentrations for each of these agents are set forth in Table 18.

TABLE 18

Therapeutic and Preferred Concentrations of
Pain/Inflammation Inhibitory Agents

| Class of Agent | Therapeutic<br>Concentrations<br>(Nanomolar) | Preferred<br>Concentrations<br>(Nanomolar) |
|---|---|---|
| μ-Opioid Agonist: | | |
| DAMGO | 0.1-100 | 0.5-20 |
| sufentanyl | 0.01-50 | 1-20 |
| fentanyl | 0.1-500 | 10-200 |
| PL 017 | 0.05-50 | 0.25-10 |
| δ-Opioid Agonist: | | |
| DPDPE | 0.1-500 | 1.0-100 |
| κ-Opioid Agonist: | | |
| U50,488 | 0.1-500 | 1.0-100 |

14. Purinoceptor Antagonists and Agonists

Extracellular ATP acts as a signaling molecule through interactions with P$_2$ purinoceptors. One major class of purinoceptors are the P$_{2X}$ purinoceptors which are ligand-gated ion channels possessing intrinsic ion channels permeable to Na$^+$, K$^+$, and Ca$^{2+}$. P$_{2X}$ receptors described in sensory neurons are important for primary afferent neurotransmission and nociception. ATP is known to depolarize sensory neurons and plays a role in nociceptor activation since ATP released from damaged cells stimulates P$_{2X}$ receptors leading to depolarization of nociceptive nerve-fiber terminals. The P2X$_3$ receptor has a highly restricted distribution (Chen, C. C., et al., Nature, Vol. 377, pp. 428-431 (1995)) since it is selectively expressed in sensory C-fiber nerves that run into the spinal cord and many of these C-fibers are known to carry the receptors for painful stimuli. Thus, the highly restricted localization of expression for the P2X$_3$ receptor subunits make these subtypes excellent targets for analgesic action.

Suitable antagonists of P$_{2X}$/ATP purinoceptors for use in the present invention include, by way of example, suramin and pyridoxylphosphate-6-azophenyl-2,4-disulfonic acid ("PPADS"). Suitable concentrations for these agents are provided in Table 19.

Agonists of the P$_{2Y}$ receptor, a G-protein coupled receptor, are known to effect smooth muscle relaxation through elevation of inositol triphosphate (IP$_3$) levels with a subsequent increase in intracellular calcium. An example of a P$_{2Y}$ receptor agonist is 2-me-S-ATP.

TABLE 19

Therapeutic and Preferred Concentrations of
Pain/Inflammation Inhibitory Agents

| Class of Agent<br>Purinoceptor Antagonists: | Therapeutic<br>Concentrations<br>(Nanomolar) | Preferred<br>Concentrations<br>(Nanomolar) |
|---|---|---|
| suramin | 100-100,000 | 10,000-100,000 |
| PPADS | 100-100,000 | 10,000-100,000 |

15. Adenosine Triphosphate (ATP)-Sensitive Potassium Channel Openers

ATP-sensitive potassium channels have been discovered in numerous tissues, including vascular and non-vascular smooth muscle and brain, and binding studies using radiolabeled ligands have confirmed their existence. Opening of these channels causes potassium (K$^+$) efflux and hyperpolarizes the cell membrane. K$^+$ channel openers (KCOs) have been shown to prevent stimulus coupled secretion and are considered to act on prejunctional neuronal receptors and thus will inhibit effects due to nerve stimulation and release of inflammatory mediators. Quast, U., et al., *Cellular Pharmacology of Potassium Channel Openers in Vascular Smooth Muscle*, Cardiovasc. Res., Vol. 28, pp. 805-810 (1994).

Suitable ATP-sensitive K$^+$ channel openers for the practice of the present invention include: (−)pinacidil; cromakalim; nicorandil; minoxidil; N-cyano-N'-[1,1-dimethyl-[2,2,3,3-$^3$H]propyl]-N''-(3-pyridinyl)guanidine ("P 1075"); and N-cyano-N'-(2-nitroxyethyl)-3-pyridinecarboximidamide monomethansulphonate ("KRN 2391"). Concentrations for these agents are set forth in Table 20.

TABLE 20

Therapeutic and Preferred Concentrations of
Pain/Inflammation Inhibitory Agents

| Class of Agent<br>ATP-Sensitive K$^+$ Channel Opener: | Therapeutic<br>Concentrations<br>(Nanomolar) | Preferred<br>Concentrations<br>(Nanomolar) |
|---|---|---|
| cromakalim | 10-10,000 | 100-10,000 |
| nicorandil | 10-10,000 | 100-10,000 |
| minoxidil | 10-10,000 | 100-10,000 |
| P 1075 | 0.1-1,000 | 10-1,000 |
| KRN 2391 | 1-10,000 | 100-1,000 |
| (−)pinacidil | 1-10,000 | 100-1,000 |

16. MAP Kinase Inhibitors

The mitogen-activated protein (MAP) kinases are a group of protein serine/threonine kinases that are activated in response to a variety of extracellular stimuli and function in transducing signals from the cell surface to the nucleus. The MAP kinase cascade is one of the major signaling pathways that transmit signals from growth factors, hormones and inflammatory cytokines to intermediate early genes. In combination with other signaling pathways, these activated mitogen-activated protein-kinases (MAPKs) differentially alter the phosphorylation state and activity of transcription factors, and ultimately regulate cell proliferation, differentiation and cellular response to environmental stress. For example, MAPKs mediate the major signal transduction pathways from the potent inflammatory cytokine, IL-1, leading to induction of cyclooxygenase-2 (COX-2) in stimulated macrophages, acting through cis-acting factors involved in the transcriptional regulation of the COX-2 gene.

Signaling from some G-protein-coupled receptors also involves the MAPK cascade, inducing a variety of responses including cell proliferation, differentiation, and activation of several intracellular kinase cascades. Prominent among these kinases are the activation of MAP kinases, including the extracellular signal-regulated kinases (ERKs), ERK1 and ERK2 (p44MAPK and p42MAPK, respectively); stress-activated protein kinases (SAPKs/JNKs); and p38 MAP kinase (also known as stress-activated kinase (SAPK)-2, reactivating kinase and cytokine-suppressive binding protein). These receptors signal through heterotrimeric GTP-binding proteins (G-proteins). Recent data have shown that the activation of mitogen-activated protein/ERK kinase induced by G-protein-coupled receptors is mediated by both Gα and Gβγ subunits involving a common signaling pathway with receptor-tyrosine-kinases. Gβγ mediated mitogen-activated protein kinase activation is mediated by activation of phosphoinositide 3-kinase, followed by a tyrosine phosphorylation event, and proceeds in a sequence of events that involve functional association with the adaptor proteins Shc, Grb2, and Sos. Stress-activated protein kinases(SAPKs)/JNKs and p38 MAPK are able to be activated by Gβγ proteins in a pathway involving Rho family proteins including RhoA and Rac1.

A class of pyridinyl imidazoles inhibit p38 MAP kinase ((Lee, J. et al. (1994) Nature 372, 739-746)). Cuenda and coworkers (Cuenda, A. et al., (1995) FEBS Lett. 364, 229) showed that the compound, SB203580 [4-(4-fluorophenyl)-2-(4-methylsulfinylphenyl)-5-(4-pyridyl)-1H-imidazole] inhibited p38 in vitro (IC50=0.6 iM), suppressed the activation of MAPKAP kinase-2 and prevented the phosphorylation of heat shock protein (hsp) 27 in response to interleukin-1 (IL-1), cellular stresses and bacterial endotoxin in vivo. The specificity of SB203580 inhibitory action was demonstrated by its failure to inhibit 12 other protein kinases in vitro (including ERKs). SB 203580 has become useful for identifying the physiological roles and targets of p38 MAP kinase.

The role of p38 mitogen-activated protein kinase (MAPK) in biochemical inflammatory responses of human fibroblasts and vascular endothelial cells to IL-1 was investigated by use of SB203580, which specifically inhibits the enzyme. Actions of IL-1 that are selectively controlled by p38 MAPK are the regulation of prostaglandin H synthase-2 (also known as COX-2), metalloproteinases, and IL-6 at different levels. (Ridley S H et al. (1997) J. Immunol. 158:3165-73). SB203580 inhibited (50% inhibitory concentration approximately 0.5 μM) IL-1-induced phosphorylation of hsp 27 (an indicator of p38 MAPK activity) in fibroblasts without affecting the other known IL-1-activated protein kinase pathways (p42/p44 MAPK, p54 MAPK/c-Jun N-terminal kinase). In addition, SB203580 significantly inhibited IL-1-stimulated IL-6, (30 to 50% at 1 μM) but not IL-8 production from human fibroblasts (gingival and dermal) and umbilical vein endothelial cells. IL-1 induction of steady state level of IL-6 mRNA was not significantly inhibited, which is consistent with p38 MAPK regulating IL-6 production at the translational level.

Importantly, SB203580 strongly inhibited IL-1-stimulated prostaglandin production by fibroblasts and human umbilical vein endothelial cells. This was associated with the inhibition of the induction of COX-2 protein and mRNA. Since many cell types associated with inflammation, such as monocytes, endothelial cells and fibroblasts (including synovial) express the COX-2 gene at high levels upon activation by cytokines, extracellular stimuli and PGE2, the MAPK inhibitor is expected to exhibit anti-inflammatory activity against all of these cellular types. Inhibitors of p38 MAP kinase are potent in inhibiting PGE2 release, which will result in anti-inflammatory benefits.

MAPK inhibitors may also be effective as cartilage protective agents when applied locally to tissues of the joint in a variety of inflammatory or pathophysiological conditions. SB203580 was found to inhibit the stimulation of collagenase-1 and stromelysin-1 production by IL-1 without affecting synthesis of tissue inhibitor metalloproteinases (TIMP)-1. Furthermore, SB203580 prevented the increase in collagenase-1 and stromelysin-1 mRNA stimulated by IL-1. In a model of cartilage breakdown, short-term IL-1-stimulated proteoglycan resorption and inhibition of proteoglycan synthesis were unaffected by SB 203580, while longer term collagen breakdown was prevented.

p38 MAP kinase is involved in tumor necrosis factor (TNF)-induced cytokine expression and drugs which function as inhibitors of p38 MAP kinase activity block the production of proinflammatory cytokines, as described below (Beyaert, R. et al., EMBO J. 1996 15:1914-23). TNF treatment of cells activated the p38 MAPK pathway, as revealed by increased phosphorylation of p38 MAPK itself, activation of the substrate protein MAPKAP kinase-2, and phosphorylation of the heat shock protein 27 (hsp27). Pretreatment of cells with the p38 MAP kinase inhibitor SB203580 completely blocked this TNF-induced activation of MAPKAP kinase-2 and hsp27 phosphorylation. Under the same conditions, SB203580 also completely inhibited TNF-induced synthesis of IL-6 and expression of a reporter gene that was driven by a minimal promoter containing two NF-Kappa B elements. Thus, these studies show that the action of inhibitors, such as SB203580, on p38 MAPK interfere selectively with TNF- and IL-1 induced gene activation. SB 203580 has been evaluated in several animal models of cytokine inhibition and inflammatory disease. It was demonstrated to be a potent inhibitor of inflammatory cytokine production in vivo in both mice and rats with IC50 values of 15 to 25 mg/kg. SB 203580 possessed therapeutic activity in collagen-induced arthritis in DBA/LACJ mice with a dose of 50 mg/kg resulting in significant inhibition of paw inflammation and serum amyloid protein levels. Antiarthritic activity was also observed in adjuvant-induced arthritis in the Lewis rat when SB203580 was administered p.o. at 30 and 60 mg/kg. Additional evidence was obtained for beneficial effects on bone resorption with an IC50 of 0.6 μM.

A large number of inflammatory mediators have been implicated in producing synovitis of the joint, including arachidonic acid metabolites (particularly PGE2), vasoactive amines, and cytokines such as TNF-α, IL-1, IL-6 and neuropeptides. In fact, elevated levels of a number of these cytokines are found in the synovial fluid of acutely injured knee joints and remain elevated in patients for at least 4 weeks. These cytokines are produced locally in the joint from several activated cell types, including synovial fibroblasts, synovial macrophages, as well as chondrocytes.

In summary, a variety of biochemical, cellular and animal studies show that p38 MAPK plays an important role in the regulation of responses to IL-1, TNF-α and LPS and it is involved in the regulation of mRNA levels of some inflammatory-responsive genes, such as COX-2. Inhibitors of p38 MAPK block the production of proinflammatory cytokines as well as PGE2 and appear effective as anti-inflammatory drugs in animal models of arthritis and bone resorption.

Pain and hyperalgesia commonly associated with inflammatory conditions in the joint are in part due to activation of nociceptive sensory neurons in the joint by PGE2 released as a result of the inflammatory process. The ability of MAP kinase inhibitors to block the actions of key proinflammatory cytokines, such as IL-1 and TNF-α, will have downstream effects on many cell types in the joint (synovial fibroblasts and chondrocytes) thus inhibiting subsequent pathological effects such as infiltration of inflammatory cells into the joint, synovial hyperplasia, synovial cell activation, cartilage breakdown and inhibition of cartilage matrix synthesis. Thus, a MAPK inhibitor should block the propagation of the pain and inflammatory response by the aforementioned cytokines, and thereby interrupt the disease process.

From the molecular and cellular mechanism of action defined for MAP kinase inhibitors, such as SB203580, these compounds are expected to exhibit anti-inflammatory action when applied intraoperatively in an irrigation solution directly to a tissue or a joint.

Representative examples of MAPK inhibitor compounds suitable for the invention include, for example, 4-(4-fluorophenyl)-2-(4-methylsulfinylphenyl)-5-(4-pyridyl)-1H-imidazole (SB203580), 4-(3-Iodophenyl)-2-(4-methylsulfinylphenyl)-5-(4-pyridyl)-1H-imidazole (SB203580-iodo), 4-(4-fluorophenyl)-2-(4-hydroxyphenyl)-5-(4-pyridyl)-1H-imidazole (SB202190), 5-(2-amino-4-pyrimidyl)-4-(4-fluorophenyl)-1-(4-piperidinyl) imidazole (SB220025), 4-(4-fluorophenyl)-2-(4-nitrophenyl)-5-(4-pyridyl)-1H-imidazole (PD 169316), and 2'-amino-3'-methoxyflavone (PD98059). Representative useful dosages for these compounds are listed in the Table 21 below.

TABLE 21

MAP Kinase Inhibitors

| Compounds | Therapeutic Acceptable Concentrations (nM) | Therapeutic Efficient Concentrations (nM) | Therapeutic Preferred Concentrations (nM) | Most Preferred Concentrations (nM) |
|---|---|---|---|---|
| SB 203580 | 0.02-500,000 | 0.1-200,000 | 0.5-50,000 | 50-10,000 |
| SB 203580 iodo | 0.02-500,000 | 0.1-200,000 | 0.5-50,000 | 50-10,000 |
| SB 202190 | 0.01-500,000 | 0.05-100,000 | 0.2-20,000 | 20-5,000 |
| SB 220025 | 0.01-500,000 | 0.05-100,000 | 0.2-25,000 | 20-5,000 |
| PD 98059 | 0.01-500,000 | 0.04-50,000 | 0.1-10,000 | 10-2,000 |
| PD 169316 | 0.02-500,000 | 0.1-200,000 | 1-50,000 | 10-20,000 |

17. Neuronal Nicotinic Acetylcholine Receptor Agonists

Distinct receptor subtypes that comprise the nicotinic acetylcholine receptor (nAChR) family are found on skeletal muscle at the neuromuscular junction, within the brain and spinal cord, on sensory nerves and some peripheral nerve terminals. These receptors function as ligand-gated ion channels. Upon binding ligands that are agonists, nAChRs are transiently converted to an open channel state (active conformation), which allows cation influx and subsequent depolarization of the cell. Examples of ligands that function as agonists are the natural neurotransmitter, acetylcholine, its nonhydrolyzable analog, carbamylcholine, DMPP, epibatidine and anatoxin-a. Antagonist ligands include d-tubocurarine, and the snake venom α-neurotoxins, such as α-bungarotoxin. Invention compounds referred to as agonists include all ligands which can be functionally classified as partial (weak and strong) agonists and full agonists, thus encompassing the full spectrum of pharmacological agonist activity or efficacy based upon any method of measurement, including electrophysiological responses measured by voltage clamp technique, cellular or tissue based methods. Agonists defined by functional activity also include ligands that can act as allosteric modulators of neuronal nAChRs.

In the peripheral and central nervous systems, it is recognized that there is a molecular diversity of neuronal AChRs subtypes composed of pentameric oligomers from a multigene family containing at least 13 members ($\alpha_1$-$\alpha_9$, $\beta_2$-$\beta_5$). Molecular and biochemical approaches have allowed neuronal nAChR subunits to be classified as either subunits involved in binding of acetylcholine α-subunits) or structural subunits (termed either as non-α or as β). The acetylcholine binding subunits have been defined on the basis of adjacent cysteine residues (Cys 192 and 193) in the primary sequences that are known to be part of the agonist binding site, and by reactivity with acetylcholine affinity alkylating agents. There are at least nine neuronal α-subunits ($\alpha_1$-$\alpha_9$) that can be divided into two classes on the basis of their ability to bind α-bungarotoxin (subunits $\alpha_7$ and $\alpha_8$) and at least four neuronal β subunits ($\beta_2$-$\beta_5$).

A variety of functional neuronal nAChR subtypes have been constructed in heterologous expression studies. Pairwise coexpression of either $\alpha_2$, $\alpha_3$, or $\alpha_4$ with $\beta_2$ or $\beta_4$ subunits has produced active acetylcholine-gated ion channels. These expressed receptor subtypes differ in their pharmacological profiles with respect to both agonist and antagonist sensitivities, as well as blockade by κ-bungarotoxin and are thereby pharmacologically distinguishable. In contrast to other nAChR subunits, $\alpha_7$ has been shown to form homooligomer receptors when expressed in *Xenopus oocytes*, and these active channels are characterized by high $Ca^{2+}$ conductance and rapid desensitization.

Clearly, there is a multitude of possible neuronal nAChR subtype variations based upon combinations of five receptor subunits. Some of the pharmacological profiles for the expressed receptor subunit combinations are correlated with properties of endogenously expressed receptors found in ganglia, the CNS and in cell lines. nAChRs formed of $\alpha_4$ and $\beta_2$ subunits (nicotine binding sites) and $\alpha_7$ (which bind α-bungarotoxin) represent the predominant subtypes in the mammalian brain. Non-$\alpha_4$ $\beta_2$ nAChRs have a more limited localization within the CNS. Receptor subtypes containing $\alpha_3$ subunits are characteristic of human ganglionic nAChRs and are found in IMR-32 cells.

Evidence indicates neuronal nicotinic cholinergic channel agonists can function as potent analgesic agents by acting through neuronal nicotinic acetylcholine receptors (nAChRs). Recently, discovery of the potent antinociceptive actions of epibatidine have led to the identification and development of novel neuronal nAChR subtype-selective nAChR ligands with therapeutic potential as analgesic drugs. Substantial preclinical and clinical data suggest that compounds that selectively activate neuronal nicotinic acetylcholine receptor subtypes will have therapeutic utility for the treatment of several neurological disorders, including the treatment of moderate and severe pain across a wide range of conditions that include: acute, persistent inflammatory and neuropathic pain states. The specificity inherent in drugs targeted at neuronal receptor subtypes allows for a defined mechanism of action with reduced side effect liabilities associated with interactions with nAChRs at the neuromuscular junction.

Abreo and coworkers (Abreo, M et al., (1996) J. Med. Chem. 39:817-25) reported a novel series of 3-pyridyl ether compounds that possess subnanomolar affinity for central neuronal nicotinic acetylcholine receptors (nAChRs) and differentially activated subtypes of neuronal nAChRs. The synthesis and structure-activity relationships for the leading members of the series were described, including A-85380, which possesses a 50 pM affinity for rat brain [(3)H]-(−)-cytisine binding sites and 163% efficacy compared to nicotine with regard to stimulation of ion flux at human $\alpha_4\beta_2$ nAChR subtypes. In addition, A-84543 exhibited 84-fold selectivity to stimulate ion flux at the human $\alpha_4\beta_2$ nAChR subtype compared to human ganglionic type nAChRs.

In another study, the in vitro pharmacological properties of a novel cholinergic channel modulator ABT-089 [2-methyl-3-(2-(S)-pyrrolidinylmethoxy)-pyridine], was described. Radioligand binding studies showed that ABT-089 displays selectivity toward the high-affinity (−)-cytisine binding site present on the $\alpha_4\beta_2$ nAChR subtype (Ki=16 μM) relative to the [$^{125}$I]α-bungarotoxin binding site present on the neuronal $\alpha_7$ subtype (Ki>10,000 μM) and the muscle nAChR subtype of $\alpha_1\beta_1\delta$ subunit composition (Ki>1000 μM).

The interaction of the nicotinic agonist (R,S)-3-pyridyl-1-methyl-2-(3-pyridyl)-azetidine (MPA) with different nicotinic acetylcholine receptor (nAChR) subtypes has been established in studies employing cell lines and rat cortex. Zhang, X. et al., Neurochem Int (1998) 32:435-41. In M10 cells, which stably express the recombinant $\alpha_4\beta_2$ nAChR subtype, MPA showed an affinity (Ki=1.2 μM) which was higher than anatoxin-α>(−)-nicotine>(+)-[R]nomicotine> (−)-[S]nornicotine> and (+)-nicotine, but lower than cytisine (Ki=0.46 μM) in competing for (−)-[$^3$H]nicotine binding. MPA showed a 13-fold higher affinity for (−)-[3H]nicotine binding sites compared to the [3H]epibatidine binding sites in rat cortical membranes. In human neuroblastoma SH-SY5Y cells, which predominantly express the endogenous $\alpha_3$ nAChR subunit mRNA, MPA displaced [3H]epibatidine binding from sites with the same μM affinity as that observed in rat cortical membranes. MPA appears to have higher binding affinity to the β4-subunit containing receptor subtype than $\alpha_3$-subunit containing receptor subtype. These studies further demonstrate MPA binds to $\alpha_4\beta_2$ receptor subtype with higher affinity than (−)-nicotine and behaves as a full agonist.

From the molecular and cellular mechanism of action defined for nAChR agonists, such as ABT-594, these compounds are expected to exhibit anti-nociceptive action on the peripheral terminals of primary afferent nerves when applied intraoperatively in an irrigation solution directly to a tissue or a joint.

Representative examples of suitable neuronal nicotinic agonists for the practice of the present invention include, without limitation: (R)-5-(2-azetidinylmethoxy)-2-chloropyridine (ABT-594); (S)-5-(2-azetidinyl-methoxy)-2-chloropyridine (S-enantiomer of ABT-594); 2-methyl-3-(2-(S)-pyrrolidinylmethoxy)-pyridine (ABT-089); (R)-5-(2-Azetidinylmethoxy)-2-chloropyridine (ABT-594); (2,4)-Dimethoxy-benzylidene anabaseine (GTS-21); SBI-1765F and RJR-2403, as described in Holladay, M., Dart, M., and Lynch, J. (1997) J. Medicinal Chemistry 40:4169-4194; 3-((1-methyl-2(S)-pyrrolidinyl)methoxy)pyridine (A-84543); 3-(2(S)-azetidinylmethoxy)pyridine (A-85380); (+)-anatoxin-A and (−)anatoxin-A (1R)-1-(9-Azabicyclo[4.2.2]non-2-en-2-yl)-ethanoate fumarate, (R,S)-3-pyridyl-1-methyl-2-(3-pyridyl)azetidine (MPA), and others shown below in Table 22.

TABLE 22

Neuronal Nicotinic Acetylcholine Receptor Agonists

| Compounds | Therapeutic Acceptable Concentrations (nM) | Therapeutic Efficient Concentrations (nM) | Preferred Concentrations (nM) | Most Preferred Concentrations (nM) |
|---|---|---|---|---|
| A-84543 | 0.01-250,000 | 0.02-50,000 | 0.1-10,000 | 10-2,000 |
| A-85380 | 0.02-500,000 | 0.1-100,000 | 1-20,000 | 100-4,000 |
| ABT-089 | 0.02-500,000 | 0.1-100,000 | 1-20,000 | 100-4,000 |
| ABT-594 | 0.05-500,000 | 0.2-100,000 | 2-20,000 | 20-5,000 |
| MPA | 0.02-250,000 | 0.1-50,000 | 1-10,000 | 10-2,000 |
| ABT-418 | 0.02-500,000 | 0.1-100,000 | 1-20,000 | 100-5,000 |
| GTS-21 | 0.02-500,000 | 0.1-100,000 | 1-10,000 | 100-2,000 |
| SIB-1765F | 0.06-500,000 | 0.3-150,000 | 3-15,000 | 300-6,000 |
| RJR-2403 | 0.05-400,000 | 0.4-80,000 | 4-20,000 | 40-8,000 |
| cytisine | 0.04-500,000 | 0.2-200,000 | 2-50,000 | 20-10,000 |
| lobeline | 0.02-400,000 | 0.1-100,000 | 1-20,000 | 10-5,000 |

18. Soluble Receptors

Another class of agents useful in the present invention are soluble receptors. From a classical pharmacological perspective, the definition of a receptor is based upon the concept that a receptor is able to selectively recognize a ligand and, importantly, provide a mechanism for the transduction of this recognition event into a physiological response. At the cellular level, an operational definition of a receptor is that it must recognize a distinct ligand and transmit information from the signal provided by the ligand into a form that alters the state of the cell. Hence, the attributes of ligand recognition and signal transduction are both used to define classes of receptors. The transduction process may be mediated through an integral part of the receptor structure or may involve receptor interactions with additional non-receptor proteins (e.g. G-proteins), or some combination thereof. Receptor molecules belonging to the ligand-gated ion channel, G-protein coupled, receptor tyrosine kinase, and cytokine superfamilies are located in the plasma membrane of the cell and mediate signal transduction from a ligand bound to an extracellular ligand-binding domain of the receptor to an intracellular domain.

In contrast, soluble receptors retain the ability to selectively recognize and bind their cognate ligands, but lack the capacity for signal transduction. A number of endogenous soluble receptors are produced and directly secreted by cells, or alternatively, are released from the extracellular membrane surface of cells into extracellular fluids. By the term "soluble," it is intended that the receptor polypeptide be soluble in aqueous solutions that include, but are not limited to, detergent-free aqueous buffers, including saline and buffered media, and body fluids such as extracellular fluid (ECF), blood, plasma and serum. While soluble receptors may be derived from membrane-bound receptors, the uncomplexed soluble receptor is not anchored on cell surfaces. Specifically included are truncated or soluble forms of the IL-1, IL-2, IL-4, IL-6, TNF, and FGF receptors not having a cytoplasmic and transmembrane region.

Within the context of defining soluble receptors as pharmacological antagonists, the term soluble receptor includes, but is not limited to: (1) soluble receptors which correspond to naturally (endogenous) produced amino acid sequences or soluble fragments thereof consisting of an extracellular domain of a full-length membrane receptor; (2) recombinant soluble receptors which are truncated or partial amino acid sequences of the full-length naturally occurring receptor polypeptide which retain the ability to bind cognate ligand and retain biological activity, and analogs thereof; and (3) chimeric soluble receptors which are recombinant soluble receptors comprised of truncated or partial sequences corresponding to a portion of the extracellular binding domain of the full-length receptor amino acid sequences attached through oligomers (e.g. amino acids) to an amino acid sequence corresponding to a portion of an IgG polypeptide (e.g. IgG hinge and Fc domain) which retain biological activity and the ability to bind cognate ligand.

Soluble, extracellular ligand-binding domains of cytokine receptors occur naturally in body fluids and are thought to be involved in the regulation of the biological activities of cytokines. The naturally occurring existence of soluble, truncated forms of a number of cytokine receptors has been reported (IL-1R, IL-4R, IL-6R, TNFR). For example, soluble TNFR is found at concentrations of about 1-2 ng/ml in the serum and urine of healthy subjects. Lacking signal transduction functions, these cytokine binding proteins arise as a result of alternative splicing of the mRNA for the complete receptor sequence (membrane-bound form) or as a result of proteolytic cleavage and release of the membrane-bound form of the receptor. Although the in vivo functions of these soluble truncated receptors are not fully established, they appear to act as physiological antagonists of their complementary endogenous cytokines. This antagonism occurs because scavenging of the free ligand through binding to its cognate soluble receptor reduces the effective free concentration available to the membrane-bound receptors, and actions of the cytokines are only produced subsequent to binding to cell surface receptors.

These soluble receptors can be viewed as natural antagonists of their cognate membrane-bound receptors by competing with cell surface receptors for common pool of free ligand. Thus, the pharmacological function of soluble receptors as antagonists is mediated by their unique ability to alter free ligand bioavailability, rather than compete with an endogenous ligand for a common binding site on a membrane receptor. Addition of soluble receptors renders target cells less sensitive to the activity of the cognate ligands, effectively neutralizing the biological activity of the ligand. Experiments in which recombinant soluble receptors have been administered in vivo have demonstrated the capacity to inhibit inflammatory responses and act as antagonists.

Perioperative delivery of a soluble receptor(s), as defined herein, in a physiologic carrier delivered directly to a surgical site, enables the soluble receptor to act locally to reduce the levels of free or "active" endogenous polypeptides to preemptively inhibit inflammation and pain.

a. Classification and Examples of Soluble Receptors i. Tumor Necrosis Factor (TNF) Receptor Family TNF-α is a cytokine mainly produced by activated macrophages that has many biological actions including cytotoxicity, anti-viral activity, immunoregulatory activities, and transcriptional regulation of several genes that are mediated by specific TNF receptors. Originally, two different receptors termed TNF-R1 and TNF-R2 were cloned and characterized. Currently, 12 different TNF-related receptors have been identified (TNFR-1, TNFR-2, TNFR-RP, CD27, CD30, CD40, NGF receptor, PV-T2, PV-A53R,4-1BB, OX-40, and Fas) with which eight different TNF-related cytokines associate. All of these receptors (except PV-T2 and PV-A53R) also exist as naturally produced, endogenous soluble receptors.

Receptors in this family are single transmembrane proteins with considerable homology in their extracellular domains whereas their relatively short intracellular domains bear very little sequence homology. The actions of TNF are produced subsequent to binding of the factor to cell surface receptors that are present on virtually all cell types that have been studied. Two receptors have been identified and cloned. One receptor type, termed TNFR-II (or Type A or 75 kDa) shows an apparent molecular weight of 75 kDa. This gene encodes a transmembrane protein of 439 amino acids. The other receptor type, termed TNFR-I (or Type B or 55 kDa) shows an apparent molecular weight of 55 kDa and encodes a transmembrane protein of 426 amino acids. Both of the receptors exhibit high affinity for binding TNFα. Soluble TNF receptors (sTNFR) have been isolated and proved to arise as a result of shedding of the extracellular domains of the membrane-bound receptors. Two types of sTNFR have been identified and designated as sTNFRI (TNF BPI) and sTNFRII (TNF BPII). Both of these soluble receptor forms have been shown to represent the truncated forms of the two types of TNFR described above.

TNFα plays a central role in the sequence of cellular and molecular events underlying the inflammatory response. Among the proinflammatory actions of TNF, it stimulates the release of other proinflammatory cytokines including IL-1, IL-6, and IL-8. TNFα also induces the release of matrix metalloproteinases from neutrophils, fibroblasts and chondrocytes. This cytokine, along with IL-1, is considered to initiate and produce pathological effects in the joint such as leukocyte infiltration, synovial hyperplasia, synovial cell activation, cartilage breakdown and inhibition of cartilage matrix synthesis. In particular, during acute inflammatory states, increased production of TNFα by synovial cells occurs and increased levels of TNFα are found in the synovial fluid of joints. Thus, local delivery of a soluble TNFα receptor in an irrigation solution during a surgical procedure will bind free TNFα and function as an antagonist of TNF receptors in the surrounding tissue, thus providing an anti-inflammatory effect.

In one aspect, the present invention relates to the perioperative delivery of a chimeric soluble receptor (CSR) protein, in which the extracellular domain of a TNF receptor (either TNFRI or TNRII), which possesses binding activity for a TNF molecule, is covalently linked to a domain of an IgG molecule. In particular, and by way of first example, a chimeric polypeptide (recombinant chimera) comprising the extracellular domain of the TNF receptor extracellular polypeptide coupled to the CH2 and CH3 regions of a mouse IgG1 heavy chain polypeptide, as disclosed in U.S. Pat. No. 5,447,851, could be used for the present purpose. The chimeric TNF soluble receptor (also termed the "chimeric TNF inhibitor" in U.S. Pat. No. 5,447,851) has been shown to bind TNFα with high affinity and has been demonstrated to be highly active as an inhibitor of TNFα biological activity. In addition, a second example is a chimeric fusion construct comprised of the ligand-binding domain of a TNF receptor with portions of the Fc antibody (also termed Fc fusion soluble receptors) that have been created for TNFα receptors. In another embodiment, the present invention involves perioperative delivery of a soluble TNF receptor: Fc fusion protein, or modified forms thereof, as disclosed in U.S. Pat. No. 5,605, 690. The molecular form of the active soluble receptor can be either monomeric or dimeric. Existing studies establish that such a soluble TNF receptor: Fc fusion protein (Enbrel) retains high binding affinity for TNFα and biological activity for TNFα.

ii. Interleukin-1 (IL-1) Cytokine Receptor Family

IL-1α and IL-1β are polypeptides that have a number of biological functions that include immunoregulatory, proinflammatory, and hematopoietic activities. A number of in vitro and in vivo experimental studies indicate that the ability to prevent the binding of IL-1 to its cell surface receptors will prevent IL-1 induced inflammatory and cartilage destructive effects within the joint. These actions are mediated by one of two IL-1 receptors (IL-1R), type I IL-1 (IL-1R1) or type II IL-1 (IL-1 RII) receptors. The IL-1 receptors are structurally distinct and belong to a separate superfamily characterized by the presence of immunoglobulin-binding domains. The larger human type I IL-1 receptor (80 kD) is present on numerous cell types, while the smaller human type II IL-1 receptor (60-68 kD) exhibits a more restricted distribution that includes B cells, T-cells, monocytes, and neutrophils. Structurally, the human IL-1 R1 is a transmembrane glycoprotein with a substantial intracellular domain composed of 213 amino acids ($\approx$20 kD). The IL-1 RII receptor binds IL-1β with high affinity (about 2 nM), but IL-1β binding does not initiate IL-1 receptor associated intracellular signal transduction as it does upon binding to the type I IL-1 receptor. Soluble receptor forms of both IL-1 R1 and IL-1 RII have been reported. The soluble form of IL-1 R1 is a 60 kD protein. The type II receptor serves as a precursor for a soluble IL-1 binding factor that is produced by proteolytic cleavage to yield two sizes of soluble receptors (47 kD and 57 kD).

A different type of naturally occurring, secreted soluble IL-1 receptor antagonist, alternatively referred to as the IL-1 antagonist protein (IL-1AP or IRAP) or the IL-1 receptor antagonist (IL-1RA or IL-1Ra), is expressed in synovial tissue. It binds to both cell surface IL-1 receptors, but does not induce any response and interacts with soluble IL-1 receptors. It is a product of several cell types found within the joint, including synoviocytes and chondrocytes, as well as monocytes, macrophages and fibroblasts. This protein exists as two structural variant forms, characterized as a 17 kD secretory protein (sIL-1Ra) and an 18 kD form that remains in the cytoplasm. As a specific competitive inhibitor of IL-1, IL-1Ra binds to the type I IL-1 receptor with high affinity; it does not activate the cellular signal transduction machinery activated by membrane associated IL-1 receptors. Soluble IL-1 R1 also binds the IL-1Ra with very high affinity (Kd=70 pM). The soluble type II receptor exhibits different binding characteristic than the membrane form of the receptors, exhibiting over 2000-fold lower affinity for IL-1Ra. This results in IL-Ra having greater ability to antagonize IL-1 actions. The IL-1Ra has been shown to play a physiological role in suppressing the biological actions of IL-1. Secreted IL-Ra is released in vivo during experimentally induced inflammation and as part of the natural course of many diseases.

Agents useful in the present invention include an IL-1 soluble receptor protein, which is formed of an extracellular domain of an IL-1R (either type I or II), and which is capable of binding an IL-1 cytokine molecule. In particular, and by way of example, a soluble human IL-1 receptor (shuIL-1R) polypeptide comprising essentially the amino acid sequence 1-312 as disclosed within U.S. Pat. No. 5,319,071 and U.S. Pat. No. 5,726,148 may be used in the present irrigation solutions. Alternatively, a fusion protein consisting of the sIL-1R binding domain polypeptide, as disclosed in U.S. Pat. No. 5,319,071 may be used in the invention. In addition, an IL-1 receptor antagonist as disclosed within U.S. Pat. No. 5,817,306 can be employed for the present purpose. The shuIL-1R soluble receptor has been shown to bind IL-1 with nanomolar affinity. Local delivery of an IL-1R soluble receptor, such as shuIL-1R, in an irrigation solution at a therapeutically effective concentration during an arthroscopic procedure may be used as a cartilage protective agent when applied locally to tissues of the joint in a variety of inflammatory or pathophysiological conditions. Such treatment will preemptively inhibit IL-1 stimulation of production of collagenase-1 and stromelysin-1. Employing a wholly different method for local production of type 1 soluble receptors for IL-1 and/or TNFα based on gene delivery, it has been found that the presence of soluble receptors for these cytokines are able to confer protection to the rabbit knee joint during the acute inflammatory phase of a.i.a.

iii. Class I Cytokine Receptor Family

The large hematopoietic cytokine receptor superfamily consists of EPO, IL-2, IL-3, IL-4, IL-5, IL-6, IL-7, IL-9, IL-11, IL-12, IL-13, IL-15, Epo, PRL, GH, G-CSF, and GM-CSF, LIF, CNTF, and thrombopoietin receptors. In general, these receptors mediate hematopoietic cytokine-induced growth and differentiation of hematopoietic cells, but also exhibit a wide range of biological effects on various tissues and cells.

The receptor binding subunits for Class I cytokine receptors have been characterized at the molecular level and comparison of amino acid sequences has revealed several shared structural features or regions of sequence homology. Class I cytokine receptors are characterized by the presence of one or two copies of a conserved domain of about 200 amino acids, which contain two modules of FN-III-like motifs located in the extracellular portion of the receptor. A second region is characterized by a conserved cysteine motif (four conserved cysteines and one tryptophan residue) in the N-terminal half of this homology region. Also contained in this homology region is a common Trp-Ser-X-Trp-Ser sequence (where X is a nonconserved amino acid) at the C-terminal end. There are also regions of shared amino acid sequence homology in the intracellular domains of hematopoietic receptors that are referred to as homology boxes 1 and 2.

The Class I cytokine receptor family has been subdivided into four receptor subfamilies based on common mechanisms of signal transduction resulting from cytokine binding to the receptor binding subunit. The EPO, G-CSF, PRL and GH receptors comprise the GH receptor subfamily in which cytokine binding to a single receptor-binding subunit promotes the formation of a functional high affinity receptor dimer on the plasma membrane. The other three subfamilies of hematopoietic receptors do not form dimers upon cytokine binding. Agonist binding to structurally unique cytokine-binding subunits for each of the members in these families of hematopoietic cytokine receptors results in the formation of a high-affinity complex with a shared signal transducing subunit.

Among the members of the Class I cytokine receptor family, soluble receptors for IL-2, IL-4, IL-6, and GM-CSF ligands are suitable for inclusion in irrigation solutions of the current invention. The use of soluble receptors for IL-6 and GM-CSF ligands is preferred in arthroscopic surgical procedures.

(a). Soluble IL-2 Receptor and IL-4 Receptor: IL-2R Subfamily

Within the IL-2 receptor (IL-2R) subfamily, the structurally unique binding subunits for IL-2, IL-4, IL-7, IL-9, IL-13 and IL-15 receptors all form high-affinity functional complexes with a common signal transduction protein referred to as the IL-2γ subunit. The IL-2 receptor, unlike other receptors in this IL-2γ family, also associates with a third transmembrane protein subunit, IL-2Rβ (75 kD). In this case, the high affinity IL-2 receptor exists as a heterotrimeric complex. A soluble form of the IL-2Rα receptor appears in serum, concomitant with its increased expression on cells and there are reports of a soluble form of the IL-2Rβ. Agents useful in the solutions of the present invention include human IL-2Rβ soluble receptor (shIL-2R) proteins, in which the extracellular domain of a cytokine receptor possesses binding activity for the IL-2 cytokine molecule. In particular, and by way of example, the human IL-2Rβ soluble receptor (shIL-2R) protein is disclosed within U.S. Pat. No. 5,449,756.

The ligand binding subunit of the human IL-4R present on the cell surface receptor is a 140 kDa transmembrane glycoprotein containing 800 amino acids: a 207 residue extracellular domain; a 24 residue transmembrane domain; and a 569 residue intracellular domain. In addition to the full-length receptor, an alternatively spliced IL-4R transcript that encodes a secreted form of the IL-4R lacking the transmembrane and cytoplasmic domains has been isolated from mouse cells. A naturally occurring soluble form of the IL-4R has been identified in mouse biological fluids and murine cell culture supernatants, as well as human serum. In solution, soluble IL-4R can form 1:1:1 complexes with IL-4 and the IL-2γ subunit.

(b). Soluble IL-6 Receptor: IL-6 Cytokine Receptor Subfamily

The IL-6 receptor subfamily of Class I cytokine receptors includes the IL-6, IL-11, CNTF, OSM, and LIF receptors. These all form a high-affinity functional receptor complex upon interaction with a cytokine-occupied binding subunit with a common signal transduction protein called gp130. In the case of the IL-6 receptor, IL-6 binding to its binding subunit leads to association with a homodimer of gp130 instead of a single gp130 monomer. Recently, a human IL-12 binding receptor component has been cloned and found to be highly related in primary structure to gp130.

There exist naturally occurring soluble forms of the IL-6R that bind IL-6 with high affinity. Soluble forms have also been identified in human serum as well as in the conditioned medium of various cells, including human peripheral mononuclear cells and T-cell lines. Elevated serum soluble IL-6R levels have been shown to be associated with a number of pathological states, including significant increases in patients undergoing minor elective operations during the first postoperative week. Both soluble IL-6R and the soluble gp130 are present in nanogram quantities in the serum of normal individuals. Although the exact mechanism generating sIL-6R is not understood, it has been demonstrated that a naturally occurring alternate form of IL-6R mRNA exists and appears to be generated as a result of alternative splicing of mRNA, which encodes a soluble form of IL-6R lacking the transmembrane domain.

The various activities of IL-6 indicate it has a major role in the mediation of the inflammatory response initiated by injury. IL-6 can be considered a critical proinflammatory cytokine, which is itself upregulated in response to TNFα and IL-1 in a variety of disease states and conditions. One of the major intraarticular cytokines that has been studied in the context of joint inflammation is IL-6. In a study of comparing changes in IL-6 levels in synovial fluid after anterior cruciate ligament rupture in the knee, IL-6 increased about 1,500-fold in the acute injured knee. Thus, IL-6 is a target for the pharmacologic control of inflammation. The present invention includes the perioperative delivery of a sIL-6R in an irrigation solution during an arthroscopic procedure in order to inhibit inflammation. The inhibition of the proinflammatory activity of IL-6 by the IL-6 soluble receptor is of benefit in controlling or reducing inflammation in the joint.

iv. Receptor Tyrosine Kinases

A wide variety of polypeptide growth factor receptors that possess intrinsic tyrosine kinase activity have now been characterized for which soluble receptors are disclosed for use in the solutions of the present invention. Such agents include extracellular portions of receptor tyrosine kinase receptors and chimeric soluble tyrosine kinase receptors. Activated receptor tyrosine kinases (RTKs) undergo dimerization and initiate signaling through tyrosine-specific phosphorylation of diverse intermediates, activating a cascade of intracellular pathways that regulate phospholipid and arachidonate metabolism, calcium mobilization, protein phosphorylation (involving other protein kinases), and transcriptional regulation. The growth-factor-dependent tyrosine kinase activity of the RTK cytoplasmic domain is the primary mechanism for generation of intracellular signals that initiate multiple cellular responses.

Many of the RTK subfamilies are recognizable on the basis of architectural similarities in the catalytic domain as well as distinctive motifs in the extracellular ligand-binding regions. The extracellular domain of the RTKs typically contains discrete structural units that are derived from a limited group of biochemical domains. These domains include: cysteine rich regions, immunoglobulin-like loops (IgLs), or fibronectin type III (FN-III) domains. Based upon these structural considerations, a nomenclature defining several subfamilies of RTKs has been proposed. The eight receptor families referred to on the basis of their prototypic members include: EGF-receptor, insulin receptor, PDGF-receptor, the fibroblast growth factor receptor (FGFR), Neurotrophin (Trk) receptor, Hepatocyte Growth factor (HGF) receptor, Vascular Endothelial Growth Factor (VEGF) receptor and Eph receptors. Members of a given subfamily share common structural features that are distinct from those found in other subfamilies.

A common structural feature shared by a group of three subfamilies, the EGF (EGFR, ErbB2, ErbB3, ErbB4), insulin and Eph (Eph, Elk, Eck, Cck5, Sek, Eck, and Erk) receptors, is the presence of cysteine-rich regions in the extracellular domain. The Eph receptor extracellular region is characterized by a single cysteine-rich box that is related to the two tandem cysteine-rich boxes found in members of the EGF receptor subfamily. Also containing a single cysteine-rich region, the insulin receptor is the prototypic receptor for a subfamily whose distinctive structural feature is its organization as a heterotetrameric species of two α and two β subunits. The extracellular ligand-binding subunit, α, is disulfide-linked to the transmembrane β subunit, which contains the tyrosine kinase domain.

A second major structural category is represented by a group of three subfamilies, fibroblast-growth factor receptors (FGFR), platelet-derived growth factor receptors (PDGFR) and Flt1/VEGF receptors, which are characterized by extracellular domains consisting of three, five, or seven IgLs. Cytoplasmic regions of these receptors contain a tyrosine kinase domain that is interrupted by a "kinase insert." Receptors containing five IgLs include two PDGF receptors (α and β), the macrophage colony stimulating factor-1 receptor (CSF-1R), the c-kit protein (a receptor for the steel ligand) and the product of the FLT3/FLK2 gene. The FGF receptors, which have three IgLs, constitute a separate subfamily. Currently, there are at least seven FGFR members that mediate a diverse array of biological responses, including the capacity to induce angiogenesis (FGFR-1, FGFR-2, FGFR-3 and FGFR-4). In addition, a group of RTKs with seven extracellular IgLs has been proposed to represent a separate VEGF receptor subfamily. Its known members, FLT1, FLK1 and FLT4, show a similarity of structure and expression. Several lines of evidence suggest that this subfamily of growth factor receptors play an important role in the growth and differentiation of endothelial cells.

One group of receptors that does not fall into either of the above categories is the Trk subfamily. Recent work on the Trk subfamily has established that these molecules constitute signal-transducing receptors for a family of structurally and functionally related neurotrophic factors, collectively known as the neurotrophins. This receptor subfamily (Trk, TrkB, TrkC) contains neither cysteine-rich regions nor IgLs in the extracellular domain. Instead, cysteines are found throughout the binding domain and are also clustered near the N-terminus.

Although there is a tremendous diversity among the numerous members of the RTK family, the signaling mechanisms used by these receptors share many common features. Biochemical and molecular genetic studies have shown that binding of the ligand to the extracellular domain of the RTK rapidly activates the intrinsic tyrosine kinase catalytic activity of the intracellular domain which is essential for signal transduction.

For example, recombinant chimeric soluble receptors derived from Axl, Sky, Mer and c-Met (receptor for hepatocyte growth factor) and composed of the extracellular ligand-binding domain of these receptors fused to the Fc region of the human immunoglobulin domain IgG1 heavy chain have been created (Nagata, et al., *J. Biol. Chem.*, 271:30022-27, 1996). Naturally occurring counterparts for these chimeric receptors are not known to exist. These tyrosine kinase receptor-Fc fusion (RTK-Fc) proteins were expressed in COS-7 cells and subsequently purified from the conditioned media by conventional protein A-Sepharose chromatography. Analysis showed these RTK-Fc fusion proteins were expressed as disulfide-linked dimers as has been found previously for other IgG fusion proteins. Binding analysis of the immobilized RTK-Fc fusion protein showed that the kinetics of specific protein ligands could be quantitatively determined for Axl-Fc, Sky-Fc, and Mer-Fc soluble receptors. This study confirmed that such chimeric soluble receptors retain binding affinity for endogenous protein ligands that activate the full-length endogenous forms of these receptors. Thus, in one aspect, the present invention is directed to the local delivery of such RTK-Fc fusion proteins (or modified forms thereof) in an irrigation solution as therapeutic agents to reduce the "active" form or concentration of their respective cognate biological ligand.

Representative soluble receptors for use in the solutions of the present invention, and dosages, are listed in Table 23 below.

TABLE 23

| | Soluble Receptors | | | |
|---|---|---|---|---|
| Soluble Receptor | Therapeutic Preferred Concentrations (nM) | Therapeutic Preferred Concentrations (nM) | Therapeutic Preferred Concentrations (nM) | Most Preferred Concentrations (nM) |
| sTNFR | 0.005-50,000 | 0.02-10,000 | 0.1-1000 | 1-200 |
| Chimeric rhTNFR:Fc | 0.005-50,000 | 0.02-10,000 | 0.1-1000 | 1-200 |
| Human type I IL-1R | 0.01-50,000 | 0.02-10,000 | 0.1-1000 | 1-200 |
| Human type II IL-1R | 0.01-50,000 | 0.02-10,000 | 0.1-1000 | 1-200 |
| Shuman IL-1R fusion protein with DYKDDDDK on N-terminus | 0.01-50,000 | 0.02-10,000 | 0.1-1000 | 1-200 |
| sIL-6R | 0.01-100,000 | 0.02-20,000 | 0.1-1000 | 1-200 |
| bFGF receptor | 0.01-50,000 | 0.02-5,000 | 0.1-1000 | 1-200 |
| PDGF | 0.01-50,000 | 0.02-5,000 | 0.1-1000 | 1-200 |

VI. METHOD OF APPLICATION

The solution of the present invention has applications for a variety of operative/interventional procedures, including surgical, diagnostic and therapeutic techniques. The irrigation solution is perioperatively applied during arthroscopic surgery of anatomic joints. As used herein, the term "perioperative" encompasses application intraprocedurally, pre- and intraprocedurally, intra- and postprocedurally, and pre-, intra- and postprocedurally. Preferably the solution is applied preprocedurally and/or postprocedurally as well as intraprocedurally. Such procedures conventionally utilize physiologic irrigation fluids, such as normal saline or lactated Ringer's, applied to the surgical site by techniques well known to those of ordinary skill in the art. The method of the present invention involves substituting the anti-pain/anti-inflammatory irrigation solutions of the present invention for conventionally applied irrigation fluids. The irrigation solution is preferably applied to the wound or surgical site prior to the initiation of the procedure, preferably before tissue trauma, and continuously throughout the duration of the procedure, to preemptively block pain and inflammation. As used herein throughout, the term "irrigation" is intended to mean the flushing of a wound or anatomic structure with a stream of liquid. The term "application" is intended to encompass irrigation and other methods of locally introducing the solution of the present invention, such as introducing a gellable version of the solution to the operative site, with the gelled solution then remaining at the site throughout the procedure. As used herein throughout, the term "continuously" is intended to also include situations in which there is repeated and frequent irrigation of wounds at a frequency sufficient to maintain a predetermined therapeutic local concentration of the applied agents, and applications in which there may be intermittent cessation of irrigation fluid flow necessitated by operating technique.

In addition to use during arthroscopic procedures, the solutions of the invention may also be locally and perioperatively delivered during open surgical procedures on joints of the extremities, including but not limited to total knee, hip, ankle, toe, shoulder, elbow, wrist and finger joint replacements, the placement of implants into joints of the extremities, and for other surgical procedures on an extremity. As used herein, "extremity" refers to anatomic structures of the leg, including the hip, or of the arm, including the shoulder. Irrigation of open surgical sites at joints or extremities may be carried out in accordance with the invention by periodic direct irrigation with a bulb syringe or using other conventional techniques.

The agents of the present invention may be delivered in a formulation useful for introduction and administration of the drug into the targeted tissue or joint that enhances the delivery, uptake, stability or pharmacokinetics of the pharmacological agent. Suitable formulations include, but are not limited to, administration using microparticles, microspheres or nanoparticles composed of lipids, proteins, carbohydrates, synthetic organic compounds, or inorganic compounds. Examples of formulation molecules include, but are not limited to, lipids capable of forming liposomes or other ordered lipid structures, cationic lipids, hydrophilic polymers such as poly (D,L lactic acid-coglycolic acid) polymers, chitosan, heparin, lipids capable of forming ordered lipid structures such as unilamellar and multilamellar liposomes (anionic, cationic and zwitterionic), polycations (e.g. protamine, spermidine, polylysine), peptide or synthetic ligands and antibodies capable of targeting materials to specific cell types, gels including hydrogels, slow or sustained release matrices, soluble and insoluble particles, as well as formulation elements not listed. Several of these formulations utilize sustained release vehicles, including microparticles, microspheres, nanoparticles, proteins, liposomes, carbohydrates, gels, and other slow or sustained release matrices.

The solutions of the present invention may be prepared at concentrations greater than that intended for local delivery. Such concentrates are subsequently diluted with physiologic carrier to the desired local concentration in accordance with the present invention, prior to delivery. The solutions of the present invention may also be prepared as lyophilized formulations, which are subsequently solubilized or reconstituted in a physiologic carrier at the desired concentration prior to local delivery. The solutions of the present invention may also include excipients, such as stabilizers and buffers, for example.

In one aspect, the present invention provides for the local delivery of the pharmacological agents of the invention using an irrigation solution containing the drug which is present at low concentration and which enables the drug to be delivered directly to the affected tissue or joint. The drug-containing irrigation solution is employed perioperatively during a surgical procedure. Other conventional methods used for drug delivery have required systemic administration (intramuscular, intravenous, subcutaneous) which necessitates high concentrations of drugs (and higher total dose) to be administered in order to achieve significant therapeutic concentrations in the targeted tissue or joint (e.g., the synovial fluid of the joint). Systemic administration also results in high concentrations in tissues other than the targeted tissue that is undesirable and, depending on the dose, may result in adverse side effects (e.g., bleeding, ulceration). These systemic methods subject the drug to second pass metabolism and rapid degradation, thereby limiting the duration of the effective therapeutic concentration. Since the drug is administered directly to the desired tissue, it does not depend upon vascular perfusion to carry the drug to the targeted tissue. This significant advantage allows for the delivery of the pharmacological agents of the invention using a therapeutically effective lower concentration and lower therapeutically effective total dose.

The concentrations listed for each of the agents within the solutions of the present invention are the concentrations of the agents delivered locally, in the absence of metabolic transformation, to the operative site in order to achieve a predetermined level of effect at the operative site. It is understood that the drug concentrations in a given solution may need to be adjusted to account for local dilution upon delivery. Solution concentrations are not adjusted to account for metabolic transformations or dilution by total body distribution because these circumstances are avoided by local delivery, as opposed to oral, intravenous, subcutaneous or intramuscular application.

Arthroscopic techniques for which the present solution may be employed include, by way of non-limiting example, partial meniscectomies and ligament reconstructions in the knee, shoulder acromioplasties, rotator cuff debridements, elbow synovectomies, and wrist and ankle arthroscopies. The irrigation solution is continuously supplied intraoperatively to the joint at a flow rate sufficient to distend the joint capsule, to remove operative debris, and to enable unobstructed intraarticular visualization.

A preferred solution for use in the present invention includes (a) a cyclooxygenase inhibitor (most preferably a nonselective cyclooxygenase inhibitor that also acts to inhibit lipoxygenase), (b) a serotonin$_2$ antagonist and/or a histamine$_1$ antagonist (most preferably an agent that exhibits both of these functions) and (c) an alpha adrenergic receptor agonist as a peripheral vasoconstrictor (more preferably an alpha agonist that is highly selective for alpha receptors without substantial (relatively little or no) interaction with beta receptors, and most preferably that is a mixed alpha-1 and alpha-2 agonist). One such suitable irrigation solution for control of pain and inflammation during such arthroscopic techniques is provided in Example I herein below, and utilizes ketoprofen, amitriptyline and oxymetazoline for each of the agents listed above, respectively.

This solution utilizes extremely low doses of these pain and inflammation inhibitors, due to the local application of the agents directly to the operative site during the procedure. For example, less than 0.05 mg of amitriptyline (a suitable serotonin$_2$ and histamine$_1$ "dual" receptor antagonist) are needed per liter of irrigation fluid to provide the desired effective local tissue concentrations that would inhibit 5-HT$_2$ and H$_1$ receptors. This dosage is extremely low relative to the 10-25 mg of oral amitriptyline that is the usual starting dose for this drug. This same rationale applies to other agents utilized in the solutions of the present invention.

In each of the surgical solutions of the present invention, the agents are included in low concentrations and are delivered locally in low doses relative to concentrations and doses required with conventional methods of drug administration to achieve the desired therapeutic effect. It is impossible to obtain an equivalent therapeutic effect by delivering similarly dosed agents via other (i.e., intravenous, subcutaneous, intramuscular or oral) routes of drug administration since drugs given systemically are subject to first- and second-pass metabolism. The agents are delivered locally in accordance with the present invention to provide a desired local level of therapeutic effect and results in a blood plasma level for the agent that is significantly less than that which would result form systemic administration of the agent to achieve the same level of therapeutic effect. Given that only a small fraction of the drug delivered intra-articularly is absorbed by the local synovial tissue, the difference in plasma drug levels between the two routes of administration is much greater than the difference in total drug dosing levels.

Practice of the present invention should be distinguished from conventional intra-articular injections of opiates and/or local anesthetics at the completion of arthroscopic or "open" joint (e.g., knee, shoulder, etc.) procedures. The solution of the present invention is used for continuous infusion throughout the surgical procedure to provide preemptive inhibition of pain and inflammation. In contrast, the high concentrations necessary to achieve therapeutic efficacy with a constant infusion of local anesthetics, such as lidocaine (0.5-2% solutions), would result in profound systemic toxicity.

Upon completion of the procedure of the present invention, it may be desirable to inject or otherwise apply a higher concentration of the same pain and inflammation inhibitors as used in the irrigation solution at the operative site, as an alternative or supplement to opiates.

Some of the solutions of the present invention may suitably also include a gelling agent to produce a dilute gel. This gellable solution may be applied, for example, to deliver a continuous, dilute local predetermined concentration of agents.

VII. EXAMPLES

The following are several formulations in accordance with the present invention suitable for certain operative procedures followed by a summary of three clinical studies utilizing the agents of the present invention.

A. Example I

The following composition is suitable for use in anatomic joint irrigation during arthroscopic procedures. Each drug is solubilized in a carrier fluid containing physiologic electrolytes, such as normal saline or lactated Ringer's solution, as are the remaining solutions described in subsequent examples.

Irrigation Solution for Arthroscopy

TABLE 24

| Class of Agent | Drug | Concentration (Nanomolar): Therapeutic | Preferred | Most Preferred |
|---|---|---|---|---|
| serotonin$_2$ antagonist and histamine$_1$ antagonist | amitriptyline | 100-50,000 | 1,000-25,000 | 5,000 |
| cyclooxygenase inhibitor | ketoprofen | 1,000-500,000 | 5,000-100,000 | 18,000 |
| mixed alpha-1/alpha-2 agonist (vasoconstrictor) | oxymetazoline | 0.01-25,000 | 0.05-15,000 | 5,000 |

B. Example II

Alternate Irrigation Solution for Arthroscopy

The following composition is also suitable for use in anatomic joint irrigation during arthroscopic procedures.

TABLE 25

| Class of Agent | Drug | Concentration (Nanomolar): Therapeutic | Preferred | Most Preferred |
|---|---|---|---|---|
| mixed alpha-1/alpha-2 agonist (vasoconstrictor) | naphazoline | 0.1-250,000 | 1-25,000 | 5,000 |
| serotonin$_2$ antagonist and histamine$_1$ antagonist | amitriptyline | 100-50,000 | 1,000-25,000 | 5,000 |
| cyclooxygenase inhibitor | ketoprofen | 1,000-500,000 | 5,000-100,000 | 20,000 |

C. Example III

Alternate Irrigation Solution for Arthroscopy

The following composition is also suitable for use in anatomic irrigation during arthroscopic procedures.

TABLE 26

| Class of Agent | Drug | Concentration (Nanomolar): Therapeutic | Preferred | Most Preferred |
|---|---|---|---|---|
| mixed alpha-1/alpha-2 agonist (vasoconstrictor) | oxymetazoline | 0.01-25,000 | 0.05-15,000 | 5,000 |
| Neurokinin$_1$ antagonist | GR82334 | 1-1,000 | 10-500 | 100 |
| cyclooxygenase inhibitor | ketoprofen | 1,000-500,000 | 5,000-100,000 | 20,000 |

D. Example IV

Alternate Irrigation Solution for Arthroscopy

The following composition is also suitable for use in anatomic irrigation during arthroscopic procedures.

TABLE 27

| Class of Agent | Drug | Concentration (Nanomolar): Therapeutic | Preferred | Most Preferred |
|---|---|---|---|---|
| mixed alpha-1/alpha-2 agonist (vasoconstrictor) | oxymetazoline | 0.01-25,000 | 0.05-15,000 | 5,000 |
| histamine$_1$ antagonist | pyrilamine | 0.01-10,000 | 0.1-1,000 | 200 |
| MAP kinase inhibitor | SB220025 | 0.05-100,000 | 0.2-25,000 | 20-5,000 |

E. Example V

Alternate Irrigation Solution for Arthroscopy

The following composition is also suitable for use in anatomic irrigation during arthroscopic procedures.

TABLE 28

| Class of Agent | Drug | Concentration (Nanomolar): Therapeutic | Preferred | Most Preferred |
|---|---|---|---|---|
| mixed alpha-1/alpha-2 agonist (vasoconstrictor) | oxymetazoline | 0.01-25,000 | 0.05-15,000 | 5,000 |
| serotonin$_2$ antagonist and histamine$_1$ antagonist | amitriptyline | 100-50,000 | 1,000-25,000 | 5,000 |
| cyclooxygenase inhibitor | celecoxib | 0.05-15,000 | 0.3-3,000 | 500 |

F. Example VI

Inhibition of Synovial Plasma Extravasation by Preemptive Administration of an Anti-Inflammatory Irrigation Solution in the Rat Knee A rat knee joint model of acute inflammation (synovial plasma extravasation) was studied to determine whether preemptive intraarticular irrigation of the drugs ketoprofen, amitriptyline, or oxymetazoline, alone or in combination, can reduce inflammatory solution-induced plasma extravasation. These three drugs, also used in the exemplary solution of Example I above, were selected in part because of their abilities to collectively inhibit the inflammatory effects of biogenic amines, eicosanoid production, and the release of neuropeptides from C-fiber terminals.

1. Methods

These studies were approved by the Committee on Animal Research of the University of California, San Francisco. 104 male Sprague-Dawley rats (Bantin and Kingman, Fremont, Calif.) weighing 320 to 350 g were used. They were housed at 25° C. under controlled lighting conditions (lights 6:00 AM to 6:00 PM) with food and water ad libitum.

Rats were anesthetized with sodium pentobarbital (65 mg/kg intraperitoneally; Abbott, Chicago, Calif.). The animals then received a tail vein injection of Evans blue dye (50 mg/kg in a concentration of 20 mg/mL; Sigma, St. Louis, Mo.), which was used as a marker for plasma protein extravasation. The knee joint capsule was exposed by excising the overlying skin, and a 30-gauge needle, which was used for the infusion of fluid, was inserted into the joint. After perfusion of 100-200 µL of fluid, a 25-gauge outflow needle was also placed into the joint space approximately 3 mm from the inflow needle to extract fluid. The infusion and extraction rate (200 µL/min) was controlled by an SP120p push-pull syringe pump (WPI, Sarasota, Fla.). Perfusate samples were collected over 5-min intervals for 50 min. The samples were immediately centrifuged to determine whether red blood cells were present; only blood-free samples were acceptable. Samples were then analyzed for Evans blue dye concentration by spectrophotometric measurement of absorbance at 620 nm (Spectronic 21D; Spectronic Instruments, Inc., Rochester, N.Y.). Absorbance is linearly related to dye concentration.

All drugs and chemicals, with the exception of mustard oil, were from Sigma, St. Louis, Mo. Plasma extravasation was activated by an inflammatory solution consisting of 1 µM 5-HT, 200 nM bradykinin, and 1% mustard oil (allyl isothiocyanate; Aldrich Chemical, Milwaukee, Wis.). Bradykinin and 5-HT were dissolved in saline, and mustard oil was dissolved first in 40% ethanol and 20% Tween 80, with a final concentration of ethanol 1% and Tween 80 0.5%. Amitriptyline and oxymetazoline were dissolved in saline, and ketoprofen was dissolved first in 40% ethanol and then diluted to a final ethanol concentration of <1%.

To determine the optimal anti-inflammatory drug concentrations, each of the three drugs-amitriptyline, oxymetazoline, and ketoprofen-was tested for its ability to dose-dependently inhibit plasma extravasation produced by a single inflammatory mediator (5HT, mustard oil, and-bradykinin, respectively) against which the drug is targeted. An initial 5-min intraarticular baseline perfusion with 0.9% saline was followed by a 10-min perfusion with the drug, followed by a 35-min perfusion with the drug and the inflammatory mediator.

In studies that tested the ability of the inflammatory solution to stimulate plasma extravasation, the inflammatory solution was perfused for 35 min, beginning immediately after a 15-min baseline saline perfusion. In experiments testing preemptive administration of the single drugs against the inflammatory solution, amitriptyline, oxymetazoline, or ketoprofen was added to the saline perfusion after 5 min for a period of 10 min, then the drugs were perfused together with the inflammatory solution for an additional 35 min. In addition to perfusing the individual drugs before, and then together with, the inflammatory solution, two-drug and three-drug combinations were also tested for their ability to inhibit inflammatory solution-induced plasma extravasation. Each of the four possible combinations (amitriptyline+ketoprofen, amitriptyline+oxymetazoline, ketoprofen+oxymetazoline, and amitriptyline+ketoprofen+oxymetazoline) were perfused 10 min before, and then together with, the inflammatory solution, similar to the single-drug studies. In studies testing the post-inflammatory administration of drugs, the inflammatory solution alone was perfused for 10 min after the baseline 15-min saline perfusion, followed by all three anti-inflammatory drugs together with the inflammatory solution for an additional 25 min.

A total of 68 rat knees were excluded from the study because of physical damage of the knee joint or inflow and outflow mismatch (detectable by presence of blood in perfusate and high baseline plasma extravasation levels or knee joint swelling caused by improper needle placement). After the procedure, rats were killed by a lethal injection of pentobarbital and bilateral thoracotomy.

Data are expressed as the mean±SEM of absorbance at 620 nm for each treatment group. Data were analyzed using Total Absorbance (TotAbs), which was calculated by for each treatment group by taking the sum of mean absorbance values over the time period from 5 minutes post-stimulus ($T_0$+5) to 35 minutes post-stimulus ($T_0$+35). Statistical analyses were performed using one-sided t-tests with a Bonferroni adjustment so that each set of tests had level of significance 0.05.

2. Results

Amitriptyline was tested in concentrations of 20, 200, and 2000 nM against 5-HT-induced plasma extravasation (data not shown). An initial 5-min baseline perfusion with 0.9% saline was followed by a 10-min perfusion with amitriptyline alone, followed by a 35 min perfusion of amitriptyline and 5-HT. Use of the absorbance measurement at each time point results in a calculated TotAbs. Amitriptyline 20 nM (n=6) has no significant effect on plasma extravasation levels produced by 5-HT 1 µM (n=9) (0.778±0.093 vs. 0.580±0.046; P>0.05). Amitriptyline 200 nM (n=6) inhibits 5-HT-induced plasma extravasation by 70% to 0.233±0.029 (P<0.001). Amitriptyline 2000 nM (n=6) does not result in any further significant decrease in plasma extravasation compared with the 200 nM concentration (0.196±0.042; P>0.05, 2000 vs. 200 nM).

Similarly, oxymetazoline 20 nM (n=6) has no significant effect on mustard oil-induced plasma extravasation (1%; n=6) (1.555±0.266 vs. 1.139±0.123; P>0.05) (data not shown). Oxymetazoline 200 nM (n=6) produces a 50% reduction of plasma extravasation (0.712±0.156; P=0.01). Oxymetazoline 2000 nM (n=6) does not result in any further significant decrease in plasma extravasation compared with the 200 nM concentration (0.683±0.056; P>0.05, 2000 vs. 200 nM). The inhibitory activity of ketoprofen was tested against bradykinin (200 nM)-induced (n=6), plasma extravasation at larger concentrations (75 to 7500 nM), given the extensive protein binding of ketoprofen in synovial fluid (25). Ketoprofen 75 nM (n=6) has no significant effect on bradykinin-induced plasma extravasation (1.070±0.063 vs. 0.981±0.094; P>0.05), yet ketoprofen 750 nM (n=6) reduces extravasation by 40% (0.673±0.079; P<0.005). Ketoprofen 7500 nM (n=6) does not produce any additional inhibition compared with the 750 nM concentration (0.602±0.033; P>0.05, 7500 nM vs. 750 nM) (data not shown). These dose-response data suggest that amitriptyline 200 nM, oxymetazoline 200 nM, and ketoprofen 750 nM are concentrations that are maximally effective in inhibiting plasma extravasation while avoiding unnecessarily large concentrations that may produce undesirable side effects. These concentrations were then used in the following experiments.

Intraarticular perfusion of the inflammatory solution produces a marked increase in plasma extravasation in the rat knee joint after 10 min and reaches a plateau by 15 min that continues for the remainder of the perfusion time (a total of 35 min) (FIG. 1). Use of the absorbance measurement at each time point results in a calculated TotAbs of 4140±420 for the inflammatory solution alone. The perfusion of a single drug-amitriptyline 200 nM (3430±140), oxymetazoline 200 nM (3330±170), or ketoprofen 750 nM (3080±260) 10 min before, and then in combination with, the inflammatory solution does not significantly inhibit plasma extravasation.

The two-drug combinations also do not inhibit inflammatory solution-induced plasma extravasation (FIG. 2). Amitriptyline+ketoprofen (2760±260), amitriptyline+oxymetazoline (2860±400), and ketoprofen+oxymetazoline (2370±300) have TotAbs values not statistically different from inflammatory solution-induced plasma extravasation (4140±420). There are no significant differences among the two-drug combinations.

The combination of all three drugs (amitriptyline, ketoprofen, and oxymetazoline) perfused 10 min before, and then in combination with, the inflammatory solution produces a dramatic inhibition of plasma extravasation (1640±90; P<0.001) (FIG. 3). Compared with the two-drug combinations, the three-drug combination is better at inhibiting plasma extravasation than amitriptyline+ketoprofen (P<0.001), amitriptyline+oxymetazoline (P<0.01), or ketoprofen+oxymetazoline (P<0.05).

To determine the advantage of preemptively perfusing the three-drug solution, the inflammatory solution was perfused for 10 min before the perfusion of the inflammatory solution+ three-drug solution (FIG. 3). The above studies preperfused the drug solutions, whereas this study delays the addition of the drugs to the perfusion until 10 min after the administration of the inflammatory solution has begun. The group with the post-inflammatory three-drug administration shows significantly less inhibition of plasma extravasation than that with the preemptive administration (P<0.01) and is not significantly different from the inflammatory solution alone. Therefore, the three-drug solution loses all ability to inhibit inflammatory solution-induced plasma extravasation when perfused only 10 min later than the inflammatory solution.

3. Discussion

Synovial perfusion of each one of the three drugs 10 min before, and then in combination with, the inflammatory solution (bradykinin, 5-hydroxytryptamine, and mustard oil) did not reduce plasma extravasation. Similarly, two-drug combinations did not significantly reduce inflammatory solution-induced plasma extravasation. The combination of all three drugs (amitriptyline, ketoprofen, and oxymetazoline) produced a dramatic inhibition of plasma extravasation and was more effective than any of the two-drug combinations. A comparison between the preemptive (10 min before inflammatory solution perfusion) and post-inflammatory administration (10 min after inflammatory solution perfusion) showed that the post-inflammatory administration of the three-drug solution lost all ability to inhibit inflammatory solution-induced plasma extravasation.

This study demonstrated that a combination of the tested anti-inflammatory drugs including a vasoconstrictor delivered locally throughout the duration of the inflammatory process was found to be the optimal method for inhibiting the effects of peripherally acting inflammatory mediators.

While the preferred embodiment of the invention has been illustrated and described, it will be appreciated that various changes to the disclosed solutions and methods can be made therein without departing from the spirit and scope of the invention. For example, alternate alpha-2 adrenergic vasoconstrictors, pain inhibitors and anti-inflammation agents may be discovered that may augment or replace the disclosed agents in accordance with the disclosure contained herein. It is therefore intended that the scope of letters patent granted hereon be limited only by the definitions of the appended claims.

The embodiments of the invention in which an exclusive property or privilege is claimed are defined as follows:

1. A method of inhibiting pain and inflammation at a joint during an arthroscopic surgical procedure, comprising delivering to a joint during an arthroscopic procedure a solution comprising:
   oxymetazoline,
   at least a first pain/inflammation inhibitory agent comprising a cyclooxygenase inhibitor; and
   a liquid carrier, wherein the solution is applied locally and perioperatively to the joint.

2. The method of claim 1, further comprising at least a second pain/inflammation inhibitory agent selected from the group consisting of: a serotonin$_2$ receptor antagonist, a serotonin$_3$ receptor antagonist, a serotonin$_{1B}$ receptor antagonist, a histamine receptor antagonist; a bradykinin receptor antagonist; a kallikrein inhibitor; a tachykinin receptor antagonist; a calcitonin gene-related peptide receptor antagonist; an interleukin receptor antagonist; a phospholipase inhibitor; a cyclooxygenase inhibitor; a lipoxygenase inhibitor; a prostanoid receptor antagonist; a leukotriene receptor antagonist; an opioid receptor agonist; a purinoceptor antagonist; an ATP-sensitive potassium channel opener; a mitogen-activated protein kinase (MAPK) inhibitor; a neuronal nicotinic acetylcholine receptor agonist; and a soluble receptor.

3. The method of claim 1, wherein the first pain/inflammation inhibitory agent is ketoprofen.

4. The method of claim 1, wherein the first pain/inflammation inhibitory agent comprises ketoprofen and the solution further comprises amitriptyline as a second pain/inflammation inhibitory agent.

5. The method of claim 1, wherein the solution further comprises a second pain/inflammation inhibitory agent selected from the group consisting of serotonin receptor antagonists and histamine receptor antagonists.

6. The method of claim 5, wherein the second pain/inflammation inhibitory agent functions as both a serotonin receptor antagonist and a histamine receptor antagonist.

7. The method of claim 1, comprising continuously applying the solution to the joint.

8. The method of claim 7, comprising continuously irrigating the joint with the solution.

9. The method of claim 1, wherein the solution is applied by irrigation of the joint.

10. The method of claim 1, wherein the solution is locally applied to the joint in the absence of metabolic transformation.

11. The method of claim 1, wherein the perioperative application of the solution comprises intraprocedural application together with preprocedural or postprocedural application of the solution.

12. The method of claim 11, wherein the perioperative application of the solution comprises preprocedural, intraprocedural and postprocedural application of the solution.

13. The method of claim 1, wherein the oxymetazoline in the solution is delivered locally at a concentration of no greater than 300,000 nanomolar.

14. The method of claim 13, wherein the oxymetazoline in the solution is delivered locally at a concentration of no greater than 75,000 nanomolar.

15. The method of claim 13, wherein the first pain/inflammation inhibitory agent in the solution is delivered locally at a concentration of no greater than 500,000 nanomolar.

16. The method of claim 15, wherein the first pain/inflammation inhibitory agent in the solution is delivered locally at a concentration of no greater than 100,000 nanomolar.

17. The method of claim 1, wherein each of the agents in the solution is included at a concentration or dosage that is sufficient to provide a level of pain/inflammation inhibitory or vasoconstrictive effect at the joint when delivered locally to the joint and that results in a plasma concentration that is less than a plasma concentration that would be required to achieve the same level of inhibitory or therapeutic effect at the joint when delivered systemically.

18. The method of claim 1, comprising intermittently applying the solution to the joint.

19. A method of inhibiting pain and inflammation at a joint of an extremity during an arthroscopic or open surgical procedure or other extremity procedure, comprising delivering to the surgical site during the procedure a solution comprising:
   oxymetazoline,
   at least a first pain/inflammation inhibitory agent comprising a cyclooxygenase inhibitor; and
   a liquid carrier, wherein the solution is applied locally and perioperatively to the surgical site.

20. The method of claim 19, wherein the solution further comprises at least a second pain/inflammation inhibitory agent selected to act on a different molecular target than oxymetazoline and the first pain/inflammation inhibitory agent.

21. The method of claim 19, comprising continuously applying the solution to the surgical site.

22. The method of claim 19, wherein the solution is applied by irrigation of the surgical site.

23. The method of claim 19, wherein the perioperative application of the solution comprises intraprocedural application together with preprocedural or postprocedural application of the solution.

24. The method of claim 23, wherein the perioperative application of the solution comprises preprocedural, intraprocedural and postprocedural application of the solution.

25. The method of claim 19, wherein each of the agents in the solution is included at a concentration or dosage that is sufficient to provide a level of pain/inflammation inhibitory or vasoconstrictive effect at the surgical site when delivered locally to the surgical site and that results in a plasma concentration that is less than a plasma concentration that would be required to achieve the same level of inhibitory or therapeutic effect at the surgical site when delivered systemically.

26. The method of claim 19, wherein the first pain/inflammation inhibitory agent is ketoprofen.

27. The method of claim 26, wherein the solution further comprises amitriptyline as a second pain/inflammation inhibitory agent.

28. The method of claim 19, wherein the procedure during which the solution is delivered comprises an open joint procedure.

29. The method of claim 28, wherein the procedure during which the solution is delivered comprises a total joint replacement.

30. The method of claim 29, wherein the solution is applied by intermittent irrigation during the procedure.

31. The method of claim 19, comprising intermittently applying the solution to the joint.

32. A method of inhibiting pain and inflammation at a surgical or operative/procedural sites during an oral/dental surgery, ocular surgery or burn treatment procedures, comprising delivering to a site during an oral/dental surgery, ocular surgery or burn treatment procedure a solution comprising:

oxymetazoline,
at least a first pain/inflammation inhibitory agent comprising a cyclooxygenase inhibitor; and
a liquid carrier, wherein the solution is applied locally and perioperatively to the site.

33. The method of claim 32, wherein the first pain/inflammation inhibitory agent is ketoprofen.

34. The method of claim 32, wherein the first pain/inflammation inhibitory agent comprises ketoprofen and the solution further comprises amitriptyline as a second pain/inflammation inhibitory agent.

35. The method of claim 32, wherein the solution further comprises amitriptyline as a second pain/inflammation inhibitory agent.

36. The method of claim 32, wherein the solution further comprises amitriptyline as a second pain/inflammation inhibitory agent.

37. The method of claim 26, wherein the solution further comprises amitriptyline as a second pain/inflammation inhibitory agent.

38. The method of claim 2, wherein the tachykinin receptor antagonist is selected from the group consisting of a neurokinin, receptor subtype antagonist and a neurokinin$_2$ receptor subtype antagonist.

39. The method of claim 2, wherein the phospholipase inhibitor is selected from the group consisting of a $PLA_2$ isoform inhibitor and a $PLC_\gamma$ isoform inhibitor.

40. The method of claim 2, wherein the cyclooxygenase inhibitor is selected from the group consisting of a non-selective cyclooxygenase inhibitor and a cyclooxygenase-2 selective inhibitor.

41. The method of claim 2, wherein the prostanoid receptor antagonist is selected from the group consisting of an eicosanoid EP-1 receptor subtype antagonist, an eicosanoid EP-4 receptor subtype antagonist, and a thromboxane receptor subtype antagonist.

42. The method of claim 2, wherein the leukotriene receptor antagonist is selected from the group consisting of a leukotriene $B_4$ receptor subtype antagonist and a leukotriene $D_4$ receptor subtype antagonist.

43. The method of claim 2, wherein the opioid receptor agonist is selected from the group consisting of a μ-opioid receptor subtype agonists, a δ-opioid receptor subtype agonist, and a κ-opioid receptor subtype agonist.

44. The method of claim 2, wherein the purinoceptor antagonist is a $P_{2X}$ receptor antagonist.

* * * * *

UNITED STATES PATENT AND TRADEMARK OFFICE
CERTIFICATE OF CORRECTION

PATENT NO. : 9,254,271 B2
APPLICATION NO. : 12/384781
DATED : February 9, 2016
INVENTOR(S) : Gregory A. Demopulos et al.

It is certified that error appears in the above-identified patent and that said Letters Patent is hereby corrected as shown below:

| COLUMN | LINE | ERROR |
|---|---|---|
| In the Specification | | |
| 9 | 4 | "neurokinin," should read --neurokinin$_1$-- |
| 9 | 9 | "PLCY" should read --PLC$_\gamma$-- |
| 13 | 24 | "$\alpha_2$ agonist" should read --$\alpha_1$ agonist-- |
| 15 | 38 | "alpha. 2" should read --alpha-2-- |
| 19 | 34 | "2-[(5-methylbenz-1-α-4-azin-6-yl)imino]imidazoline" should read --2-[(5-methylbenz-1-ox-4-azin-6-yl)imino]imidazoline-- |
| 21 | Table 4 | Replace Table 4 with the following: |

TABLE 4
Therapeutic and Preferred Concentrations of Pain/Inflammation Inhibitory Agents

| Class of Agent | Therapeutic Concentrations (Nanomolar) | Preferred Concentrations (Nanomolar) |
|---|---|---|
| Serotonin$_{1A}$ Agonists: | | |
| buspirone | 1 - 1,000 | 10 - 200 |
| sumatriptan | 1 - 1,000 | 10 - 200 |
| Serotonin$_{1B}$ Agonists: | | |
| sumatriptan | 1 - 1,000 | 10 - 200 |
| Serotonin$_{1D}$ Agonists: | | |
| sumatriptan | 10-2,000 | 100-1,000 |
| Serotonin$_{1E}$ Agonists: | | |
| ergonovine | 10-2,000 | 100-1,000 |
| Serotonin$_{1F}$ Agonists: | | |
| sumatriptan | 1 - 1,000 | 10 - 200 |

| | | |
|---|---|---|
| 28 | 44 | "COX I" should read --COX-1-- |

Signed and Sealed this
Third Day of May, 2016

Michelle K. Lee
*Director of the United States Patent and Trademark Office*

CERTIFICATE OF CORRECTION (continued)
U.S. Pat. No. 9,254,271 B2

| COLUMN | LINE | ERROR |
|---|---|---|
| In the Specification | | |
| 29 | 61 | "10(1H)" should read --10(11H)-- |
| 33 | 44 | "iM" should read --µM-- |
| 38 | 4 | "anatoxin-α>(-)-nicotine>(+)-[>(+)-[R]nomicotine>" should read --anatoxin-a>(-)-nicotine>(+)-[>(+)-[R]nornicotine>-- |
| In the Claims | | |
| 58 | 21-22 | "neurokinin," should read --neurokinin$_1$-- |